(12) United States Patent
Haggarty et al.

(10) Patent No.: US 9,265,764 B2
(45) Date of Patent: Feb. 23, 2016

(54) USES OF CHEMICALS TO MODULATE GSK-3 SIGNALING FOR TREATMENT OF BIPOLAR DISORDER AND OTHER BRAIN DISORDERS

(75) Inventors: Stephen J. Haggarty, Dorchester, MA (US); Daniel Fass, Winchester, MA (US); Jennifer Pan, Acton, MA (US); Josh Ketterman, Cambridge, MA (US); Edward Holson, Newton Highlands, MA (US); Tracey Lynn Petryshen, Cambridge, MA (US); Michael C. Lewis, Boston, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 399 days.

(21) Appl. No.: 12/660,591

(22) Filed: Feb. 27, 2010

(65) Prior Publication Data
US 2011/0008468 A1    Jan. 13, 2011

Related U.S. Application Data

(60) Provisional application No. 61/156,460, filed on Feb. 27, 2009.

(51) Int. Cl.
| | |
|---|---|
| *A61K 33/00* | (2006.01) |
| *A61K 31/407* | (2006.01) |
| *A61K 31/4545* | (2006.01) |
| *A61K 31/404* | (2006.01) |
| *A61K 31/553* | (2006.01) |
| *A61K 31/506* | (2006.01) |
| *A61P 25/00* | (2006.01) |
| *A61K 31/515* | (2006.01) |
| *A61K 31/675* | (2006.01) |
| *A61K 45/06* | (2006.01) |

(52) U.S. Cl.
CPC ............ *A61K 31/515* (2013.01); *A61K 31/675* (2013.01); *A61K 33/00* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,015,807 A | 1/2000 | Engel et al. | |
| 6,117,861 A | 9/2000 | Engel et al. | |
| 6,573,293 B2 | 6/2003 | Tang et al. | |
| 7,037,918 B2 | 5/2006 | Nuss et al. | |
| 7,125,905 B2 | 10/2006 | Tang et al. | |
| 7,211,600 B2 | 5/2007 | Lipson et al. | |
| 2004/0039007 A1* | 2/2004 | Forster et al. | 514/275 |
| 2004/0110837 A1 | 6/2004 | Phiel et al. | |
| 2005/0054663 A1 | 3/2005 | Bennett et al. | |
| 2005/0233010 A1* | 10/2005 | Satow | 424/715 |
| 2006/0135408 A1 | 6/2006 | Eldar-Finkelman | |
| 2006/0281787 A1 | 12/2006 | Graff | |
| 2007/0212428 A1* | 9/2007 | Wittlin | 424/722 |
| 2008/0175924 A1 | 7/2008 | Clelland et al. | |
| 2008/0207594 A1 | 8/2008 | Mussmann et al. | |
| 2009/0041863 A1 | 2/2009 | Hallahan | |
| 2010/0015130 A1 | 1/2010 | Tsai et al. | |

OTHER PUBLICATIONS

Jope, R. S. "Lithium and GSK-3: one inhibitor, two inhibitory actions, multiple outcomes." Trends in Pharmacological Sciences, 2003, 24(9), 441-443.*
Rowe, M. K.; et al. "GSK-3 is a viable potential target for therapeutic intervention in bipolar disorder." Neurosci. Biobehav. Rev., 2007, v. 31, pp. 920-931.*
Beaulieu et al., Lithium antagonizes dopamine-dependent behaviors mediated by an AKT/glycogen synthase kinase 3 signaling cascade. Proc Natl Acad Sci U S A. Apr. 6, 2004;101(14):5099-104. Epub Mar. 24, 2004.
Bregman et al., An organometallic inhibitor for glycogen synthase kinase 3. J Am Chem Soc. Oct. 27, 2004;126(42):13594-5.
Catapano et al., Kinases as drug targets in the treatment of bipolar disorder. Drug Discov Today. Apr. 2008;13(7-8):295-302. Epub Apr. 3, 2008.
Chen et al., The mood-stabilizing agent valproate inhibits the activity of glycogen synthase kinase-3. J Neurochem. Mar. 1999;72(3):1327-30.
Cohen et al., GSK3 inhibitors: development and therapeutic potential. Nat Rev Drug Discov. Jun. 2004;3(6):479-87.
Einat et al., Protein kinase C inhibition by tamoxifen antagonizes manic-like behavior in rats: implications for the development of novel therapeutics for bipolar disorder. Neuropsychobiology. 2007;55(3-4):123-31. Epub Jul. 18, 2007.
Engler et al., The development of potent and selective bisarylmaleimide GSK3 inhibitors. Bioorg Med Chem Lett. Feb. 15, 2005;15(4):899-903.
Gould et al., Beta-catenin overexpression in the mouse brain phenocopies lithium-sensitive behaviors. Neuropsychopharmacology. Oct. 2007;32(10):2173-83. Epub Feb. 14, 2007.

(Continued)

*Primary Examiner* — Mina Haghighatian
*Assistant Examiner* — Erin Hirt
(74) *Attorney, Agent, or Firm* — Wolf, Greenfield & Sacks, P.C.

(57) ABSTRACT

Aspects of this invention are related, at least in part, to the use of chemical compounds able to inhibit GSK-3 and/or to stabilize β-catenin and formulations thereof. Some aspects of this invention relate to compositions comprising such compounds. Some aspects of the invention provide methods of using such compounds and/or compositions in the treatment of subjects having a neurological disease and/or psychiatric disorder. Some aspects of this invention provide methods of using ruboxistaurin, enzastaurin, sunitinib, midostaurin, lestaurtinib, 7-hydroxystaurosporine, and/or Chir99021 in the treatment of subjects having a neurological disease and/or psychiatric disorder. In some embodiments, compounds are administered in combination with Lithium.

18 Claims, 23 Drawing Sheets

(56) References Cited

OTHER PUBLICATIONS

Gould et al., Effects of a glycogen synthase kinase-3 inhibitor, lithium, in adenomatous polyposis coli mutant mice. Pharmacol Res. Jul. 2003;48(1):49-53.

Gould et al., Emerging experimental therapeutics for bipolar disorder: insights from the molecular and cellular actions of current mood stabilizers. Mol Psychiatry. Aug. 2004;9(8):734-55.

Gould et al., Glycogen synthase kinase-3: a putative molecular target for lithium mimetic drugs. Neuropsychopharmacology. Jul. 2005;30(7):1223-37.

Gould et al., Glycogen synthase kinase-3: a target for novel bipolar disorder treatments. J Clin Psychiatry. Jan. 2004;65(1):10-21. Review.

Gould et al., In vivo evidence in the brain for lithium inhibition of glycogen synthase kinase-3. Neuropsychopharmacology. Jan. 2004;29(1):32-8.

Gould et al., Signaling networks in the pathophysiology and treatment of mood disorders. J Psychosom Res. Aug. 2002;53(2):687-97.

Gould et al., Strain differences in lithium attenuation of d-amphetamine-induced hyperlocomotion: a mouse model for the genetics of clinical response to lithium. Neuropsychopharmacology. Jun. 2007;32(6):1321-33. Epub Dec. 6, 2006.

Gould et al., Targeting glycogen synthase kinase-3 in the CNS: implications for the development of new treatments for mood disorders. Curr Drug Targets. Nov. 2006;7(11):1399-409.

Gould et al., The Wnt signaling pathway in bipolar disorder. Neuroscientist. Oct. 2002;8(5):497-511.

Ikonomov et al., Molecular mechanisms underlying mood stabilization in manic-depressive illness: the phenotype challenge. Am J Psychiatry. Oct. 1999;156(10):1506-14.

Jope et al., Glycogen synthase kinase-3 (GSK3) in psychiatric diseases and therapeutic interventions. Curr Drug Targets. Nov. 2006;7(11):1421-34.

Kaladchibachi et al., Glycogen synthase kinase 3, circadian rhythms, and bipolar disorder: a molecular link in the therapeutic action of lithium. J Circadian Rhythms. Feb. 12, 2007;5:3.

Klein et al., A molecular mechanism for the effect of lithium on development. Proc Natl Acad Sci USA. Aug. 6, 1996;93(16):8455-9.

Leng et al., Synergistic neuroprotective effects of lithium and valproic acid or other histone deacetylase inhibitors in neurons: roles of glycogen synthase kinase-3 inhibition. J Neurosci. Mar. 5, 2008;28(10):2576-88.

Manji et al., Bipolar disorder: leads from the molecular and cellular mechanisms of action of mood stabilizers. Br J Psychiatry Suppl. Jun. 2001;41:s107-19.

Manji et al., PKC, MAP kinases and the bcl-2 family of proteins as long-term targets for mood stabilizers. Mol Psychiatry. 2002;7 Suppl 1:S46-56.

Manji et al., Signal transduction pathways. Molecular targets for lithium's actions. Arch Gen Psychiatry. Jul. 1995;52(7):531-43.

Manji et al., The underlying neurobiology of bipolar disorder. World Psychiatry. Oct. 2003;2(3):136-46.

Mao et al., Disrupted in schizophrenia 1 regulates neuronal progenitor proliferation via modulation of GSK3beta/beta-catenin signaling. Cell. Mar. 20, 2009;136(6):1017-31.

Mathew et al., Novel drugs and therapeutic targets for severe mood disorders. Neuropsychopharmacology. Aug. 2008;33(9):2080-92. Epub Jan. 2, 2008.

Meijer et al., Pharmacological inhibitors of glycogen synthase kinase 3. Trends Pharmacol Sci. Sep. 2004;25(9):471-80.

Nciri et al., [Effects of low doses of Li carbonate injected into mice. Functional changes in kidney seem to be related to the oxidative status]. C R Biol. Jan. 2008;331(1):23-31. French.

Nciri et al., The effects of subchronic lithium administration in male Wistar mice on some biochemical parameters. Acta Biol Hung. Sep. 2009;60(3):273-80.

O'Donnell et al., The behavioral actions of lithium in rodent models: leads to develop novel therapeutics. Neurosci Biobehav Rev. 2007;31(6):932-62. Epub Apr. 13, 2007.

Quiroz et al., Molecular effects of lithium. Mol Interv. Oct. 2004;4(5):259-72.

Stolovich et al., Lithium can relieve translational repression of TOP mRNAs elicited by various blocks along the cell cycle in a glycogen synthase kinase-3- and S6-kinase-independent manner. J Biol Chem. Feb. 18, 2005;280(7):5336-42.

Zarate et al., Bipolar disorder: candidate drug targets. Mt Sinai J Med. May-Jun. 2008;75(3):226-47.

Zarate et al., Efficacy of a protein kinase C inhibitor (tamoxifen) in the treatment of acute mania: a pilot study. Bipolar Disord. Sep. 2007;9(6):561-70.

\* cited by examiner

Figure 2

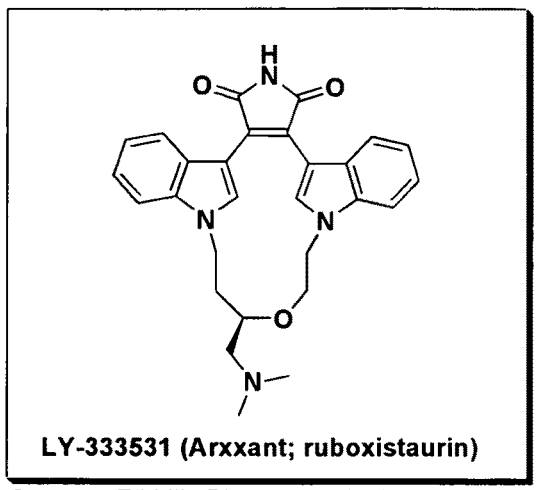

LY-333531 (Arxxant; ruboxistaurin)

Source: Eli Lilly Pharmaceuticals
Status: Phase III development as oral, well tolerated treatment for diabetic peripheral neuropathy (retinopathy and nephropathy) and macular edema
Mechanism: multitargeted kinase inhibitor
Mouse Studies: Barbuch 2005
Dose: 75 mg/kg
Vehicle: 10% acacia in water
Route: oral gavage

Cell-Based Assays
β-Catenin Stability: active (< 10 μM)

Kinase Assays
GSK-3β $IC_{50}$ = 27 nM
PKC-α $IC_{50}$ = ~360 nM (Faul 2003)
PKC-β $IC_{50}$ = ~6 nM (Faul 2003)

Plasma Cmax humans: 1000 - 4000 nM

Figure 3

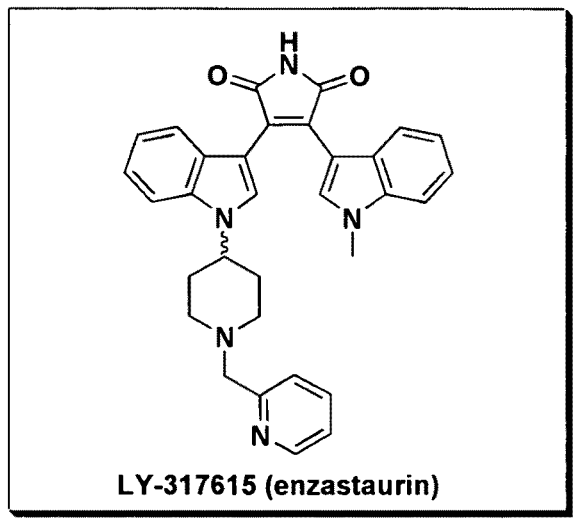

LY-317615 (enzastaurin)

Source: Eli Lilly Pharmaceuticals
Status: Phase II development as oral treatment for glioblastoma and other cancers

Mechanism: multitargeted kinase inhibitor
Mouse Studies: Tabatabai 2007; Arkadiusz 2
Dose: 75 mg/kg
Vehicle: 8% DMSO/saline solution
Route: oral gavage

Cell-Based Assays
β-Catenin Stability: active (< 10 µM)

Kinase Assays
GSK-3β $IC_{50}$ = 7 nM
PKC-α $IC_{50}$ = 800 nM (Faul 2003)
PKC-β $IC_{50}$ = 30 nM (Faul 2003)

Plasma Cmax humans: 100 - 550 nM

SU11248 (Sutent; sunitinib)

Source: Pfizer
Status: FDA approved drug for stomach and renal cancer

Mechanism: multitargeted kinase inhibitor
Mouse Studies: Saishin 2003
Dose: 50 mg/kg
Vehicle: DMSO diluted in water
Route: oral gavage

Cell-Based Assays
β-Catenin Stability: active (< 10 μM)

Kinase Assays
GSK-3β $IC_{50}$ = 1.7 μM
PKC-α $IC_{50}$ = unknown
PKC-β $IC_{50}$ = unknown
Plasma Cmax humans: 250 nM

Figure 5

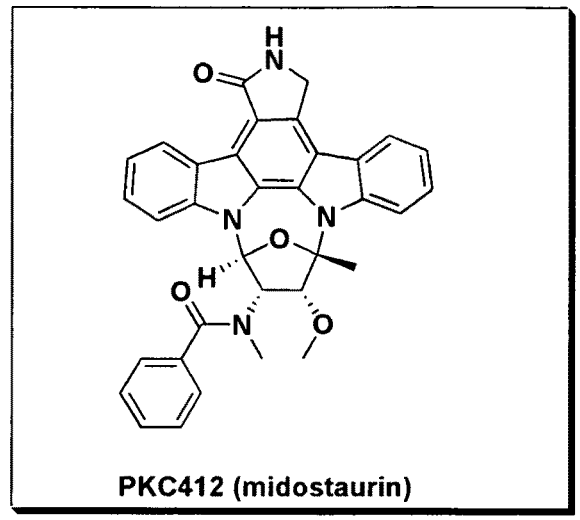

PKC412 (midostaurin)

Source: Novartis
Status: Phase III development as oral, well tolerated treatment for AML and other cancer
Development for diabetic peripheral neuropathy
Mechanism: multitargeted kinase inhibitor
Mouse Studies: Saishin 2003
Dose: 50 mg/kg
Vehicle: DMSO diluted in water
Route: oral gavage

Cell-Based Assays
β-Catenin Stability: active (< 10 μM)

Kinase Assays
GSK-3β $IC_{50}$ = <40 nM
PKC-α $IC_{50}$ = 22 nM (Seo 1999)
PKC-β $IC_{50}$ = 30 nM (Seo 1999)
Plasma Cmax humans: 1000 - 7000 nM

Figure 6

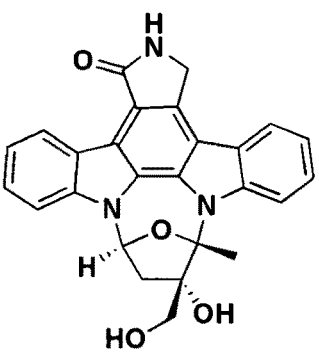

CEP-701 (lestaurtinib)

Source: Cephalon
Status: Phase III clinical trials for AML and Phase II clinical trials for myeloproliferative disorders

Mechanism: multitargeted kinase inhibitor
Mouse Studies: Weeraratna 2001
Dose: 10 mg/kg
Vehicle: 50% Tween 80/50% propylene glyc
Route: oral gavage

Cell-Based Assays
β-Catenin Stability: needs to be determined

Kinase Assays
GSK-3β $IC_{50}$ = 2.3 μM
PKC-α $IC_{50}$ = unknown
PKC-β $IC_{50}$ = unknown

Plasma Cmax humans: not available

Figure 7

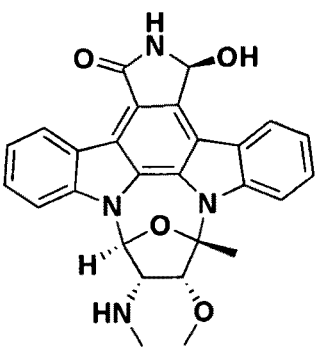

UCN-01 (7-hydroxystaurosporine)

Source: National Cancer Institite
Status: Phase II development for treatment of anaplastic large cell or mature T-cell lymphomas; Phase I for other cancers

Mechanism: multitargeted kinase inhibitor
Mouse Studies: Kurata 1999
Dose: 9 mg/kg
Vehicle: citric acid with $Na_2HPO_4$ and NaCl
Route: i.v.

Cell-Based Assays
β-Catenin Stability: needs to be determined

Kinase Assays
GSK-3β $IC_{50}$ = 100 nM
PKC-α $IC_{50}$ = 0.44 nM (Mizuno 1995)
PKC-β $IC_{50}$ = 1.7 nM (Mizuno 1995)
Plasma Cmax humans: not available Chiron 99021

ICV Chiron Dose-Response in AIH

USES OF CHEMICALS TO MODULATE GSK-3 SIGNALING FOR TREATMENT OF BIPOLAR DISORDER AND OTHER BRAIN DISORDERS

RELATED APPLICATIONS

This application claims the benefit 35 U.S.C. §119(e) of U.S. provisional application Ser. No. 61/156,460, filed Feb. 27, 2009, the entire disclosure of which is incorporated herein by reference.

FIELD OF THE INVENTION

Aspects of this invention are related, at least in part, to compositions and methods for treating neurological diseases and psychiatric disorders.

BACKGROUND OF THE INVENTION

Approximately 1.7% of the genes in the human genome encode protein kinases making kinases one of the more abundant classes of enzymes. To date, there are no therapeutic compounds used for any brain disorders, other than brain cancers, that have been developed to purposefully modulate kinase activity despite the implication of kinases as important mediators of a variety of brain functions.

Indolocarbazole alkaloids such as staurosporine and K252a, which are known to target the ATP binding site of kinases, inhibit a variety of kinases in a dose dependent manner. Despite their lack of biochemical selectivity, a number of indolocarbazoles are currently in pre-clinical and clinical development largely for oncology indications, but also for other disease areas such as diabetic macular edema. Synthetic efforts that break the planarity of the indolocarbazole core, such as bisindoylmaleimides, have given rise to inhibitors with improved specificity between families of serine/threonine and tyrosine kinases.

SUMMARY OF THE INVENTION

Aspects of this invention are related, at least in part, to the use of chemical compounds able to inhibit GSK-3 and/or to stabilize β-catenin in the treatment of subjects having a neurological disease or psychiatric disorder. Accordingly, aspects of the invention relate to new uses for previously known compounds. Further, some aspects of the invention also relate to new compounds having similar inhibitory properties.

In some embodiments, aspects of the invention relate to methods for administering a GSK-3 inhibitor to a subject having a neurological disease and/or a psychiatric disorder. In some embodiments, aspects of the invention relate to administering a combination of a GSK inhibitor (e.g., a GSK-3 inhibitor, for example, a GSK3-β inhibitor) and one or more additional therapeutic compounds to a subject having a neurological disease and/or a psychiatric disorder. In some embodiments, the additional therapeutic compounds may be any compound that is indicated for the treatment of a neurological disease and/or a psychiatric disorder, including, but not limited, to one or more of lithium (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax).

In some embodiments, aspects' of the invention relate to administering a combination of a GSK (e.g., a GSK-3 inhibitor) inhibitor and an additional therapeutic compound wherein the GSK inhibitor and/or the additional therapeutic compound are administered at a dosage that is below their respective effective dosage threshold (e.g., wherein each of the GSK inhibitor and/or the additional therapeutic compound independently is administered at a level that is below 90%, below 80%, below 70%, below 60%, below 50%, below 40%, below 30%, below 20%, below 10%, below 5%, or below 1% of its minimally effective dose). For example, in some embodiments, a GSK inhibitor (e.g., a GSK-3 inhibitor, for example, Chir99021) may be administered (e.g., to a human subject) at a dosage lower than a dosage achieving a serum level of about 5 µM, about 4 µM, about 3 µM, about 2 µM, about 1 µM, about 0.5 µM, about 0.4 µM, about 0.3 µM, about 0.2 µM, about 0.1 µM, or about 0.05 µM. In some embodiments, the subject is also being administered an additional compound (e.g., lithium) at a lower than a minimal effective dose (e.g., in humans). In some embodiments, a sub-effective dose of an additional compound indicated in the treatment of a neurological disease or psychological disorder, for example, lithium (e.g. administered as lithium chloride or lithium carbonate) is a dose achieving a serum level of less than about 0.6 mM, less than about 0.5 mM, less than about 0.4 mM, less than about 0.3 mM, less than about 0.2 mM, less than about 0.1 mM, or less than about. 0.05 mM. In some embodiments, a sub-effective dose of an additional compound indicated in the treatment of a neurological disease or psychological disorder, for example, lithium (e.g., administered as lithium chloride or lithium carbonate) is a dose achieving a serum level of less than about 2 mM, less than about 1.2 mM, less than about 0.6 mM, less than about 0.3 mM, less than about 0.1 mM, or less than about. 0.05 mM. In some embodiments, the average daily dose of the additional compound is between 600-2,400 mg/day.

Methods of measuring serum levels and adjusting doses to achieve a desired serum level, for example, an effective or sub-effective serum level, of a GSK-3 inhibitor, for example, lithium or a GSK-3 inhibitor provided herein, are well known to those of skill in the art (see, e.g., Nciri R, Allagui M S, Croute F, Vincent C, Elfeki A., *Effects of low doses of Li carbonate injected into mice. Functional changes in kidney seem to be related to the oxidative status*. C R Biol. 2008 January; 331(1):23-31; Nciri R, Allagui M S, Vincent C, Croute F, Elfeki A., *The effects of subchronic lithium administration in male Wistar mice on some biochemical parameters*. Acta Biol Hung. 2009 September; 60(3):273-80). In some embodiments, pharmaco-kinetic (PK) data may be used to determine and/or adjust the dosage of a compound provided by aspects of this invention, for example, of a GSK-3 inhibitor, or of an additional compound indicated in the treatment of a neurological disease or psychiatric disorder, for example, to achieve a desired serum level of the compound. In some embodiments, the following dosage may be used for a compound of formula 8, for example, the compound of formula 7: a dosage of about 50 mg/kg to achieve a serum level of about 69 µM; a dosage of about 12.5 mg/kg to achieve a serum level of about 15 µM; or a dosage of about 3.125 mg/kg to achieve a serum level of about 4 µM. Similarly, lower or higher serum levels may be achieved, in some embodiments, by extrapolating this dosage information, dosage information from known PK studies, or by performing PK studies.

In some embodiments, aspects of the invention relate to treating a subject that is non-responsive to lithium with a low dose of lithium (e.g., at a dose that is below the minimal effective threshold) in combination with a GSK inhibitor, for example, a GSK-3 inhibitor, (e.g., at a dose that is below its minimal effective threshold). In some embodiments, aspects of the invention relate to treating a lithium-responsive subject, with a low dose of lithium (e.g., at a dose that is below the minimal effective threshold) in combination with a GSK inhibitor (e.g., at a dose that is below its minimal effective threshold). Subjects are typically classified as lithium-responsive, if they respond to lithium administration (e.g., amelioration or disappearance of symptoms, for example, delay, amelioration, or absence of manic or depressive episodes in subjects having a psychological disorder, such as bipolar disorder). In contrast, a non-responsive subject typically shows no appreciable or substantial improvement in symptoms in response to lithium.

According to some aspects of the invention, certain GSK inhibitors have surprisingly effective properties when administered along with lithium or a related compound. According to some embodiments, certain GSK inhibitors act synergistically with lithium or a related compound. Accordingly, some aspects of this invention provide a synergistic combination of a GSK-3 inhibitor and a compound that is indicated for the treatment of a neurological disease and/or a psychiatric disorder, including, but not limited, to one or more of lithium (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax).

Some aspects of this invention relate to the surprising discovery that a selective GSK-3 inhibitor (e.g., a GSK-3 inhibitor that selectively inhibits GSK-3 relative to other kinases) has a synergistic effect when administered to a subject in conjunction with lithium or a related compound. Some aspects of this invention relate to the surprising discovery that a GSK-3 inhibitor administered at a sub-effective dose to a subject can synergistically act with lithium or a related compound administered at a sub-effective dose to the subject, wherein the synergistic action of GSK-3 inhibitor and lithium results in a combined effect that is greater than the sum of their individual effects. Accordingly, some aspects of this invention provide a synergistic combination of a GSK-3 inhibitor and a compound that is indicated for the treatment of a neurological disease and/or a psychiatric disorder, including, but not limited, to one or more of lithium (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax).

In some embodiments, the subject has been identified, indicated, or diagnosed as having the neurological disease and/or psychiatric disorder. In some embodiments, the subject is suspected to have the neurological disease and/or psychiatric disorder based on one or more symptoms or risk factors. A symptom may be indicative of any stage (e.g., early, mid, or late-stage) disease or disorder. A risk factor may be a genetic risk factor or any other known risk factor for the disease or disorder. Accordingly, some aspects of this invention provide methods for administering a GSK-3 inhibitor to a subject based on said subject being identified, indicated, suspected, or diagnosed as having a neurological disease and/or a psychiatric disorder. Some aspects of this invention provide methods for identifying or diagnosing a neurological disease and/or a psychiatric disorder in a subject and administering a GSK-3 inhibitor to the subject based on this diagnosis or identification. In some embodiments of this invention, the GSK-3 inhibitor is administered in an effective amount to treat said neurological disease and/or psychiatric disorder. In some embodiments of this invention, the GSK-3 inhibitor is administered in an amount known, shown or reported to inhibit GSK-3. In some embodiments, the GSK-3 inhibitor may be administered in an amount effective to inhibit GSK-3. In some embodiments, the GSK-3 inhibitor is administered in an amount effective to inhibit GSK-3 to less than 50% of its native activity. In some embodiments, GSK-3 inhibition may be monitored during and/or after administering a GSK-3 inhibitor according to aspects of this invention. Some methods provided by this invention comprise monitoring the subject during and/or after administering a GSK-3 inhibitor for symptoms of a neurological disease and/or psychiatric disorder. Some methods provided by this invention comprise adjusting the dosage of said GSK-3 inhibitor based on the results of said monitoring. Some methods provided by this invention comprise administering an additional compound to a subject, wherein said additional compound is indicated in the treatment of a neurological disease and/or psychiatric disorder. In some embodiments, said additional compound is lithium (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax). Some methods provided by this invention comprise administering a GSK-3 inhibitor to a subject having a neurological disease or psychiatric disorder, wherein said subject is not indicated or diagnosed to have any other disease or disorder for the treatment of which said GSK-3 inhibitor is indicated. Diabetic peripheral neuropathy, diabetic retinopathy, diabetic nephropathy, macular edema, diabetes, and malignant neoplastic disease are examples of such diseases indicated for the treatment with some GSK-3-inhibitors. Some methods provided by this invention comprise administering a GSK-3-inhibitor to a subject having a neurological disease or psychiatric disorder, wherein said subject exhibits normal glucose metabolism and glucose regulation. In some embodiments of this invention, the neurological disease is a neurodegenerative disease. Alzheimer's Disease, Fragile X Syndrome, and Amyotrophic Lateral Sclerosis (ALS) are examples of such neurodegenerative diseases. Bipolar Disorder, Autism, Schizophrenia and Depression are examples of psychiatric disorders related to by methods provided by some aspects of this invention. Some methods provided by this invention comprise administering a GSK-3 inhibitor that has not previously been indicated, demonstrated and/or suggested for the treatment of subjects having the neurological disease and/or psychiatric disorder the subject being treated has is indicated or diagnosed to have. In some embodiments of this invention, a GSK-3 inhibitor is administered that is also an activator of β-catenin signaling. In some embodiments of this invention, the GSK-3 inhibitor is Chiron 99021 (Chir99021), ruboxistaurin, enzastaurin, sunitinib, midostaurin, lestaurtinib, and/or 7-hydroxystaurosporine. In some embodiments, the GSK-3 inhibitor is a selective GSK-3 inhibitor (e.g., Chir99021).

Some aspects of this invention provide methods for administering the GSK-3 inhibitor Chir99021, ruboxistaurin, enzastaurin, sunitinib, midostaurin, lestaurtinib and/or 7-hydroxystaurosporine, to a subject having a neurological disease and/or a psychiatric disorder. In some embodiments, the subject has been identified, indicated, or diagnosed as having the neurological disease and/or psychiatric disorder. In some embodiments, the subject is suspected to have the neurological disease and/or psychiatric disorder based on one or more symptoms or risk factors. A symptom may be indicative of any stage (e.g., early, mid, or late-stage) disease or disorder. A risk factor may be a genetic risk factor or any other known risk factor for the disease or disorder. Accordingly, some aspects of this invention provide methods for administering one or more compounds described herein to a subject based on said subject being identified, indicated, suspected, or diagnosed as having a neurological disease and/or a psychiatric disorder. Some aspects of this invention provide methods for identifying or diagnosing a neurological disease and/or a psychiatric disorder in a subject and administering one or more compounds described herein to the subject based on this diagnosis or identification. Accordingly, methods for administering any of the compounds described herein to a subject based on said subject being indicated or diagnosed to have a neurological disease and/or a psychiatric disorder are provided by some aspects of this invention as well as methods comprising diagnosing a neurological disease and/or a psychiatric disorder in a subject and administering any of these compounds to the subject based on this diagnosis. In some embodiments, any of these compounds may be administered in an effective amount to treat a neurological disease and/or psychiatric disorder. In some embodiments of this invention, any of these compounds may be administered in an amount known, shown and/or reported to inhibit GSK-3. In some embodiments, any of these compounds may be administered in an amount effective to inhibit GSK-3. In some embodiments, any of these compounds may be administered in an amount effective to inhibit GSK-3 to less than 50% of its native activity. Some methods provided by this invention comprise monitoring the subject during and/or after administering any of these compounds for symptoms of said neurological disease and/or psychiatric disorder. Some methods provided by this invention comprise adjusting the dosage of any of these compounds based on the results of said monitoring. Some methods provided by this invention comprise monitoring GSK-3 inhibition in said subject during and/or after administering any of these compounds. Some methods provided by this invention comprise administering an additional compound to said subject, wherein said additional compound is indicated in the treatment of said neurological disease and/or psychiatric disorder. In some embodiments, said additional compound is lithium (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax). In some methods provided by this invention, the subject is not indicated or diagnosed to have any other disease or disorder for the treatment of which the compound being administered is indicated. Diabetic peripheral neuropathy, diabetic retinopathy, diabetic nephropathy, macular edema, diabetes, and malignant neoplastic disease are examples of such diseases indicated for the treatment with some of the compounds this invention relates to in some aspects. Some methods provided by this invention comprise administering any of these compounds to a subject having a neurological disease or psychiatric disorder, wherein said subject exhibits normal glucose metabolism and glucose regulation. In some embodiments of this invention, the neurological disease is a neurodegenerative disease. Alzheimer's Disease, Fragile X Syndrome, and Amyotrophic Lateral Sclerosis (ALS) are examples of such neurodegenerative diseases. Bipolar Disorder, Autism, Schizophrenia and Depression are examples of psychiatric disorders related to by methods provided by some aspects of this invention.

Some aspects of this invention provide compositions, comprising a compound as provided by any of formulas 1-8, as given herein, and an additional compound, wherein said additional compound is indicated in the treatment of a neurological disease or psychiatric disorder. Some aspects of this invention provide compositions, comprising a compound as provided by any of formulas 1-8, and an additional compound, wherein said additional compound is a GSK-3 inhibitor. In some of the compositions provided by aspects of this invention, said additional compound is lithium (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), and topiramate (e.g. Topamax).

In some embodiments, two or more compounds provided herein are combined together in appropriate ratios in a single composition. In some embodiments, a pharmaceutical preparation is provided that comprises a GSK-3 inhibitor and an additional compound in a ratio of about 1:10, about 1:100, about 1:1000, or about 1:10000. For example, in some embodiments, the GSK-3 inhibitor is a compound of any of formulas 1-8. In some embodiments, the additional compound is lithium, or a salt thereof (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax).

In some embodiments, a GSK-3 inhibitor is administered to a subject in temporal proximity of administration of an additional compound to the subject, for example, in a ratio as provided above or elsewhere herein, for example, in a ratio of about 1:10, about 1:100, about 1:1000, or about 1:10000. For example, in some embodiments, the GSK-3 inhibitor is a compound of any of formulas 1-8. In some embodiments, the additional compound is lithium, or a salt thereof (e.g. Eskalith, Lithobid), valproic acid (e.g. Dekapene), divalproex sodium (e.g. Depakote), sodium valproate (e.g. Depacon, Epilim), lamotrigine (e.g. Lamictal), carbamazepine (e.g. Tegretol), gabapentin (e.g. Neurontin), or topiramate (e.g. Topamax).

In some embodiments of this invention, the GSK inhibitor is a GSK-3 inhibitor. In some embodiments, the GSK inhibitor is a GSK-3$\beta$ inhibitor.

In some embodiments, aspects of the invention relate to a surprising synergistic interaction between lithium and a compound of formula 7 or 8 or a pharmaceutically acceptable salt of any thereof. Accordingly, in some embodiments, a subject (e.g., a subject having a neurological disease or a psychological disorder) may be treated using a low dose (a sub-effective dose) of both lithium and a compound of formula 7 or 8 or a pharmaceutically acceptable salt of any thereof. This can be useful, for example to reduce side effects associated with any of these compounds.

The subject matter of this application may involve, in some cases, interrelated products, alternative solutions to a particular problem, and/or a plurality of different uses of a single agent, compound, system or article.

BRIEF DESCRIPTION OF THE DRAWINGS

FIG. 2 shows the structure of Ruboxistaurin;
FIG. 3 shows the structure of Enzastaurin;
FIG. 5 shows the structure of Midostaurin;
FIG. 6 shows the structure of Lestaurtinib;
FIG. 7 shows the structure of 7-hydroxystaurosporine.

DETAILED DESCRIPTION OF THE INVENTION

The instant invention provides methods for using Glycogen synthase kinase 3 (GSK-3) inhibiting compounds in the treatment of subjects exhibiting a manifestation of a neurological disease and/or psychiatric disorder.

Figure 1:
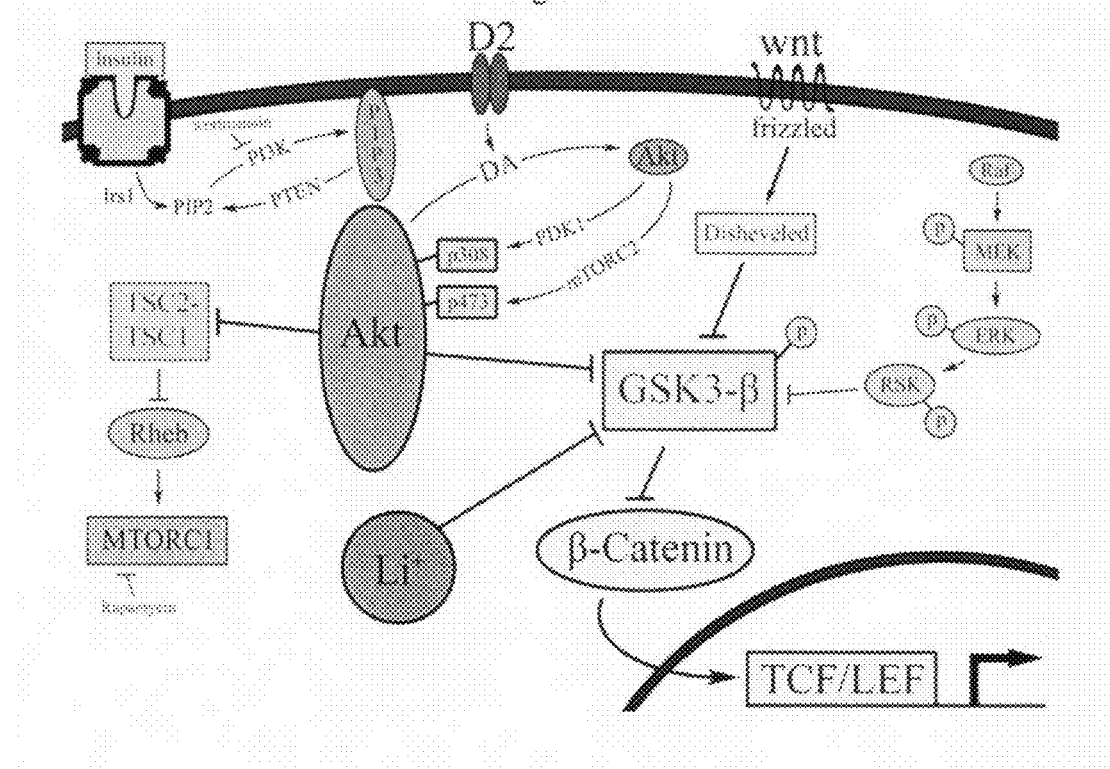
FIG. 1 illustrates a model of the GSK3 signaling pathway.
Figure 4:
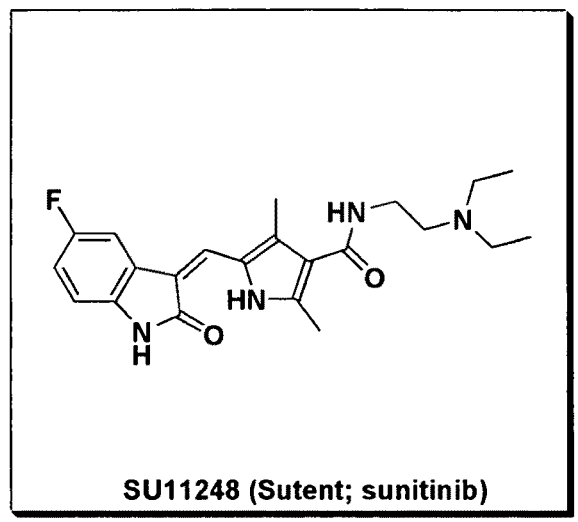
FIG. 4 shows the structure of Sunitinib.
Figure 8:
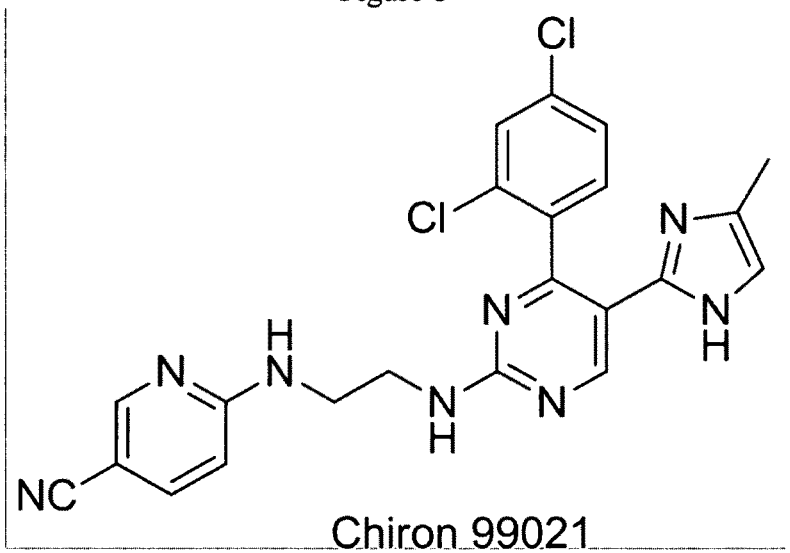
FIG. 8 shows the structure of Chiron 99021 (Chir99021)

Currently, many patients exhibiting manifestations of neurological diseases and/or psychiatric disorders are treated with compositions containing lithium. The molecular targets of lithium have been studied extensively and GSK-3 has been reported as a therapeutic target of lithium in the treatment of some psychiatric disorders (see FIG. 1 for an overview of the GSK3 signaling pathway).

GSK-3 was first identified as the kinase that phosphorylates glycogen synthase but is now known to be involved in multiple signaling pathways. GSK-3 is a proline-directed serine/threonine kinase originally identified as having an activity that phosphorylates glycogen synthase. GSK-3 includes two isoforms, GSK-3α and GSK-3β, both of which are encompassed by the term "GSK-3" as used herein. GSK-3, which is constitutively active in resting cells can be inactivated by growth factors or hormones that signal through receptor tyrosine kinases. GSK-3 has been shown, for instance, to phosphorylate β-catenin. The nucleic acid and protein sequences of GSK-3 are described, for instance, in Genbank ID NM_019884 (human GSK-3α), Genbank ID NM_002093 (human GSK-3β), and US Patent Application No. 2003/0163836, which are incorporated by reference for such teachings. These sequences can be found elsewhere herein.

GSK-3 has been identified as a therapeutic target in a variety of diseases, namely metabolic and neoplastic diseases. GSK-3 inhibition is one strategy for the treatment of such diseases, which are often caused, at least in part, by GSK-3 dysregulation or dysfunction, e.g. an elevated GSK-3 activity in specific cells or cell types. Examples for such diseases are diabetes, neoplastic malignancies, including many forms of cancer (e.g. prostate cancer, brain cancer (e.g. glioblastoma), stomach and renal cancer, blood cancer (e.g. myeloproliferative disorders, anaplastic large cell or mature T-cell lymphoma)), autoimmune disease, inflammatory disease, metabolic disorder, angiogenic disorder, glaucoma, baldness, and cardiovascular disease. Some of the compounds related to by aspects of this invention have been suggested for the treatment of patients having some of the above mentioned diseases. Aspects of this invention relate to the use of such compounds for the treatment of individuals having neurological disease or psychiatric disorder manifestations, for which the compounds according to aspects of this invention have not been indicated, demonstrated, and/or suggested thus far. Accordingly, some aspects of this invention provide methods of using ruboxistaurin, enzastaurin, sunitinib, midostaurin, lestaurtinib and/or 7-hydroxystaurosporine in the treatment of subjects having a neurological disease and/or psychiatric disorder as described herein, for which the respective compound has not been implicated, indicated, demonstrated, and/or suggested before.

Lithium, the most commonly used drug in the treatment of psychiatric disorders today, is an effective therapeutic for many, but not all, subjects having neurological diseases and/or psychiatric disorders and, according to aspects of this invention, the GSK-3 inhibiting properties of lithium play a key role in its therapeutic mechanism. Unfortunately, lithium has a very narrow effective window and can cause severe side effects, including, but not limited to extreme thirst, nausea, vomiting, diarrhea, drowsiness, muscle weakness, tremor, lack of coordination, hallucinations, seizures (blackout or convulsions), vision problems, dizziness, fainting, slow heart rate, or fast or uneven heartbeats.

Some aspects of this invention relate to the identification of selective GSK-3 inhibitors that do not appreciably target other structurally similar kinases (e.g., CDK5) and are optimized for use in the CNS. This rationale provides an approach to enhance or mimic the mechanisms of action of lithium. To date, no such compounds exist as most are direct ATP competitive inhibitors. However, since lithium itself is not a specific inhibitor of GSK-3, and a therapeutic concentration of 0.6-1.2 mM is required, it would be beneficial to identify improved GSK-3 inhibitors that are safe enough for chronic use and are capable of penetrating the brain.

In some aspects, this invention provides GSK-3 inhibiting compounds useful in the treatment of neurological diseases or psychiatric disorders. Some aspects of this invention relate to establishing the use of a drug or compound, effective for the treatment of neurological diseases and/or psychiatric disorders, that do not show the severe side effects observed in the clinical use of lithium. This approach has the potential to improve the clinical perspective for many patients. Compounds as provided by aspects of this invention could be used either alone or in combination with established drugs. As an example for combination therapy, a compound according to aspects of this invention might be used in combination with lithium, enabling the administration of a lower dose of lithium, thus decreasing the likelihood of lithium toxicity.

Similarly, some aspects of this invention provide that combining a compound described herein with lithium, or any other therapeutic effective for the treatment of a specific disease or disorder, results in a synergistic effect of the combination of those therapeutics not observed in the use of the single compounds. In some embodiments, a pharmaceutical composition is provided, comprising a combination of a therapeutic GSK inhibitor, for example, a GSK-3 inhibitor, as described herein, with an additional therapeutic compound, for example, lithium, or any other therapeutic effective in the treatment of a neurological disease or psychological disorder. In some embodiments, a pharmaceutical composition comprising a synergistic combination of a therapeutic GSK inhibitor, for example, a GSK-3 inhibitor, as described herein, with an additional therapeutic compound, for example, lithium, or any other therapeutic effective in the treatment of a neurological disease or psychological disorder, is provided.

Some, aspects of the invention relate to using one or more selective GSK-3 inhibitors in combination with lithium (and/or related compounds), wherein all the compounds are administered at doses below their respective minimal effective thresholds. In some embodiments, this avoids unwanted side-effects associated with current dosage levels. According to some aspects of the invention, lower than effective threshold levels of compounds are surprisingly effective when used in combination based on the synergistic effectiveness of combinations of compounds described herein. Effective dosages of the compounds provided by aspects of this invention are well known to those of skill in the art and are described in more detail elsewhere herein. In general, an effective dose of a compound for the treatment of a neurological disease or psychological disorder is a dose that achieves an alleviation of the specific disease or disorder being treated, for example, by prevention, inhibition, amelioration, delay, or ablation of a symptom of such a disease or disorder, whereas a sub-effective dose of a compound is a dose that does not achieve such an effect. In some embodiments, compounds may be administered at doses that are several fold lower than their minimally effective dose (e.g., at least about 2 fold lower, at least about 5 fold lower, at least about 10 fold lower, at least about 20 fold lower, or even lower, than their minimally effective dose). In some embodiments, a method of administration of a synergistic combination of compounds as provided by aspects of this invention, for example a combination comprising each compound at less than 75%, 50%, less than 25%, less than 10%, less than 5%, or less than 2.5% of its minimally effective dose is provided. In some embodiments, a synergistic, therapeutically effective combination of a GSK-3 inhibitor as provided in any of formulas 1-8 at less than 20% or less than 10% of its minimally effective dose and of lithium at less than 75%, less than 50%, less than 25%, or less than 10% of its minimally effective dose, is provided. Methods of using such a synergistic combination in the treatment of a neurological disease or psychological disorder are also provided.

Inhibition of GSK-3 in the treatment of neurological disease or psychiatric disorder can be effected by administering a GSK-3 inhibitor to a subject having such a disease or disorder. A GSK-3 inhibitor may directly or indirectly down-regulate the activity of GSK-3, for example by directly modifying the activity of GSK3 by binding or protein modification, such as acetylation or methylation, or by interacting with a member of the GSK-3 signaling pathway, either upstream or downstream of GSK-3. In some embodiments, compounds of the invention are GSK-3 inhibitors (e.g., GSK-3β inhibitors such as inhibitor compounds that specifically or preferentially inhibit GSK-3, e.g., GSK-3β activity). Some of the compounds related to by some aspects of the current invention are GSK-3β inhibitors. Most GSK-3 inhibitors are identified based on their interaction with GSK-3β. However, some GSK-3β inhibitors also inhibit the activity of GSK-3α. Some aspects of this invention relate to methods of administering a GSK-3 inhibitor at a dosage that effects inhibition of total GSK-3 activity to 50% or less of the native total GSK-3 activity. Some aspects of this invention relate to inhibiting GSK-3β activity to 50% or less of its native activity.

According to some aspects of this invention, the chemical compounds according to formula 1 (ruboxistaurin), formula 2 (enzastaurin), formula 3 (sunitinib), formula 4 (midostaurin), formula 5 (lestaurtinib), formula 6 (7-hydroxystaurosporine), formula 7 (Chir99021), and formula 8 are GSK-3 inhibitors.

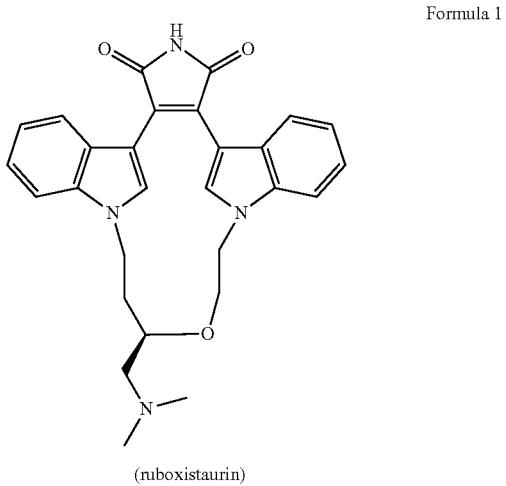

(ruboxistaurin)

Formula 1

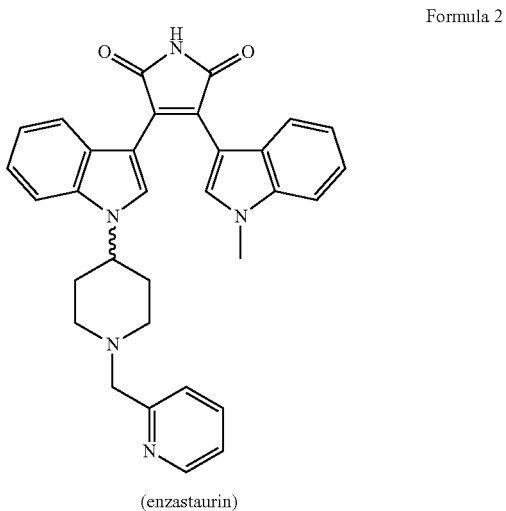

(enzastaurin)

Formula 2

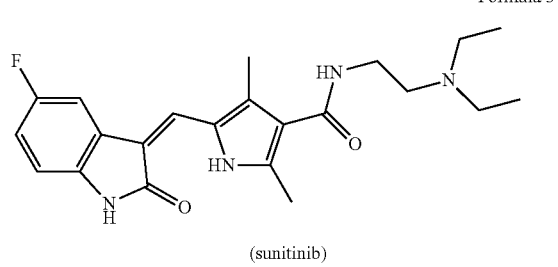

(sunitinib)

Formula 3

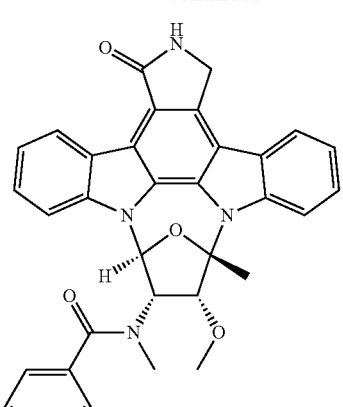

(midostaurin)

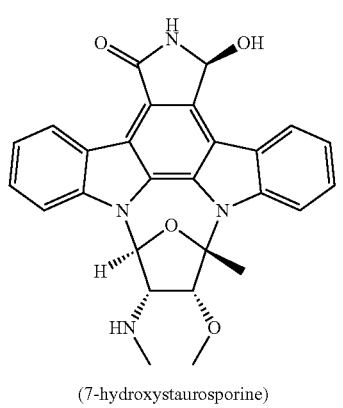

(lestaurtinib)

[structure]

(7-hydroxystaurosporine)

[structure]

(Chir99021)

Formula 4

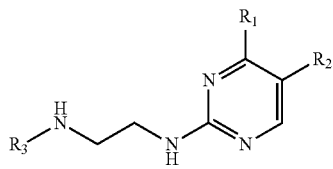

(R1, R2, R3 = aryl, heteroaryl, or H; R3 = acyl, alkyl, sulfonyl, or urea)

Additional compounds useful as GSK-3 inhibitors according to some aspects of this invention are the compounds described in U.S. Pat. No. 7,037,918, incorporated in its entirety by reference herein.

Some aspects of this invention relate to the identification of selective GSK-3 inhibitors that do not appreciably target other structurally similar kinases (e.g., CDK5) and are optimized for use in the CNS. Some embodiments provide methods for the identification of selective GSK-3 inhibitors. In some embodiments, kinase selectivity of a GSK-3 inhibitor is determined by testing binding affinity of the GSK-3 inhibitor to a plurality of kinases, for example, in an active-site dependent competition binding assay, such as a KINOMEscan assay (see, e.g., Fabian et al. (2005) Nat. Biotechnol. 23, 329; Karaman et al. (2008) Nat. Biotechnol. 26, 127). Exemplary KINOMEscan assay results for some GSK-3 inhibitors provided herein are shown in Table 1.

TABLE 1

Selectivity data for certain GSK-3 inhibitors (10 μM) against a panel of 358 kinases.

| Compound | Number of Binding Targets (kinases) | KINOMEscan Selectivity Score (S35) (number of kinases bound/number of kinases tested) |
|---|---|---|
| CHIR-99021 | 10 | 0.028 |
| SB-216763 | 31 | 0.086 |
| enzastaurin | 75 | 0.209 |
| ruboxistaurin | 95 | 0.265 |
| BIO | 170 | 0.474 |

In some embodiments, a selective GSK-3 inhibitor as used herein is a GSK-3 inhibitor that binds and/or inhibits GSK-3, and binds and/or inhibits fewer targets or achieves a smaller selectivity score in a kinase binding assay than BIO. In some embodiments, a selective GSK-3 inhibitor is a GSK-3 inhibitor that binds and/or inhibits GSK-3, and binds and/or inhibits fewer targets or achieves a smaller selectivity score in a kinase binding assay than ruboxistaurin. In some embodiments, a selective GSK-3 inhibitor is a GSK-3 inhibitor that binds and/or inhibits GSK-3, and binds and/or inhibits fewer targets or achieves a smaller selectivity score in a kinase binding assay than enzastaurin. In some embodiments, a selective GSK-3 inhibitor is a GSK-3 inhibitor that binds and/or inhibits GSK-3, and binds and/or inhibits fewer targets or achieves a smaller selectivity score in a kinase binding assay than SB-216763. In some embodiments, a selective GSK-3 inhibitor is a GSK-3 inhibitor that binds and/or inhibits GSK-3, and binds and/or inhibits fewer targets or achieves a smaller selectivity score in a kinase binding assay than Chir99021. In some embodiments, a selective GSK-3 inhibitor is a GSK-3 inhibitor that binds and/or inhibits GSK-3 but does not detectably bind and/or inhibit any other kinase.

The effectiveness of a GSK inhibitor in inhibiting GSK can be measured by methods well known to those in the art.

Quantitative measures of enzyme inhibitory and binding affinity properties, for example, $IC_{50}$ and $K_i$, are well known in the art as are methods to determine such values for a specific compound, for example, by functional antagonist assays or competition binding assays. In some embodiments, the $IC_{50}$ of a drug can be determined from a dose-response curve. In some embodiments, the $IC_{50}$ value of a GSK-3 inhibitor is the concentration determined to inhibit half of the maximum biological response of the GSK-3 inhibitor, for example, the concentration that results in half of a TCF/LEF reporter signal in an in vitro assay, as described herein.

In some embodiments, a GSK inhibitor, for example, a GSK-3 inhibitor (e.g., a GSK-3β inhibitor) is a compound having an $IC_{50}$ of about 250004 or less. In some embodiments, a GSK inhibitor, for example, a GSK-3 inhibitor (e.g., a GSK-3β inhibitor) is a compound having a sub-mM $IC_{50}$. In some embodiments, a GSK inhibitor, for example, a GSK-3 inhibitor (e.g., a GSK-3β inhibitor) is a compound having a sub-μM $IC_{50}$.

Accordingly, in some embodiments, a GSK-3 inhibitor has an IC50 or a $K_i$ that is lower than lithium in an in vitro assay. In some embodiments, a GSK-3 inhibitor has an IC50 or a $K_i$ that is about 1 mmolar. In some embodiments, a GSK-3 inhibitor has an IC50 or a $K_i$ that is sub-millimolar, for example 10-100 micromolar, or 1-10 micromolar. In some embodiments, a GSK-3 inhibitor has an IC-50 or a $K_i$ that is about micromolar. In some embodiments, a GSK-3 inhibitor has an IC-50 or a $K_i$ that is submicromolar, for example 10-100 nanomolar, or 1-10 nanomolar. In some embodiments, a GSK-3 inhibitor has an IC-50 or a $K_i$ that is about nanomolar. In some embodiments, a GSK-3 inhibitor has an IC-50 or a $K_i$ that is subnanomolar, for example 10-100 picomolar, or 1-10 picomolar.

Certain compounds described herein are being developed in clinical trials for the treatment of various metabolic and/or neoplastic disorders (FIG. 2-7), but have not been indicated, demonstrated, and/or suggested for the treatment of neurological disorders and/or psychiatric diseases as provided by this invention. Accordingly, aspects of the invention relate to new applications for compounds described herein.

Some aspects of this invention provide methods for administering any of the GSK-3 inhibitors described herein based on a subject being indicated or diagnosed to have a neurological disease or a psychiatric disorder. Some aspects of this invention provide methods wherein the GSK-3 inhibitor administered has not been indicated, demonstrated, and/or suggested for the treatment of said disease or disorder before. For example, this invention provides methods comprising administering ruboxistaurin, enzastaurin, sunitinib, midostaurin, lestaurtinib, and/or 7-hyroxystaurosporine to a subject diagnosed with a neurological disease (for example Alzheimer's Disease) and/or a psychiatric disorder (for example Depression) for the treatment of which these compounds have not been indicated or suggested thus far.

In some embodiments of this invention methods are provided comprising administering a compound provided by aspects of this invention in addition to an additional compound to a subject, wherein said additional compound is indicated in the treatment of said neurological disease and/or psychiatric disorder. Administration of ruboxistaurin, enzastaurin, sunitinib, midostaurin, lestaurtinib, and/or 7-hyroxystaurosporine in addition to lithium to a subject diagnosed with a neurological disease (for example Alzheimer's) or psychiatric disorder (for example Depression) is an example of such a method. Lithium and/or lithium salts, for example lithium carbonate, citrate, sulfate, orotate (e.g. Eskalith, Lithobid), valproic acid (Dekapene), divalproex sodium (Depakote), sodium valproate (Depacon, Epilim), lamotrigine (Lamictal), carbamazepine (Tegretol), gabapentin (Neurontin), and topiramate (Topamax) are examples of suitable drugs for use as additional compounds. A combination of three or more compounds comprising at least one of the compounds provided by aspects of this invention, is also envisioned. In some embodiments, a pharmaceutical composition comprising a compound provided by aspects of this invention, for example, a GSK-3 inhibitor, and an additional compound indicated in the treatment of a neurological disease or psychological disorder is provided. In some embodiments, a method for the manufacture of a medicament comprising a compound provided by aspects of this invention, for example, a GSK-3 inhibitor, and an additional compound indicated in the treatment of a neurological disease or psychological disorder.

In some embodiments of this invention, a compound according to aspects of this invention is administered to a subject based on having been diagnosed to have a neurological disease or disorder and the subject is monitored for symptoms of said neurological disease and/or psychiatric disorder. This monitoring will generally take place in a clinical setting and in the form of an assessment of symptoms related to the neurological disease or psychiatric disorder the subject has been diagnosed with. This monitoring can be part of routinely performed assessments based on the diagnosis or indication of the subject to have the disease or disorder, or can be performed specifically to assess the effect of the administered compound on the subject. In the case of repeated administrations over a period of time, this monitoring can take place during or after the administration period according to aspects of this invention.

In some embodiments, GSK-3 activity is monitored in a subject before, during, and/or after administration of a compound according to aspects of this invention. Methods for this monitoring are well established and well-known to those of skill in the art. Examples for such methods are assays that survey the level of GSK-3 protein, assays that directly assay GSK-3 activity, assays that survey the phosphorylation status of a GSK-3 target molecule, and assays that survey the state of a biomarker indicative of GSK-3 activity.

GSK-3 activity, for example, GSK-3β activity, can directly be determined in a GSK-3 kinase assay for example by measuring the transfer of $^{32}P$ from $[^{32}P]$-γ-ATP to the GSK-3-specific peptide substrate GSM as outlined in Ryves et al., Anal Biochem. 1998 Nov. 1; 264(1):124-7. Reagent kits for direct assessment of GSK-3 activity are commercially available. Alternatively, the phosphorylation state of GSK-3 target molecules (molecules that are phosphorylated by GSK-3 in vivo or in vitro) can be measured. Such GSK-3 target molecules, for example, GSK-3β target molecules, are well known to those of skill in the art. Glycogen synthase is one example of such a protein. The phosphorylation status of residues phosphorylated by GSK-3 can be surveyed by immunological methods well known to those of skill in the art, for example by using phospho-specific antibodies specifically binding to the phosphorylated or unphosphorylated state of such a target molecule. Another approach is the assessment of biomarkers indicative of GSK-3 activity. Serine 9 phosphorylation of GSK-3β (using the numbering as in NP_002084) is an example of such a biomarker indicating inhibition of GSK-3. Serine 9 of GSK-3β can be phosphorylated by protein kinase B (PKB, AKT), which leads ton inhibition of GSK-3β activity. Other kinases, such as PICA, PKC, MAP kinase, and p90$^{rsk}$ have been indicated in the N-terminal phosphorylation of GSK-3β. The phosphorylation status of serine 9 in GSK-3β can be surveyed by methods well known to those of skill in the art, for example by assays employing phosphor-specific antibodies. It is known to those of skill in the art that the methodology employed for monitoring a specific biomarker will depend on the nature of the biomarker. In general, a suitable sample will be obtained from the subject and processed according to specific assay requirements for any given marker. Most biomarkers, for example the expression of a gene product, the phosphorylation of a specific residue in a protein, the presence or concentration of a metabolite in a body fluid, can be assayed by standard methods well known to those in the related biomedical arts. For example, hybridization based methods such as northern blot, southern blot, microarray assays, etc., can be used to assay nucleic acid biomarkers. Similarly, immunoassay based methods such as western blot, enzyme-linked immunosorbent assay (ELISA), fluorescence activated cell sorting (FACS), immunocytochemistry, isoelectric focusing, etc., can be used to assay many protein and non-protein biomarkers. If the desired state or level of such a biomarker is not observed, the amount of the respective compound can be adjusted until the desired effect is observed. Alternatively, starting from an amount sufficient to effect the desired change in a biomarker, the amount of a compound may be decreased to the minimal amount necessary to effect the desired change in the biomarker. Accordingly, such a biomarker assessment, by itself or in combination with other diagnostic approaches, can be used, according to some aspects of the invention, to determine an effective dosage or amount of the compounds provided by some aspects of this invention.

Depending on the assay employed to survey GSK-3 activity, a quantitative approach might be chosen. A quantitative value relating to GSK-3 activity can be compared to a control or reference value. For example, in a western blot assaying the expression level of GSK-3 or the level of GSK-3β with Serine 9 phosphorylation, the strength of a signal obtained from a protein band may be quantified by densitometry and compared to other signal strength values obtained by densitometry from other bands. Other methods yielding quantifiable results will be obvious to someone of skill in the art. Using assays yielding quantifiable results allows for the quantification of GSK-3 inhibition during and/or after administration of a GSK-3 inhibitor. For example, a sample of a relevant body tissue or body fluid may be taken at various time points before, during, and/or after a GSK-3 inhibitor is administered. Quantitative GSK-3 activity values yielded from assaying such samples may then be compared and correlated to a level of GSK-3 activity in each sample. The activity of GSK-3 in a sample as described herein can be correlated to the activity of GSK-3 in the body fluid or body tissue the sample was taken from. The GSK-3 activity observed in a given sample may also be compared to an appropriate control or reference level. Control or baseline levels can be derived from appropriate control individuals or populations. For example, a control sample might be a sample from a subject before a GSK-3 inhibitor is administered. The GSK-3 activity determined in that sample can be compared with the activity determined in samples taken during and/or after GSK-3 inhibitor administration. An appropriate sample from a healthy individual might also serve as a control. Likewise, an average activity expected or observed in a healthy population might serve as a reference level.

The dose of a GSK-3 inhibitor may be adjusted based on the results from both quantitative and qualitative assays, for example the dose may be increased if no or little GSK-3 inhibition is observed, or decreased if complete or a high level of inhibition is observed until a desired level of GSK-3 activity is achieved. If a GSK-3 inhibitor is administered to a subject having a disease of disorder, then monitoring the state of this disorder in parallel to monitoring the level of GSK-3 inhibition may allow for a correlation of a level of GSK-3 inhibition that is ideal to achieve or maintain a clinically desired result, for example a mood stabilization in a patient with a mood disorder. The dosage of a GSK-3 inhibitor can, accordingly, be fine-tuned using both quantitative and qualitative assays for GSK-3 activity.

In some embodiments, the level of inhibition of GSK-3 activity in the body fluid or tissue or cell type being examined as a result of administering a GSK-3 inhibitor according to this invention is at least about 5%, about 10%, 10-50%, about 20%, about 25%, about 30%, about 40%, about 50%, 50-100%, about 60%, about 70%, about 75%, about 80%, about 85%, about 90%, about 95%, about 97.5%, about 98%, about 99%, about 99.5%, about 99.9% or about 100%. In some embodiments, the body fluid that is examined for GSK-3 activity is blood. In some embodiments the GSK-3 activity is inhibited by more than 50%.

Inhibition of GSK-3, as used herein, refers to a decrease of GSK-3 activity, as measured in any suitable assay. Examples of suitable assays include those described herein and various others known to those of skill in the art.

Adjustment of the dosage of said GSK-3 inhibitor based on the results of assays surveying GSK-3 activity is a powerful tool to fine-tune compound dosage, for example to an amount sufficient to alleviate the symptoms of a disease or disorder in a subject while causing a minimal amount of side-effects.

The sample to be tested for GSK-3 activity can be derived from virtually any source and will depend primarily on the assay employed. The sample may be a bodily fluid or tissue sample from a subject. The term tissue as used herein refers to both localized and disseminated cell populations including but not limited to brain, heart, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea and lung. Body fluids include saliva, sperm, serum, plasma, blood, lymph and urine, but are not so limited. Both invasive and non-invasive techniques can be used to obtain such samples and these are known to those of ordinary skill in the art.

The compounds and/or compositions of the invention are administered to the subject in an effective amount for treating disorders such as neurological diseases and/or psychiatric disorders. An "effective amount", for instance, is an amount necessary or sufficient to realize a desired biologic effect. An effective amount to treat or ameliorate a disease or disorder according to aspects of this invention would be any amount sufficient to effect an amelioration of such a disease.

An "effective amount for inhibiting GSK-3", for instance, could be any amount sufficient to inhibit GSK-3 in a given cell, tissue, cell type, body fluid or sample. Accordingly, an "effective amount for treating Alzheimer's Disease", for instance, could be that amount necessary to (i) prevent further memory loss and/or (ii) arresting or slowing memory loss with respect to memory loss in the absence of the therapy. According to some aspects of the invention, an effective amount is that amount of a compound of the invention alone or in combination with another medicament, which when combined or co-administered or administered alone, results in a therapeutic response to the disease, either in the prevention or the treatment of the disease. The biological effect may be the amelioration and or elimination of symptoms resulting from the disease. In some embodiments, the biological effect is the complete abrogation of the disease, as evidenced for example, by the absence of a symptom of the disease.

The effective amount of a compound of the invention in the treatment of a disease described herein may vary depending upon the specific compound used, the mode of delivery of the compound, and whether it is used alone or in combination. The effective amount for any particular application can also vary depending on such factors as the disease being treated, the particular compound being administered, the size of the subject, or the severity of the disease or condition. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial toxicity and yet is entirely effective to treat the particular subject.

In examining the molecular mechanism by which lithium affects symptoms of neurological diseases and/or psychiatric disorders, it was discovered that upon inhibition of GSK-3 by lithium, the proteasome-mediated degradation of the multifunctional protein β-catenin is blocked, a process sometimes referred to as "n-catenin stabilization". This results in β-catenin accumulation in the cytoplasm and its translocation to the nucleus where it acts as a co-activator of the transcription of TCF/LEF-dependent genes. β-catenin also is known to play an important role in memory consolidation, and GSK-3 signaling inhibits long-term potentiation, a cellular correlate of learning and memory. Recently, the overexpression of β-catenin in the mouse brain has been reported to phenocopy the effect of lithium on dopamine-dependent behavior that is used as a model of mania in Bipolar Disorder. Lithium has been shown to have beneficial effects in the treatment of certain neurodegenerative disorders, including but not limited to Fragile X Syndrome and Alzheimer's Disease. Together, these findings provide evidence for the importance of GSK-3/β-catenin signaling in psychiatric and cognitive disorders.

According to aspects of this invention, a compound that is used to mimic lithium in a therapeutic scenario for neurological disease and/or psychiatric disorder should also exhibit β-catenin stabilizing activity. Some aspects of this invention identify compounds that are GSK-3 inhibitors to also be β-catenin stabilizers, for example, ruboxistaurin, enzastaurin, sunitinib, midostaurin, and Chir99021. Such compounds and methods for their use in the treatment of individuals diagnosed with a neurological disease or psychiatric disorder are provided by some aspects of this invention.

β-catenin is a cytoplasmic protein that is critical for classical cadherin-mediated intercellular adhesion. Inside the cell, a β-catenin/α-catenin complex interacts with the second cytoplasmic domain (CP2) of the classical cadherins. In addition to its role in cell adhesion, β-catenin is also a key component of certain cellular signaling pathways, leading to activation of gene expression and a variety of developmental and disease processes. In particular, β-catenin functions in Wnt-mediated signaling, associating with LEF-1/TCF DNA binding proteins to form a transcription factor (see Willert and Nusse, Genetics and Development 8:95-102, 1998). β-catenin signaling is modulated in a cell by a number of activators and inhibitors. An activator of β-catenin signaling is any agent (e.g. signaling molecule, gene product, chemical compound, etc.) that leads to an activation of β-catenin signaling above the level observed without said agent.

In some embodiments of this invention, a subject to which a compound, for example ruboxistaurin, enzastaurin, sunitinib, midostaurin, lestaurtinib, 7-hydroxystaurosporine, and/or Chir99021 is administered, is suspected and/or indicated or has been diagnosed to have a neurological disease or psychiatric disorder. In some embodiments a compound according to aspects of this invention is administered to a subject based on said subject being indicated or diagnosed to have a neurological disease and/or a psychiatric disorder. In these embodiments, the indication or diagnosis of a neurological disease or psychiatric disorder in a subject is, at least in part, the reason for administering a compound according to aspects of this invention to a subject.

Neurological diseases and psychiatric disorders can be diagnosed and monitored by many clinical assays and procedures well known to those of skill in the relevant medical arts, for example procedures outlined in the International Classification of Diseases and Related Health Problems (ICD, published by the World Health Organization, WHO), or the Diagnostic and Statistical Manual of Mental Disorders (DSM, published by the American Psychiatric Association, APA) and other manuals are widely accepted by mental health professionals. The type of test appropriate for a given disease or disorder will, of course, depend on the disease or disorder to be diagnosed or monitored.

In some embodiments, the motivation for administering a compound according to aspects of this invention is an intention to treat a neurological disease or psychiatric disorder in a subject.

The term "neurological disease", as used herein, refers to a condition having as a component a central or peripheral nervous system malfunction. A neurological disease may cause a disturbance in the structure or function of the nervous system resulting from developmental abnormalities, disease, genetic defects, injury or toxin. These disorders may affect the central nervous system (e.g., the brain, brainstem and cerebellum), the peripheral nervous system (e.g., the cranial nerves, spinal nerves, and sympathetic and parasympathetic nervous systems) and/or the autonomic nervous system (e.g., the part of the nervous system that regulates involuntary action and that is divided into the sympathetic and parasympathetic nervous systems). Accordingly, a neurodegenerative disease is an example for a neurological disease.

As used herein, the term "neurodegenerative disease" refers to a condition characterized by loss of neuronal cells or neuronal cell supporting cells causing cognitive and/or motoric dysfunction and/or disabilities. Accordingly, the term refers to any disease or disorder that might be reversed, deterred, managed, treated, improved, or eliminated with agents that stimulate the generation of new neurons. Examples of neurodegenerative diseases include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's Disease, Fragile X Syndrome, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden-Spatz disease, dementia pugilistica, AIDS Dementia, age related dementia, age associated memory impairment, and amyloidosis-related neurodegenerative diseases such as those caused by the prion protein (PrP) which is associated with transmissible spongiform encephalopathy (Creutzfeldt-Jakob disease, Gerstmann-Straussler-Scheinker syndrome, scrapic, and kuru), and those caused by excess cystatin C accumulation (hereditary cystatin C angiopathy); and (ii) acute neurodegenerative disorders such as traumatic brain injury (e.g., surgery-related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor) and Wernicke-Korsakoff's related dementia. Neurodegenerative diseases affecting sensory neurons include Friedreich's ataxia and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Rett syndrome. The foregoing examples are not meant to be comprehensive but serve merely as an illustration of the term "neurodegenerative disorder".

Alzheimer's Disease is a degenerative brain disorder characterized by cognitive and noncognitive psychiatric symptoms. Psychiatric symptoms are common in Alzheimer's Disease, with psychosis (hallucinations and delusions) present in approximately fifty percent of affected patients. Similar to Schizophrenia, positive psychotic symptoms are common in Alzheimer's Disease. Delusions typically occur more frequently than hallucinations. Alzheimer's patients may also exhibit negative symptoms, such as disengagement, apathy, diminished emotional responsiveness, loss of volition, and decreased initiative. Indeed, antipsychotic compounds that are used to relieve psychosis of Schizophrenia are also useful in alleviating psychosis in Alzheimer's patients. As used herein, the term "dementia" refers to the loss of cognitive and intellectual functions without impairment of perception or consciousness. Dementia is typically characterized by disorientation, impaired memory, judgment, and intellect, and a shallow labile affect.

Fragile X Syndrome, or Martin-Bell Syndrome, is a genetic syndrome, which results in a spectrum of characteristic physical, intellectual, emotional and behavioral features which range from severe to mild in manifestation. The syndrome is associated with the expansion of a single trinucleotide gene sequence (CGG) on the X chromosome, and results in a failure to express the FMR-1 protein which is required for normal neural development. There are four generally accepted forms of Fragile X Syndrome which relate to the length of the repeated CGG sequence; Normal (29-31 CGG repeats), Premutation (55-200 CGG repeats), Full Mutation (more than 200 CGG repeats), and Intermediate or Gray Zone Alleles (40-60 repeats). Normally, the FMR1 gene contains between 6 and 55 repeats of the CGG codon (trinucleotide repeats). In people with the Fragile X Syndrome, the FMR1 allele has over 230 repeats of this codon. Expansion of the CGG repeating codon to such a degree results in a methylation of that portion of the DNA, effectively silencing the expression of the FMR1 protein. This methylation of the FMR1 locus in chromosome band Xq27.3 is believed to result in constriction of the X chromosome which appears 'fragile' under the microscope at that point, a phenomenon that gave the syndrome its name. Mutation of the FMR1 gene leads to the transcriptional silencing of the fragile X-mental retardation protein, FMRP. In normal individuals, FMRP is believed to regulate a substantial population of mRNA: FMRP plays important roles in learning and memory, and also appears to be involved in development of axons, formation of synapses, and the wiring and development of neural circuits.

Amyotrophic lateral sclerosis (ALS), also called Lou Gehrig's disease, is a progressive, fatal neurological disease. ALS occurs when specific nerve cells in the brain and spinal cord that control voluntary movement gradually degenerate and causes the muscles under their control to weaken and waste away, leading to paralysis. Currently, there is no cure for ALS; nor is there a proven therapy that will prevent or reverse the course of the disorder.

Parkinson's disease is a disturbance of voluntary movement in which muscles become stiff and sluggish. Symptoms of the disease include difficult and uncontrollable rhythmic twitching of groups of muscles that produces shaking or tremors. The disease is caused by degeneration of pre-synaptic dopaminergic neurons in the brain and specifically in the brain stem. As a result of the degeneration, an inadequate release of the chemical transmitter dopamine occurs during neuronal activity. Currently, Parkinson's disease is treated with several different compounds and combinations. Levodopa (L-dopa), which is converted into dopamine in the brain, is often given to restore muscle control. Perindopril, an ACE inhibitor that crosses the blood-brain barrier, is used to improve patients' motor responses to L-dopa. Carbidopa is administered with L-dopa in order to delay the conversion of L-dopa to dopamine until it reaches the brain, and it also lessens the side effects of L-dopa. Other drugs used in Parkinson's disease treatment include dopamine mimicers Mirapex (pramipexole dihydrochloride) and Requip (ropinirole hydrochloride), and Tasmar (tolcapone), a COMT inhibitor that blocks a key enzyme responsible for breaking down levodopa before it reaches the brain.

The term "psychiatric disorder", as used herein, refers to a condition or disorder relating to the functioning of the brain and the cognitive processes or behavior. Psychiatric disorders may be further classified based on the type of neurological disturbance affecting the mental faculties. Psychiatric disorders are expressed primarily in abnormalities of thought, feeling and/or behavior producing either distress or impairment of function (for example, impairment of mental function such with dementia or senility). The term "psychiatric disorder" is, accordingly, sometimes used interchangeably with the term "mental diorder" or the term "mental illness".

A psychiatric disorder is often characterized by a psychological or behavioral pattern that occurs in an individual and is thought to cause distress or disability that is not expected as part of normal development or culture. Definitions, assessments, and classifications of mental disorders can vary, but guideline criteria listed in the International Classification of Diseases and Related Health Problems (ICD, published by the World Health Organization, WHO), or the Diagnostic and Statistical Manual of Mental Disorders (DSM, published by the American Psychiatric Association, APA) and other manuals are widely accepted by mental health professionals. Individuals may be evaluated for various psychiatric disorders using criteria set forth in these and other publications accepted by medical practitioners in the field and the manifestation and severity of a psychiatric disorder may be determined in an individual using these publications.

Categories of diagnoses in these schemes may include dissociative disorders, mood disorders, anxiety disorders, psychotic disorders, eating disorders, developmental disorders, personality disorders, and other categories. There are different categories of mental disorder, and many different facets of human behavior and personality that can become disordered.

One group of psychiatric disorders includes disorders of thinking and cognition, such as Schizophrenia and delirium. A second group of psychiatric disorders includes disorders of mood, such as affective disorders and anxiety. A third group of psychiatric disorders includes disorders of social behavior, such as character defects and personality disorders. And a fourth group of psychiatric disorders includes disorders of learning, memory, and intelligence, such as mental retardation and dementia. Accordingly, psychiatric disorders encompass Schizophrenia, delirium, attention deficit disorder (ADD), schizoaffective disorder, Depression, mania, attention deficit disorders, drug addiction, dementia, agitation, apathy, anxiety, psychoses, personality disorders, Bipolar Disorders, unipolar affective disorder, obsessive-compulsive disorders, eating disorders, post-traumatic stress disorders, irritability, adolescent conduct disorder and disinhibition.

Some diseases classified as neurodegenerative diseases, for example Alzheimer's Disease, also sometimes show aspects of psychiatric disorders as listed herein, for example disorders of memory or dementia. Some neurodegenerative diseases or manifestations thereof can, accordingly, also be referred to as psychiatric disorders. These terms are, therefore, not mutually exclusive.

The state of anxiety or fear can become disordered, so that it is unusually intense or generalized over a prolonged period of time. Commonly recognized categories of anxiety disorders include specific phobia, Generalized Anxiety Disorder, Social Anxiety Disorder, Panic Disorder, Agoraphobia, Obsessive-Compulsive Disorder, Post-Traumatic Stress Disorder.

Relatively long lasting affective states can also become disordered. Mood disorder involving unusually intense and sustained sadness, melancholia or despair is known as clinical Depression (or major Depression), and may more generally be described as emotional dysregulation. Milder but prolonged Depression can be diagnosed as dysthymia. Bipolar Disorder involves abnormally "high" or pressured mood states, known as mania or hypomania, alternating with normal or depressed mood.

Patterns of belief, language use and perception can become disordered. Psychotic disorders centrally involving this domain include Schizophrenia and Delusional Disorder. Schizoaffective Disorder is a category used for individuals showing aspects of both Schizophrenia and affective disorders. Schizotypy is a category used for individuals showing some of the traits associated with Schizophrenia but without meeting cut-off criteria.

The fundamental characteristics of a person that influence his or her cognitions, motivations, and behaviors across situations and time—can be seen as disordered due to being abnormally rigid and maladaptive. Categorical schemes list a number of different personality disorders, such as those classed as eccentric (e.g., Paranoid personality disorder, Schizoid personality disorder, Schizotypal personality disorder), those described as dramatic or emotional (Antisocial personality disorder, Borderline personality disorder, Histrionic personality disorder, Narcissistic personality disorder) or those seen as fear-related (Avoidant personality disorder, Dependent personality disorder, Obsessive-compulsive personality disorder).

Other disorders may involve other attributes of human functioning. Eating practices can be disordered, with either compulsive over-eating or under-eating or binging. Categories of disorder in this area include Anorexia nervosa, Bulimia nervosa, Exercise Bulimia or Binge eating disorder. Sleep disorders such as Insomnia also exist and can disrupt normal sleep patterns. Sexual and gender identity disorders, such as Dyspareunia or Gender identity disorder or ego-dystonic homosexuality. People who are abnormally unable to resist urges, or impulses, to perform acts that could be harmful to themselves or others, may be classed as having an impulse control disorder, including various kinds of Tic disorders such as Tourette's Syndrome, and disorders such as Kleptomania (stealing) or Pyromania (fire-setting). Substance-use disorders include Substance abuse disorder. Addictive gambling may be classed as a disorder. Inability to sufficiently adjust to life circumstances may be classed as an Adjustment disorder. The category of Adjustment disorder is usually reserved for problems beginning within three months of the event or situation and ending within six months after the stressor stops or is eliminated. People who suffer severe disturbances of their self-identity, memory and general awareness of themselves and their surroundings may be classed as having a Dissociative identity disorder, such as Depersonalization disorder (which has also been called multiple personality disorder, or "split personality"). Factitious disorders, such as Munchausen syndrome, also exist where symptoms are experienced and/or reported for personal gain.

Disorders appearing to originate in the body, but thought to be mental, are known as somatoform disorders, including Somatization disorder. There are also disorders of the perception of the body, including Body dysmorphic disorder. Neurasthenia is a category involving somatic complaints as well as fatigue and low spirits/Depression, which is officially recognized by the ICD (version 10) but not by the DSM (version IV). Memory or cognitive disorders, such as amnesia or Alzheimer's Disease are also sometimes classified as psychiatric disorders.

Other proposed disorders include: Self-defeating personality disorder, Sadistic personality disorder, Passive-aggressive personality disorder, Premenstrual dysphoric disorder, Video game addiction or Internet addiction disorder.

Bipolar Disorder is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and Depression are present at the same time. These episodes are usually separated by periods of "normal" mood, but in some individuals, Depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum.

Autism (also referred to as Autism Spectrum Disorder, or ASD) is a disorder that seriously impairs the functioning of individuals. It is characterized by self-absorption, a reduced ability to communicate with or respond to the outside world, rituals and compulsive phenomena, and mental retardation. Autistic individuals are also at increased risk of developing seizure disorders, such as epilepsy. While the actual cause of Autism is unknown, it appears to include one or more genetic factors, as indicated by the fact that the concordance rate is higher in monozygotic twins than in dizygotic twins, and may also involve immune and environmental factors, such as diet, toxic chemicals and infections.

Schizophrenia is a disorder that affects about one percent of the world population. Three general symptoms of Schizophrenia are often referred to as positive symptoms, negative symptoms, and disorganized symptoms. Positive symptoms can include delusions (abnormal beliefs), hallucinations (abnormal perceptions), and disorganized thinking. The hallucinations of Schizophrenia can be auditory, visual, olfactory, or tactile. Disorganized thinking can manifest itself in schizophrenic patients by disjointed speech and the inability to maintain logical thought processes. Negative symptoms can represent the absence of normal behavior. Negative symptoms include emotional flatness or lack of expression and can be characterized by social withdrawal, reduced energy, reduced motivation, and reduced activity. Catatonia can also be associated with negative symptoms of Schizophrenia. The symptoms of Schizophrenia should continuously persist for a duration of about six months in order for the patient to be diagnosed as schizophrenic. Based on the types of symptoms a patient reveals, Schizophrenia can be categorized into subtypes including catatonic Schizophrenia, paranoid Schizophrenia, and disorganized Schizophrenia.

Examples of antipsychotic drugs that may be used to treat schizophrenic patients include phenothizines, such as chlorpromazine and trifluopromazine; thioxanthenes, such as chlorprothixene; fluphenazine; butyropenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these compounds may relieve the symptoms of Schizophrenia, their administration can result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech and agranulocytosis.

Mood disorders are typically characterized by pervasive, prolonged, and disabling exaggerations of mood and affect that are associated with behavioral, physiologic, cognitive, neurochemical and psychomotor dysfunctions. The major mood disorders include, but are not limited to major depressive disorder (also known as unipolar disorder), Bipolar Disorder (also known as manic depressive illness or bipolar Depression), dysthymic disorder.

The term "Depression", sometimes used interchangeably with "depressive disorder" and refers to mood disorders manifesting in morbid sadness, dejection, or melancholy. Depressive disorders can involve serotonergic and noradrenergic neuronal systems based on current therapeutic regimes that target serotonin and noradrenalin receptors. Mania may result from an imbalance in certain chemical messengers within the brain. Administering phosphotidyl choline has been reported to alleviate the symptoms of mania.

Mania is a sustained form of euphoria that affects millions of people in the United States who suffer from Depression. Manic episodes can be characterized by an elevated, expansive, or irritable mood lasting several days, and is often accompanied by other symptoms, such as, over-activity, over-talkativeness, social intrusiveness, increased energy, pressure of ideas, grandiosity, distractibility, decreased need for sleep, and recklessness. Manic patients can also experience delusions and hallucinations.

Anxiety disorders are characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating). Benzodiazepines, which enhance the inhibitory effects of the gamma aminobutyric acid (GABA) type A receptor, are frequently used to treat anxiety. Buspirone is another effective anxiety treatment.

Schizo-affective disorder describes a condition where both the symptoms of a mood disorder and Schizophrenia are present. A person may manifest impairments in the perception or expression of reality, most commonly in the form of auditory hallucinations, paranoid or bizarre delusions or disorganized speech and thinking, as well as discrete manic and/or depressive episodes in the context of significant social or occupational dysfunction.

As used herein, the term "subject" refers to an individual, for example a human, non-human primate, cow, horse, pig, sheep, goat, dog, cat, rodent, or other mammal.

As used herein, the term "a subject being indicated or diagnosed" to have a disease or disorder refers to a subject who has been clinically diagnosed to have a disease or disorder, shows any symptom commonly associated with a disease or disorder, and/or is suspected to have a disease or disorder. In the context of neurological disease and/or psychiatric disorder, a diagnosis is generally based on an assessment of the subject by a trained professional, for example a clinical doctor or a psychiatrist. A diagnosis can be based on a person's, for example a clinician's or psychiatrist's, personal experience, and/or a self-diagnosis by a patient, or the results of any test or procedure according to standard criteria, for example such as described in the Diagnostic and Statistical Manual of Mental Disorders (DSM, published by the American Psychiatric Association, APA) or other manuals and tests widely accepted by mental health professionals.

The terms "treating", "to treat", "treatment" and "therapy" refer to any intervention with an intent to induce an improvement of the state of a disease, disorder or condition in a subject, for example, a beneficial or desired clinical result. Alleviation of symptoms, diminishment of extent of disease or disorder, stabilized (e.g., not worsening) state of disease or disorder, delay or slowing of disease or disorder progression, amelioration or palliation of the disease state, and remission (whether partial or total), whether detectable or undetectable, prevention of a disease or of complications associated with a disease, are examples of beneficial or desired clinical results. One of skill in the art realizes that a treatment may improve the state of a disease, disorder or condition, but may not be a complete cure for the disease. Accordingly, an example of treating a subject diagnosed with Bipolar Disorder could be administering a compound according to aspects of this invention to such a subject with an intent to stabilize the mood of the subject, no matter whether the intended mood stabilization actually manifests or not. A treatment may address the state of a disease, disorder or condition as a whole, for example leading to the complete remission of all symptoms of a given disease, e.g. Bipolar Disorder. Alternatively, a treatment may only address a certain aspect or certain aspects of a disease, disorder or condition. For example the administration of a compound improving cognitive function in a subject having Alzheimer's Disease with or without affecting other aspects of the disease (e.g. Depression, anxiety, personality disintegration) would be an example for a treatment.

The terms "treatment", "to treat", "treating" or "therapy" are intended to include one or more of prophylaxis, amelioration, prevention or cure of a disease, disorder or condition (e.g., a neurodegenerative disease (e.g., Alzheimer's Disease Fragile X Syndrome or ALS) or a psychiatric disorder (e.g., Bipolar Disorder, Schizophrenia, Autism or Depression)). Treatment after a disease, disorder or condition (e.g., a neurodegenerative disease (e.g., Alzheimer's Disease Fragile X Syndrome or ALS) or a psychiatric disorder (e.g., Bipolar Disorder, Schizophrenia, Autism or Depression)) has been diagnosed or clinically manifested aims to reduce, ameliorate or altogether eliminate the condition, and/or its associated symptoms, or prevent it from becoming worse. Treatment before a disease, disorder or condition (e.g., a neurodegenerative disease (e.g., Alzheimer's Disease Fragile X Syndrome or ALS) or a psychiatric disorder (e.g., Bipolar Disorder, Schizophrenia, Autism or Depression)) has been diagnosed or clinically manifested (e.g., prophylactic treatment) aims to reduce the risk of developing the condition and/or lessen its severity if the condition does develop. As used herein, the terms "prevention" or "prevent" refers to the prophylactic treatment of a subject who is at risk of developing a disease, disorder, or condition (e.g., a neurodegenerative disease (e.g., Alzheimer's Disease Fragile X Syndrome or ALS) or a psychiatric disorder (e.g., Bipolar Disorder, Schizophrenia, Autism or Depression)) resulting in a decrease in the probability that the subject will develop the disorder, and to the inhibition of further development of an already established disorder.

As used herein, a treatment may be prophylactic and/or therapeutic. In some embodiments, a treatment may include preventing disease development or progression. In certain embodiments, a treatment may include inhibiting and or reducing the rate of disease development or progression. It should be appreciated that the terms preventing and/or inhibiting may be used to refer to a partial prevention and/or inhibition (e.g., a percentage reduction, for example about 5%, about 10%, about 20%, about 30%, about 40%, about 50%, about 60%, about 70%, about 80%, about 90%, or higher or lower or intermediate percentages of reduction). However, in some embodiments, a prevention or inhibition may be complete (e.g., a 100% reduction or about a 100% reduction based on an assay or an expected progression). Criteria useful for the quantification of disease and disorder states and, thus, in assessing the effect of a treatment on symptoms associated with neurological diseases and psychiatric disorders, such as the Hamilton rating scale for depression and the criteria developed by the MATRICS initiative (measurement and treatment to improve cognition in schizophrenia), are well known to those in the relevant medical arts. Many of such quantitative criteria relating to neurological disease or psychiatric disorder have been published, for example, in the DSM.

Some of the compounds related to by aspects of this invention have been suggested for the treatment of a subject having diseases other than neurological diseases and/or psychiatric disorders. Examples of such diseases are diabetes and some of its complications, like diabetic peripheral neuropathy, diabetic nephropathy, diabetic retinopathy, macular edema, and neoplastic malignancies, including many forms of cancer (e.g. prostate cancer, brain cancer (e.g. glioblastoma), stomach and renal cancer, and some types of blood cancer (e.g. myeloproliferative disorders, anaplastic large cell or mature T-cell lymphoma)). Aspects of this invention relate to the use of such compounds for the treatment of individuals having neurological disease or psychiatric disorder manifestations, for which the compounds according to aspects of this invention have not been indicated, demonstrated, and/or suggested thus far. Accordingly, some aspects of this invention provide methods of using ruboxistaurin, enzastaurin, sunitinib, midostaurin, lestaurtinib and/or 7-hydroxystaurosporine in the treatment of subjects having a neurological disease and/or psychiatric disorder as described herein, for which the respective compound has not been implicated, indicated, demonstrated, and/or suggested before.

Some of the diseases that have been suggested to be treated with some of the compounds this invention relates to, are described in more detail below.

Diabetes is a chronic metabolic disorder which includes a severe form of childhood diabetes (also called juvenile, Type I or insulin-dependent diabetes). Type II Diabetes (DM II) is generally found in adults. Diabetes is a complex disease characterized by a perturbation of normal glucose metabolism and/or glucose regulation.

"Normal" in this context of glucose metabolism and/or glucose regulation refers to a state found in a healthy (e.g. non-diabetic) individual or population. The terms "glucose metabolism" and "glucose regulation" refer to cellular glucose uptake, insulin secretion, for example by pancreatic cells, and/or insulin response, for example by muscle cells, liver cells, or adipocytes. The term "normal glucose metabolism" or "normal glucose regulation", accordingly, refer to the state typically found and/or expected in a healthy individual and/or a state representative of the average state found in a healthy population. Standardized assays, such as the fasting plasma glucose test (FPGT) or oral glucose tolerance test (OGTT) as well as benchmark values for the evaluation of glucose metabolism and regulation are well known to those of skill in the relevant medical arts. For example, currently the American Diabetes Association (ADA) suggests that a value of less than 100 mg/dl in the FPGT and/or less than 140 mg/dl in the OGTT are indicative of normal glucose metabolism and/or glucose regulation.

In diabetic patients one or more aspects of glucose metabolism are perturbed, for example cellular resistance to insulin may lead to elevated blood glucose levels, a characteristic of diabetic patients. Patients with diabetes of all types have a high incidence of diabetic complications, for example diabetic peripheral neuropathy, diabetic retinopathy, and/or diabetic nephropathy and considerable morbidity and mortality from microvascular (retinopathy, neuropathy, nephropathy) and macrovascular (heart attacks, stroke, peripheral vascular disease) pathology.

Diabetes is the leading known cause of neuropathy in developed countries, and neuropathy is the most common complication and greatest source of morbidity and mortality in diabetes patients. It is estimated that the prevalence of neuropathy in diabetes patients is approximately 20%. Diabetic neuropathy is implicated in 50-75% of nontraumatic amputations. Diabetic peripheral neuropathy can affect any peripheral nerve. Accordingly, it can affect all organs and systems that are innervated by peripheral nerves. The clinical manifestation or syndrome of diabetic peripheral neuropathy depends on the affected organ, organ system, or body part.

Diabetic retinopathy is the most common diabetic complication affecting the eyes and a leading cause of blindness in American adults. It is caused by changes in the blood vessels of the retina. Diabetic retinopathy can manifest as a swelling and leaking of the blood vessels of the eye and/or abnormal growth of blood vessels on the surface of the retina. The retina is the light-sensitive tissue at the back of the eye. A healthy retina is necessary for good vision and the function of the retina is impaired in patients with diabetic retinopathy. This condition can gradually worsen over time and cause partial or complete loss of vision. Four stages of diabetic retinopathy are known to those skilled in the art: mild nonproliferative retinopathy, moderate nonproliferative retinopathy, severe nonproliferative retinopathy, and proliferative retinopathy.

Diabetic nephropathy, also known as Kimmelstiel-Wilson syndrome and intercapillary glomerulonephritis, is a progressive kidney disease caused by angiopathy of capillaries in the kidney glomeruli as a result of longstanding diabetes. It is characterized by nephrotic syndrome and nodular glomerulosclerosis. The clinical manifestation is generally a loss, partial or complete, of kidney function.

Non-insulin dependent diabetes mellitus develops especially in subjects with insulin resistance and a cluster of cardiovascular risk factors such as obesity, hypertension and dyslipidemia, a syndrome which first recently has been recognized and is named "metabolic syndrome".

Antidiabetic agents, include insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; protein tyrosine phosphatase-1 B (PTP-1 B) inhibitors such as PTP-112; GSK-3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237; b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin; c) anti-obesity agents such as orlistat; and) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The term "neoplastic malignancies" refers to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not.

Prostate cancer is one of the most common tumors diagnosed among men. Despite advances in screening and early detection, approximately 30% of patients undergoing definitive prostatectomy or ablative radiation therapy will have recurrent disease at 10 years. The term "prostate cancer" as used herein includes both hormone responsive, as well as hormone refractory prostate cancer, as well as benign prostate hypertrophic conditions.

Glioblastoma multiforme (GBM) is the most common and most aggressive type of primary brain tumor, accounting for 52% of all primary brain tumor cases and 20% of all intracranial tumors. Despite being the most prevalent form of primary brain tumor, GBMs occur in only 2-3 cases per 100,000 people in Europe and North America. The standard WHO-2007 name for this brain tumor is "Glioblastoma".

Aspects of this invention also relate to compositions comprising a compound according to this invention. Pharmaceutical compositions of the present invention comprise an effective amount of a compound according to this invention, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated.

Some aspects of this invention provide methods for administering any of the compounds or compositions described herein based on a subject being indicated or diagnosed to have a neurological disease or a psychiatric disorder. A composition may comprise different types of carriers depending on whether it is to be administered in solid, liquid or aerosol form, and whether it need to be sterile for such routes of administration as injection. A compound or composition as provided herein can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference). In a particular embodiment, intraperitoneal injection is contemplated.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Effective and sub-effective dosages of the therapeutic agents provided herein are well known to those in the art. Exemplary effective doses for some of the compounds are given in FIGS. 2-7 and are also provided in the Examples. Exemplary effective doses of Chir99021 are known to those of skill in the art, provided in the Examples, and can be adapted to a given patient and/or disease by those of skill in the relevant arts using no more than routine experimentation. For example, in some embodiments, an effective dose of Chir 99021 is a dose that achieves a serum concentration of Chir99021 of about 750 µM, about 500 µM, about 250 µM, about 200 µM, about 100 µM, about 90 µM, about 80 µM, about 75 µM, about 70 µM, about 60 µM, about 50 µM, about 40 µM, about 30 µM, about 25 µM, about 20 µM, about 15 µM, or about 10 µM.

Effective and sub-effective dosages of additional compounds indicated in the treatment of neurological diseases or psychological disorders are also well known in the art. For example, it is known in the art that the minimal effective dose of lithium in the treatment of a psychological disease, for example, bipolar disorder, is a dose that achieves a serum lithium level of about 0.4 mM. It is further known in the art that the most beneficial dose of lithium in the treatment of a psychological disease, for example, bipolar disorder, is a dose that achieves a serum lithium level of between about 0.6 mM to about 1.2 mM, and preferably between about 0.6 to about 0.75 mM. Methods of determining serum levels of lithium and methods of adjusting the dosage of lithium administered to achieve a desired serum level of lithium are well known to those of skill in the art (see, e.g., Severus W E, Kleindienst N, Seemuller F, Frangou S, Möller H J, Greil W., *What is the optimal serum lithium level in the long-term treatment of bipolar disorder? Results from an empirical study*. Bipolar Disord. 2008 March; 10(2):231-7, incorporated herein in its entirety by reference).

In some embodiments, a sub-effective dose of a GSK-3 inhibitor as provided herein is administered in combination with a sub-effective dose of an additional compound indicated in the treatment of a neurological disease or psychological disorder. In some embodiments, a sub-effective dose of a GSk-3 inhibitor, for example, of Chir99021 is a dose achieving a serum level of less than about 5 µM, about 4 µM, about 30 µM, about 2 µM, about 1 µM, about 0.5 µM, about 0.4 µM, about 0.3 µM, about 0.2 µM, about 0.1 µM, or about 0.05 µM. In some embodiments, a sub-effective dose of an additional compound indicated in the treatment of a neurological disease or psychological disorder, for example, lithium (e.g. administered as lithium chloride or lithium carbonate) is a dose achieving a serum level of less than about 0.6 mM, less than about 0.5 mM, less than about 0.4 mM, less than about 0.3 mM, less than about 0.2 mM, less than about 0.1 mM, or less than about. 0.05 mM.

Multiple doses of the compounds of the invention are also contemplated. In some instances, when a compound of the invention is administere'd with another medicament, such as a mood stabilizer, for example lithium, a sub-therapeutic dosage of either the compound or the mood stabilizer, or a sub-therapeutic dosage of both, is used in the treatment of a subject having, or at risk of developing a neurological disease or a psychiatric disorder. When a plurality of compounds are used together, either one, some or all of them may be administered in a sub-therapeutic dose to produce a desirable therapeutic result. A "sub-therapeutic dose" as used herein refers to a dosage, which is less than that dosage which would produce a therapeutic result in the subject if administered in the absence of the other compound or compounds. Thus, the sub-therapeutic dose of a compound is one which would not produce the desired therapeutic result in the subject in the absence of the administration of the molecules of the invention. Therapeutic doses of compounds that are in clinical use are well known in the field of medicine. These dosages have been extensively described in references such as Remington's Pharmaceutical Sciences, 18th ed., 1990; as well as many other medical references relied upon by the medical profession as guidance for the treatment of neurological disorders.

In some embodiments, a composition comprising a compound or a combination of compounds, as provided by aspects of this invention, may further comprise an antioxidant to retard oxidation of one or more component. Additionally, the prevention of the action of microorganisms can be brought about by a preservative such as an antibacterial and antifungal agent, including but not limited to parabens (e.g., methylparabens, propylparabens), chlorobutanol, phenol, sorbic acid, thimerosal or combinations thereof.

The compounds of the invention may be derivatized in various ways. As used herein "derivatives" of the compounds (such as those of FIGS. 2-8) include salts (e.g. pharmaceutically acceptable salts), any complexes (e.g. inclusion complexes or clathrates with compounds such as cyclodextrins, or coordination complexes with metal ions such as $Mn^{2+}$ and $Zn^{2+}$), esters such as in vivo hydrolysable esters, free acids or bases, polymorphic forms of the compounds, solvates (e.g. hydrates), prodrugs or lipids, coupling partners and protecting groups. By "prodrugs" is meant for example any compound that is converted in vivo into a biologically active compound.

The term "pharmaceutically-acceptable salts" in this respect refers to the relatively non-toxic, inorganic or organic acid addition salts of agents of the present invention. These salts can be prepared in situ in the administration vehicle or the dosage form manufacturing process, or by separately reacting a purified agent of the invention with a suitable organic or inorganic acid, and isolating the salt thus formed during subsequent purification. Representative salts include the bromide, chloride, sulfate, bisulfate, phosphate, phosphonate, nitrate, acetate, valerate, oleate, palmitate, stearate, laurate, benzoate, lactate, tosylate, citrate, maleate, fumarate, succinate, tartrate, napthylate, mesylate, glucoheptonate, lactobionate, and laurylsulphonate salts and the like. See, for example, Berge et al. (1977) J. Pharm. Sci. 66:1-19.

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

As set out herein, certain embodiments of the present compounds (such as those of FIGS. 2-8) may contain a basic functional group, such as amino or alkylamino, and are, thus, capable of forming pharmaceutically-acceptable salts with pharmaceutically-acceptable acids. The term "pharmaceutically-acceptable salts" in this respect refers to the relatively non-toxic, inorganic or organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, phosphonate, nitrate, acetate, valerate, oleate, palmitate, stearate, laurate, benzoate, lactate, tosylate, citrate, maleate, fumarate, succinate, tartrate, napthylate, mesylate, glucoheptonate, lactobionate, and laurylsulphonate salts and the like. See, for example, Berge et al. (1977) J. Pharm. Sci. 66:1-19.

The pharmaceutically acceptable salts of the subject compounds (such as those of FIGS. 2-8) include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention (such as those of FIGS. 2-8) may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al. (1977) J. Pharm. Sci. 66:1-19.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be advisable to include isotonic agents, such as, for example, sugars, sodium chloride or combinations thereof.

A variety of administration routes are available. The particular mode selected will depend, of course, upon the particular compound selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Examples of modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The compounds of the invention can be administered by any ordinary route for administering medications. Depending upon the type of cancer to be treated, compounds of the invention may be inhaled, ingested or administered by systemic routes. Systemic routes include oral and parenteral. Inhaled medications are employed in some embodiments because of the direct delivery to the lung, particularly in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Examples of routes of administration include but are not limited to oral, parenteral, intramuscular, intranasal, intratracheal, intrathecal, intravenous, inhalation, ocular, vaginal, and rectal. For use in therapy, an effective amount of the compounds of the invention can be administered to a subject by any mode that delivers the nucleic acid to the affected organ or tissue. "Administering" the pharmaceutical composition of the present invention may be accomplished by any means known to the skilled artisan.

According to the methods provided by aspects of the invention, the compound may be administered in a pharmaceutical composition. In some embodiments, a pharmaceutical composition comprises a compound provided by aspects of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier refers to a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds provided by aspects of the invention may be formulated into preparations in solid, semi-solid, liquid or gaseous forms such as tablets, capsules, powders, granules, ointments, solutions, depositories, inhalants and injections, and usual ways for oral, parenteral or surgical administration. Some aspects of the invention also embrace pharmaceutical compositions which are formulated for local administration, such as by implants.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

In some embodiments, a compound provided by some aspects of the invention may be administered directly to a tissue. Direct tissue administration may be achieved by direct injection. A compound may be administered once, or alternatively may be administered in a plurality of administrations. If administered multiple times, a compound may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils.

Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In some embodiments, the vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application serial no. 213,668, filed Mar. 15, 1994). PCT/US/0307 describes a biocompatible, and/or biodegradable polymeric matrix for containing a biological macromolecule. The polymeric matrix may be used to achieve sustained release of a compound in a subject. In accordance with one aspect of the instant invention, the compounds described herein may be encapsulated or dispersed within the biocompatible, and/or biodegradable polymeric matrix disclosed in PCT/US/03307. The polymeric matrix may be in the form of a microparticle such as a microsphere (wherein a compound is dispersed throughout a solid polymeric matrix) or a microcapsule (wherein a compound is stored in the core of a polymeric shell). Other forms of the polymeric matrix for containing a compound include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver a compound of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, compounds of the invention may be delivered using the bioerodible implant by way of diffusion, and/or by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the compound, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic diseases. Long-term release, as used herein, means that the implant is constructed and arranged to deliver therapeutic levels of the active ingredient for at least 30 days, and/or at least 60 days. Long-term sustained release implants are well-known to those of ordinary skill in the art and include some of the release systems described above.

Therapeutic formulations useful in the invention may be prepared for storage by mixing a peptide or other molecule having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Some compounds described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include a compound as described herein, along with instructions describing the intended therapeutic application and the proper administration. In certain embodiments a compound in a kit may be in a pharmaceutical formulation and dosage suitable for a particular application and for a method of administration.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing a compound as described herein. The compound may be in the form of a liquid, gel or solid (powder). It may be prepared sterilely, packaged in syringe and shipped refrigerated. Alternatively it may be housed in a vial or other container for storage. A second container may have other agents prepared sterilely. Alternatively the kit may include a compound premixed and shipped in a syringe, vial, tube, or other container. The kit may have one or more or all of the components required to administer a compound according to this invention to a patient, such as a syringe, topical application devices, or iv needle tubing and bag.

The kit may have a variety of forms; such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

Several methods are disclosed herein of administering a subject with a compound for the treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition, disease or disorder.

For reference, examples of the nucleotide and amino acid sequences of human GSK3 isoforms are given below:

```
GSK-3α mRNA, nucleotide sequence (SEQ ID No: 1):
(>gi|49574531|ref|NM_019884.2|Homo sapiens glyco-
gen synthase kinase 3 alpha (GSK3A), mRNA)
CCCAAGCCAGAGCGGCGCGGCCTGGAAGAGGCCAGGGCCCGGGGGAGGCG

GCGGCAGCGGCGGCGGCTGGGGCAGCCCGGGCAGCCCGAGCCCCGCAGCC

TGGGCCTGTGCTCGGCGCCATGAGCGGCGGCGGGCCTTCGGGAGGCGGCC

CTGGGGGCTCGGGCAGGGCGCGGACTAGCTCGTTCGCGGAGCCCGGCGGC

GGAGGCGGAGGAGGCGGCGGCGGCCCCGGAGGCTCGGCCTCCGGCCCAGG

CGGCACCGGCGGCGGAAAGGCATCTGTCGGGGCCATGGGTGGGGCGTCG

GGGCCTCGAGCTCCGGGGGTGGACCCGGCGGCAGCGGCGGAGGAGGCAGC

GGAGGCCCCGGCGCAGGCACTAGCTTCCCGCCGCCCGGGGTGAAGCTGGG

CCGTGACAGCGGGAAGGTGACCACAGTCGTAGCCACTCTAGGCCAAGGCC

CAGAGCGCTCCCAAGAAGTGGCTTACACGGACATCAAAGTGATTGGCAAT
```

GGCTCATTTGGGGTCGTGTACCAGGCACGGCTGGCAGAGACCAGGGAACT
AGTCGCCATCAAGAAGGTTCTCCAGGACAAGAGGTTCAAGAACCGAGAGC
TGCAGATCATGCGTAAGCTGGACCACTGCAATATTGTGAGGCTGAGATAC
TTTTTCTACTCCAGTGGCGAGAAGAAAGACGAGCTTTACCTAAATCTGGT
GCTGGAATATGTGCCCGAGACAGTGTACCGGGTGGCCCGCACTTCACCAC
AGGCCAAGTTGACCATCCCTATCCTCTATGTCAAGGTGTACATGTACCAG
CTCTTCCGCAGCTTGGCCTACATCCACTCCCAGGGCGTGTGTCACCGCGA
CATCAAGCCCCAGAACCTGCTGGTGGACCCTGACACTGCTGTCCTCAAGC
TCTGCGATTTTGGCAGTGCAAAGCAGTTGGTCCGAGGGGAGCCCAATGTC
TCCTACATCTGTTCTCGCTACTACCGGGCCCCAGAGCTCATCTTTGGAGC
CACTGATTACACCTCATCCATCGATGTTTGGTCAGCTGGCTGTGTACTGG
CAGAGCTCCTCTTGGGCCAGCCCATCTTCCCTGGGGACAGTGGGGTGGAC
CAGCTGGTGGAGATCATCAAGGTGCTGGGAACACCAACCCGGGAACAAAT
CCGAGAGATGAACCCCAACTACACGGAGTTCAAGTTCCCTCAGATTAAAG
CTCACCCCTGGACAAAGGTGTTCAAATCTCGAACGCCGCCAGAGGCCATC
GCGCTCTGCTCTAGCCTGCTGGAGTACACCCCATCCTCAAGGCTCTCCCC
ACTAGAGGCCTGTGCGCACAGCTTCTTTGATGAACTGCGATGTCTGGGAA
CCCAGCTGCCTAACAACCGCCCACTTCCCCCTCTCTTCAACTTCAGTGCT
GGTGAACTCTCCATCCAACCGTCTCTCAACGCCATTCTCATCCCTCCTCA
CTTGAGGTCCCCAGCGGGCACTACCACCCTCACCCCGTCCTCACAAGCTT
TAACTGAGACTCCGACCAGCTCAGACTGGCAGTCGACCGATGCCACACCT
ACCCTCACTAACTCCTCCTGAGGGCCCCACCAAGCACCCTTCCACTTCCA
TCTGGGAGCCCCAAGAGGGGCTGGGAAGGGGGCCATAGCCCATCAAGCT
CCTGCCCTGGCTGGGCCCCTAGACTAGAGGGCAGAGGTAAATGAGTCCCT
GTCCCCACCTCCAGTCCCTCCCTCACCAGCCTCACCCCTGTGGTGGGCTT
TTTAAGAGGATTTTAACTGGTTGTGGGGAGGGAAGAGAAGGACAGGGTGT
TGGGGGGATGAGGACCTCCTACCCCCTTGGCCCCCTCCCCTCCCCCAGAC
CTCCACCTCCTCCAGACCCCCTCCCCTCCTGTGTCCCTTGTAAATAGAAC
CAGCCCAGCCCGTCTCCTCTTCCCTTCCTGGCCCCCGGGTGTAAATAGA
TTGTTATAATTTTTTCTTAAAGAAAACGTCGATTCGCACCGTCCAACCT
GGCCCCGCCCCTCCTACAGCTGTAACTCCCCTCCTGTCCTCTGCCCCAA
GGTCTACTCCCTCCTCACCCCACCCTGGAGGGCCAGGGGAGTGGAGAGAG
CTCCTGATGCTTAGTTTCCACAGTAAGGTTTGCCTGTGTACAGACCTCC
GTTCAATAAATTATTGGCATGAAAACCTGAAAAAAAAAAAAAAAAAAAA

GSK-3α protein, amino acid sequence (SEQ ID No:
2):
(>gi|49574532|ref|NP_063937.2|glycogen synthase
kinase 3 alpha [Homo sapiens])
MSGGGPSGGPGGSGRARTSSFAEPGGGGGGGGGGPGGSASGPGGTGGGK
ASVGAMGGGVGASSSGGGPGGSGGGGSGGPGAGTSFPPPGVKLGRDSGKV
TTVVATLGQGPERSQEVAYTDIKVIGNGSFGVVYQARLAETRELVAIKKV
LQDKRFKNRELQIMRKLDHCNIVRLRYFFYSSGEKKDELYLNLVLEYVPE
TVYRVARHFTKAKLTIPILYVKVYMYQLFRSLAYIHSQGVCHRDIKPQNL
LVDPDTAVLKLCDFGSAKQLVRGEPNVSYICSRYYRAPELIFGATDYTSS
IDVWSAGCVLAELLLGQPIFPGDSGVDQLVEIIKVLGTPTREQIREMNPN
YTEFKFPQIKAHPWTKVFKSRTPPEAIALCSSLLEYTPSSRLSPLEACAH
SFFDELRCLGTQLPNNRPLPPLENFSAGELSIQPSLNAILIPPHLRSPAG
TTTLTPSSQALTETPTSSDWQSTDATPTLTNSS GSK-3β mRNA, nucleotide sequence (SEQ ID No: 3):
(>gi|21361339|ref|NM_002093.2|Homo sapiens glyco-
gen synthase kinase 3 beta (GSK3B), mRNA)
ATCATCTATATGTTAAATATCCGTGCCGATCTGTCTTGAAGGAGAAATAT
ATCGCTTGTTTTGTTTTTTATAGTATACAAAAGGAGTGAAAAGCCAAGAG
GACGAAGTCTTTTTCTTTTTCTTCTGTGGGAGAACTTAATGCTGCATTTA
TCGTTAACCTAACACCCCAACATAAAGACAAAAGGAAGAAAAGGAGGAAG
GAAGGAAAAGGTGATTCGCGAAGAGAGTGATCATGTCAGGGCGGCCCAGA
ACCACCTCCTTTGCGGAGAGCTGCAAGCCGGTGCAGCAGCCTTCAGCTTT
TGGCAGCATGAAAGTTAGCAGAGACAAGGACGGCAGCAAGGTGACAACAG
TGGTGGCAACTCCTGGGCAGGGTCCAGACAGGCCACAAGAAGTCAGCTAT
ACAGACACTAAAGTGATTGGAAATGGATCATTTGGTGTGGTATATCAAGC
CAAACTTTGTGATTCAGGAGAACTGGTCGCCATCAAGAAAGTATTGCAGG
ACAAGAGATTTAAGAATCGAGAGCTCCAGATCATGAGAAAGCTAGATCAC
TGTAACATAGTCCGATTGCGTTATTTCTTCTACTCCAGTGGTGAGAAGAA
AGATGAGGTCTATCTTAATCTGGTGCTGGACTATGTTCCGGAAACAGTAT
ACAGAGTTGCCAGACACTATAGTCGAGCCAAACAGAGCTCCCTGTGATT
TATGTCAAGTTGTATATGTATCAGCTGTTCCGAAGTTTAGCCTATATCCA
TTCCTTTGGAATCTGCCATCGGGATATTAAACCGCGAACCTCTTGTTGG
ATCCTGATACTGCTGTATTAAAACTCTGTGACTTTGGAAGTGCAAAGCAG
CTGGTCCGAGGAGAACCCAATGTTTCGTATATCTGTTCTCGGTACTATAG
GGCACCAGAGTTGATCTTTGGAGCCACTGATTATACCTCTAGTATAGATG
TATGGTCTGCTGGCTGTGTGTTGGCTGAGCTGTTACTAGGACAACCAATA
TTTCCAGGGGATAGTGGTGTGGATCAGTTGGTAGAAATAATCAAGGTCCT
GGGAACTCCAACAAGGGAGCAAATCAGAGAAATGAACCCAAACTACACAG
AATTTAAATTCCCTCAAATTAAGGCACATCCTTGGACTAAGGATTCGTCA
GGAACAGGACATTTCACCTCAGGAGTGCGGGTCTTCCGACCCCGAACTCC
ACCGGAGGCAATTGCACTGTGTAGCCGTCTGCTGGAGTATACACCAACTG
CCCGACTAACACCACTGGAAGCTTGTGCACATTCATTTTTTGATGAATTA
CGGGACCCAAATGTCAAACTACCAAATGGGCGAGACACACCTGCACTCTT
CAACTTCACCACTCAAGAACTGTCAAGTAATCCACCTCTGGCTACCATCC
TTATTCCTCCTCATGCTCGGATTCAAGCAGCTGCTTCAACCCCCACAAAT
GCCACAGCAGCGTCAGATGCTAATACTGGAGACCGTGGACAGACCAATAA
TGCTGCTTCTGCATCAGCTTCCAACTCCACCTGAACAGTCCCGAGCAGCC
AGCTGCACAGGAAAAACCACCAGTTACTTGAGTGTCACTCAGCAACACTG
GTCACGTTTGGAAAGAATATTAAAAAAAAAAAAAAAAAAAA -continued GSK-3β protein, amino acid sequence (SEQ ID No: 4):
(>gi|21361340|ref|NP_002084.2|glycogen synthase kinase 3 beta [Homo sapiens])

MSGRPRTTSFAESCKPVQQPSAFGSMKVSRDKDGSKVTINVATPGQGPDR

PQEVSYTDTKVIGNGSFGVVYQAKLCDSGELVAIKKVLQDKRFKNRELQI

MRKLDHCNIVRLRYFFYSSGEKKDEVYLNLVLDYVPETVYRVARHYSRAK

QTLPVIYVKLYMYQLFRSLAYIHSFGICHRDIKPQNLLLDPDTAVLKLCD

KFGSAQLVRGEPNVSYICSRYYRAPELIFGATDYTSSIDVWSAGCVLAEL

LLGQPIFPGDSGVDQLVEIIKVLGTPTREQIREMNPNYTEFKFPQIKAHP

WTKDSSGTGHFTSGVRVFRPRTPPEAIALCSRLLEYTPTARLTPLEACAH

SFFDELRDPNVKLPNGRDTPALFNFTTQELSSNPPLATILIPPHARIQAA

ASTPTNATAASDANTGDRGQTNNAASASASNST

The function and advantage of these and other embodiments of the present invention will be more fully understood from the examples below. The following examples are intended to illustrate the benefits of the present invention, but do not exemplify the full scope of the invention.

EXAMPLES

Materials and Methods

Compounds: (6-Bromoindirubin-3'-oxime) BIO (B1686), AR-A014418 (A3230), SB-216763 (S3442), and SB-415286 (S3567), were purchased from Sigma-Aldrich. Enzastaurin (LY317615) and CHIR-99021 were custom synthesized by Shanghai Medicilon Inc. BIM-I (bisindoylmaleimide I) was purchased from Calbiochem (203290). Ruboxistaurin (LY333531) was purchased from A.G Scientific. UCN-01 was purchased from Biomol. Sunitinib was purchased from International Chemical Corporation. Midostaurin (P-7600) and lestaurtinib (L-6307) were purchased from LC Laboratories. Compound stock solutions were made in 10 mM DMSO, stored at −20° C., and diluted to appropriate concentrations for the in vitro kinase assay and cellular assays.

Chemical Screening: To identify chemicals that can both inhibit GSK-3 and cause β-catenin accumulation in cells, a library of ~300 small molecules known to target kinases was assembled, including all kinase inhibitors that are approved drugs and as many of the compounds in clinical development as could be obtained from commercial sources and custom synthesis. These compounds were tested in duplicate in a GSK-3β kinase assay and compounds with an $IC_{50}$ less than 2.5 μM were chosen for follow-up study in cells.

Kinase Assay: Recombinant full-length human GSK-3β (NM_002093) with an N-terminal GST tag was expressed using a baculovirus in Sf9 insect cells and purified on glutathione-conjugated agarose and stored at −80° C. in a storage buffer consisting of 50 mM Tris-HCl, pH 7.5, 150 mM NaCl, 0.25 mM DTT, 0.1 mM EGTA, 0.1 mM EDTA, 0.1 mM PMSF, and 25% glycerol (40007 BPS Biosciences). A phosphorylated primed GSK-3 substrate peptide (Tyr-Arg-Arg-Ala-Ala-Val-Pro-Pro-Ser-Pro-Ser-Leu-Ser-Arg-His-Ser-Ser-Pro-His-Gln-Ser(PO3H2)-Glu-Asp-Glu-Glu-Glu) was custom synthesized by American Peptide Company Incorporated (31153). 20 μL of assay buffer mix (25 mM Tris, 10 mM $MgCl_2$, 5 mM DTT, 0.1 mg/ml BSA, 0.2 U/ml Heparin, 3.2 μM peptide substrate, 1 μg/mL of human GSK-3β was added to each well of white-bottomed, 384-well plate (Nunc 242790, VWR) using Multidrop Combi dispenser (Perkin Elmer) with the standard cassette. Plates were spun down at 1000 rpm afterwards. 100 mL of each compound was transferred from the compound stock plate to assay plates by CyBi-Well Vario robotic system (CyBio). After 45 min, ATP (10 μL) was added to each well using Multidrop Combi dispenser to a final concentration of 1 μM. After 90 minutes incubation in the presence of ATP at room temperature, 30 μL Kinase-Glo (Promega) was added to each well. Plates were incubated for an additional 40 min at room temperature in Kinase-Glo reagents before the luminescent signals were read on Envision (Perkin Elmer). Results were analyzed in Microsoft Excel.

Cellular-β-Catenin Stability Assay: To study effects of small molecules on GSK-3/β-catenin signaling in cells, we optimized an image-based assay that measures β-catenin stability. This assay uses human U2OS cells engineered to express a genetically encoded fluorescent reporter consisting of a fusion of β-catenin to enhanced green fluorescent protein (eGFP) that were obtained from Thermo Fisher Scientific (Denmark). Imaging of this cell line, named βCat-eGFP, under basal conditions reveals a faint membrane-localized signal due to the constitutive proteasome-mediated degradation of the βCat-eGFP reporter and interaction of a remaining subpopulation with cadherins in the cell membrane. βCat-eGFP cells have been successfully cultured in optically clear 96- and 384-well plates and imaged as both live cells and after fixation. Treatment of the βCat-eGFP with known GSK-3 inhibitors, such as AR-A014418 (20 μM) over 20 hrs, causes a dose dependent increase in eGFP fluorescence and the accumulation of the βCat-eGFP reporter in the cytoplasm and nucleus. Lithium treatments at 10 mM and valproic acid at 10 mM also have the same effect in this assay. Compounds were pin-transferred or pipetted in dilution onto cells and after 21-24 hrs wells were fixed in paraformaldehyde and stained with Hoechst 33342 dye to detect nuclei. Cells were imaged on an ImageXpress Micro (Molecular Devices) automated microscope at 10× magnification with detection of both DNA and eGFP fluorescence. The percentage of eGFP positive cells was calculated and compared to an untreated control.

Amphetamine-Induced Hyperactivity Assay (AIH)

Surgery: Mice receiving intracranial infusions were implanted with stainless steel guide cannula (Plastics One, Roanoke, Va.) aimed at the dorsal third ventricle. Mice were anesthetized with ketamine/xylazine (150 mg/kg and 10 mg/kg respectively; 5 mls/kg injection volume). Using a stereotaxic apparatus, guide cannula (C232GC, 26 gauge, Plastics One) with inserted dummy cannula (C232DC) were directed toward the dorsal third ventricle (−0.5 mm posterior to Bregma, ±0.0 lateral to midline, and −3.0 (injection site) ventral to the skull surface), (Paxinos, 2001). Mice recovered for at least 5 days prior to testing. During infusions, mice were gently restrained. Dummy cannula were replaced with injection cannula (26 gauge; extending 1.0 mm beyond the tip of the 2.0 mm guide; C232I) attached to polyethylene tubing (PE50) connected to a 10 μl Hamilton syringe. Infusions were controlled by a microinfusion pump (KDS 100, KD Scientific; New Hope, Pa.). Mice receiving intra-Striatal Chiron99021 went through identical surgical procedures except cannulae were directed toward the dorsal striatum (+1.1 mm A/P, ±1.3 mm M/L, −4.5 mm DN).

Drugs: For ICV administration, Chiron99021 was dissolved in 100% DMSO and administered intracerebralventricularly at a volume of 1.0 μl and a rate of 0.5 μl per minute (Various doses detailed in figure legends). For systemic administration, Chiron99021 was dissolved in a solution consisting of 45% polyethylene glycol 400, 45% NaCl, and 10% dimethyl sulfoxide at various doses (detailed in figure legends) and an injection volume of 10 mls/kg. D-Amphetamine sulfate salt (Sigma Chemical Co., St Louis, Mo.) was dissolved in 0.9% NaCl and administered at 3.5 mg/kg. Lithium chloride (Sigma) was dissolved in 0.9% NaCl and was administered at 85 mg/kg. Both drugs were administered at 5 mls/kg body weight. AR-A014418 was administered i.p. at 9 mg/kg in a vehicle consisting of 0.3% DMSO in saline. SB216763 was administered either ICV (in 100% DMSO vehicle) or i.p. at 5 mg/kg, 10 mg/kg, or 20 mg/kg in vehicle consisting of 0.1% Tween in water. Both drugs were administered at 5 mls/kg body weight.

Systemic administration of 85 mg/kg lithium was determined to result in a serum level of about 1 mM 1 hr after i.p. injection. Accordingly, administration of a sub-effective dose of lithium (50 mg/kg) can be extrapolated to result in approximately 0.3-0.6 mM serum lithium levels. Systemic administration of 50 mg/kg of Chir99021 was determined to result in a maximum serum level of about 69 μM, whereas administration of 12.5 mg/kg resulted in a maximum serum level of about 15 μM. Accordingly, the consistently sub-effective dose of 3.125 mg/kg can be extrapolated to result in a maximum serum level of about 3-4 μM.

Behavioral Procedures: Amphetamine-induced hyperactivity (AIH) was examined in eight identical open-field chambers (16.5"×16"×12"; AccuScan Instruments, Columbus, Ohio). Activity was detected by infrared beam breaks and recorded automatically by VersaMax software (AccuScan). Daily sessions were automatically binned in 5 minute intervals (VersaDat; AccuSacn) for statistical analysis. AIH was run over three consecutive days as follows:

Day 1: For ICV Experiments, mice were acclimated to the infusion procedure by gently restraining them and removing the dummy cannula. Mice were restrained for three minutes at which point the dummy cannula was replaced. Mice were then placed into the open-field for 20 minutes and then removed for a saline injection. Mice were placed back into the open-field for an additional 30 minutes, at which point the mice were returned to their home cage. For systemic experiments, mice received a saline injection 40 minutes prior to being placed in the open-field. After 20 minutes, the mice receive another saline injection and are placed in the open-field for 30 minutes.

Day 2 was run identically to Day 1, with the exception that the second day lasted for one hour (20 minutes→injection→40 minutes), and the restraint acclimation included an ICV saline infusion (2 minute infusion followed by one minute for drug diffusion away from the injection cannula). For systemic experiments, mice received two saline injections; one 40 minutes prior to being placed in the boxes and another after 20 minutes in the box.

Day 3 was the amphetamine challenge day. Mice were pre-treated with an infusion/i.p. injection of drug (Lithium, Chiron99021, enzastaurin, ruboxistaurin, AR-A014418, or SB216763) or vehicle 40 minutes prior to being placed in the open-field. After 20 minutes, mice were removed and challenged with amphetamine, and placed back in the open-field for 80 minutes.

Example 1

Identification and Characterization of GSK3 Inhibitors

Of the small molecule kinase inhibitors that are in clinical development and/or are approved drugs, there were a total of 6 compounds that inhibited GSK-3β with $IC_{50}$s less than 2.5 μM: ruboxistaurin (a macrocyclic bisindoylmaleimide), enzastaurin (an acyclic bisindoylmaleimide), midostaurin (an indolocarbazole), lestaurtinib (an indolocarbazole), 7-hydroxystaurosporine (an indolocarbazole), and sunitinib (an indole). The clinical use and known activities of these compounds toward kinases are summarized in FIGS. 2-7. Further follow-up dose response testing has indicated that ruboxistaurin, enzastaurin, midostaurin, and UCN-01 have $IC_{50}$s less than 50 nM, while sunitinib ($IC_{50}$ of ~1.7 μM), and lestaurtinib ($IC_{50}$ of ~2.3 μM) were less potent.

Figure 9:
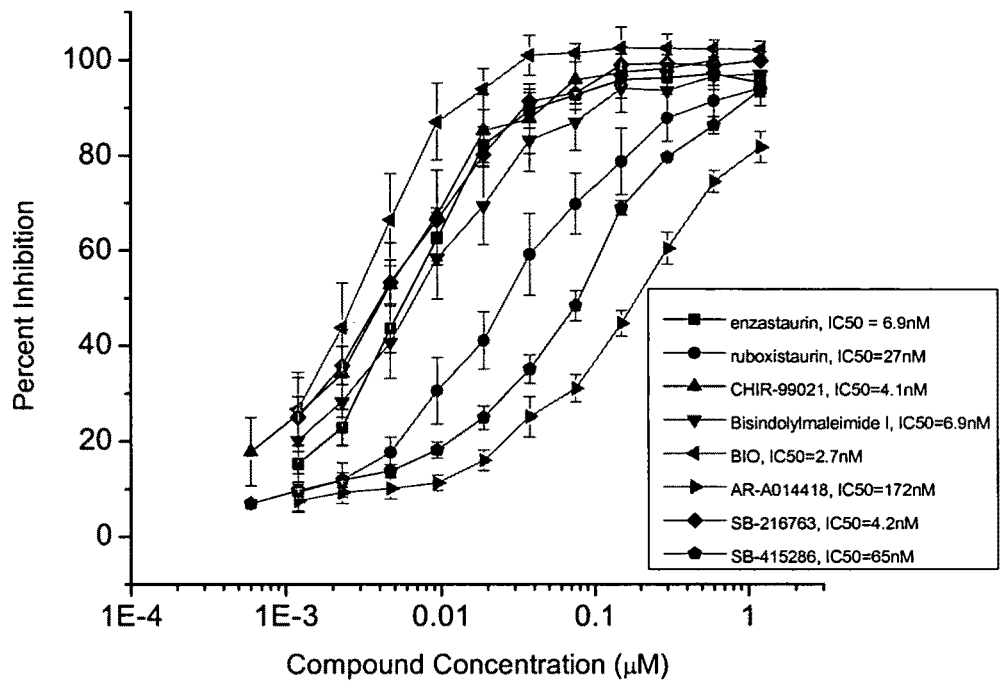
FIG. 9 illustrates the dose response of the most potent GSK-3 inhibitors identified along with known GSK-3 inhibitors. Each data point represents mean±SEM (n=4). IC$_{50}$s were calculated based on the logistic function in MicroOrigin Software. The in vitro GSK-3$\beta$ kinase assay contained less than 0.3% DMSO in the final assay buffer. Microliter liquid dispensing was handled by Multidrop Combi (Thermo Scientific). Nanoliters of compounds were transferred to assay solution by CyBi-Well vario robotics system (CyBio). Luminescence signal was measured and recorded using an EnVision Multilabel Reader (Perkin Elmer)
Figure 10:
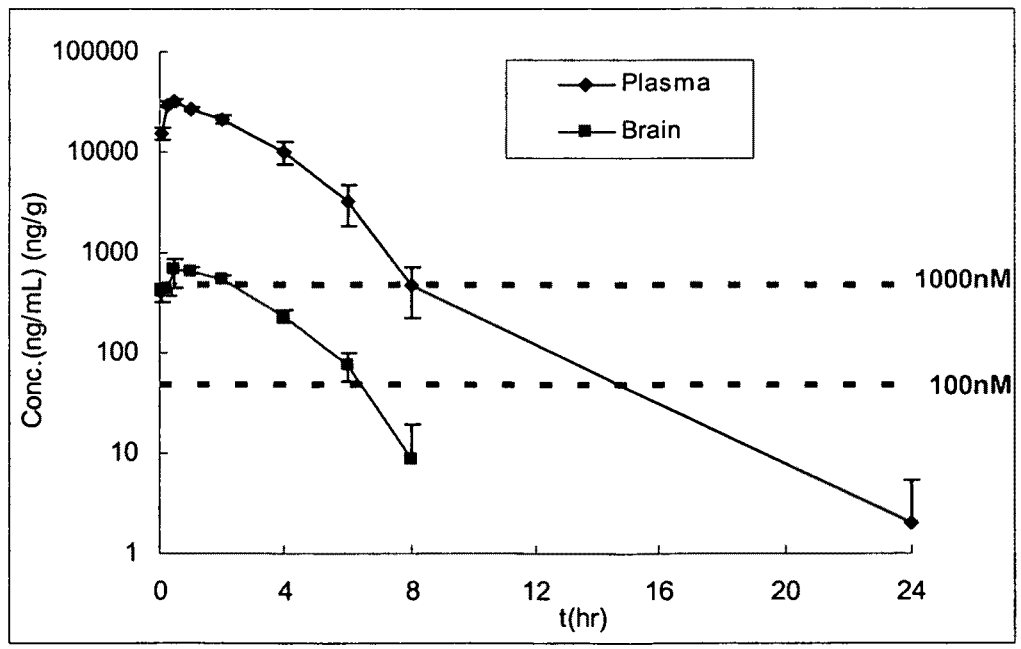
FIG. 10 shows a concentration time curve of Chir99021 in plasma and brain following IP administration of a single dose.

Due to the enhanced selectivity, relative to the indolocarbazoles class, of the bisindoylmaleimide class of compounds, this class of compounds was tested in additional follow-up assays. As shown in FIG. 9, the potency of ruboxistaurin ($IC_{50}$ of ~27 nM) and enzastaurin ($IC_{50}$ of ~6.9 nM) was found to be similar to that of the known GSK-3 inhibitors CHIR-99021 ($IC_{50}$ of ~4.1 nM), SB-216763 ($IC_{50}$ of ~4.2 nM), BIM-I ($IC_{50}$ of ~6.9 nM), and greater than that of AR-A014418 ($IC_{50}$ of ~172 nM), and SB-419286 ($IC_{50}$ of ~65 nM). The potency of ruboxistaurin and enzastaurin was less than the non-selective kinase inhibitor BIO (6-bromoindirubin-3'-oxime) ($IC_{50}$ of ~2.7 nM FIG. 10 shows a concentration time curve of Chir99021 in plasma and brain following IP administration of a single dose; 50 mg/kg dose in C57BL/6 male mice in 10% DMSO/45% PEG400/45% saline. Horizontal lines indicate 100 nM and 1000 nM for reference.

Example 2

β-Catenin Stabilization by GSK-3 Inhibitors

When tested in the βCat-eGFP reporter assay, enzastaurin, ruboxistaurin, midostaurin, and sunitinib were all able to cause β-catenin accumulation, a sign of GSK-3 inhibition. FIG. 9 shows the dose response of the most potent GSK-3 inhibitors identified and known GSK-3 inhibitors. Each data point represents a mean±SEM (n=4) IC50s were calculated based on the logistic function in MicroOrigin Software. The in vitro GSK-3 kinase assay contained less than 0.3% DMSO in the final assay buffer. Microliter liquid dispensing was handled by Multidrop Combi (Thermo Scientific). Nanoliters of compounds were transferred to assay solution by CyBi-Well vario robotics system (CyBio). Luminescence signal was measured and recorded using an Envision Multilabel Reader (Perkin Elmer).

This result indicates that the compounds are cell permeable and able to affect GSK-3/β-catenin signaling in intact cells. Since increasing β-catenin levels in the mouse brain has been shown to mimic lithium's mood stabilizing effect, these small molecules may be of interest for treatment of Bipolar Disorder. Furthermore, it has been shown that systemic administration of SB-216763 to mice (10 mg/kg; i.p.) attenuates hyperactivity in dopamine transporter (DAT) knockout mice, a model for mania in which lithium is active (Beaulieu et al. 2004). Given the activity of SB-216763 in this model, and its structural similarity to enzastaurin and ruboxistaurin, these compounds may also have anti-manic activities when administered systemically to animals.

Example 3

Synergy of GSK3 Inhibitors and Lithium In Vitro

Figure 11:
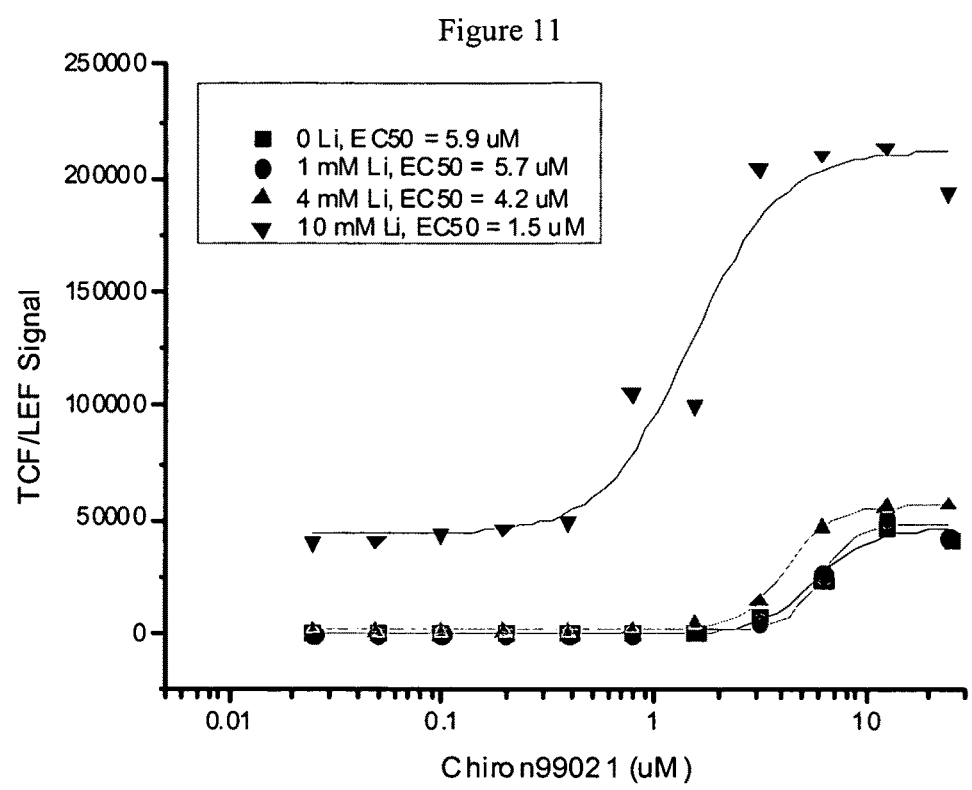
FIG. 11 shows how Lithium potentiates the TCF/LEF signal in the presence of Chir99021.

The potential of lithium to potentiate the TCF/LEF signal of a GSK3 inhibitor was tested in HEK293 cells stably transfected with the βCat-eGFP TCF/LEF reporter. TCF/LEF reporter signal was measured in cells exposed to various concentrations of lithium chloride (0 mM, 1 mM, 4 mM, and 10 mM) in the presence of different concentrations of Chir99021 (FIG. 11). In the presence of lithium, both the maximum efficacy and the potency of Chir99021 in stimulating TCF/LEF response increased.

Figure 12:
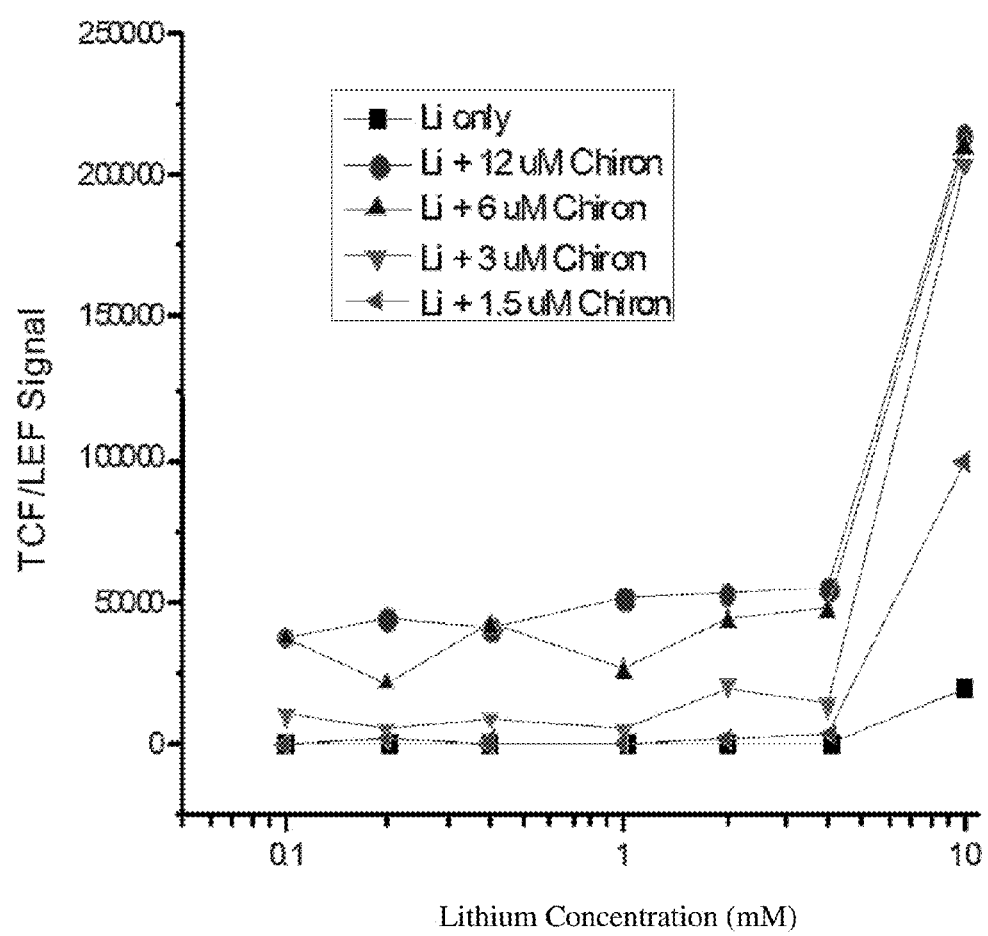
FIG. 12 shows how Lithium potentiates the TCF/LEF signal in the presence of Chir99021.
Figure 13:
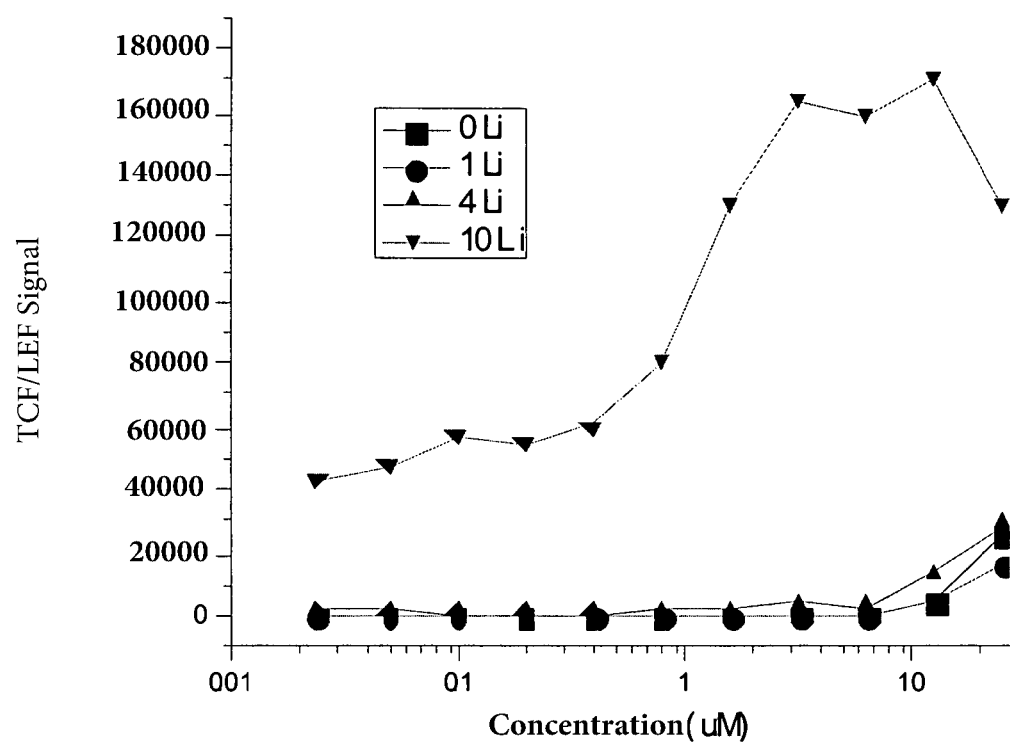
FIG. 13 shows how Lithium potentiates the TCF/LEF signal in the presence of other GSK3 inhibitors.
Figure 13:
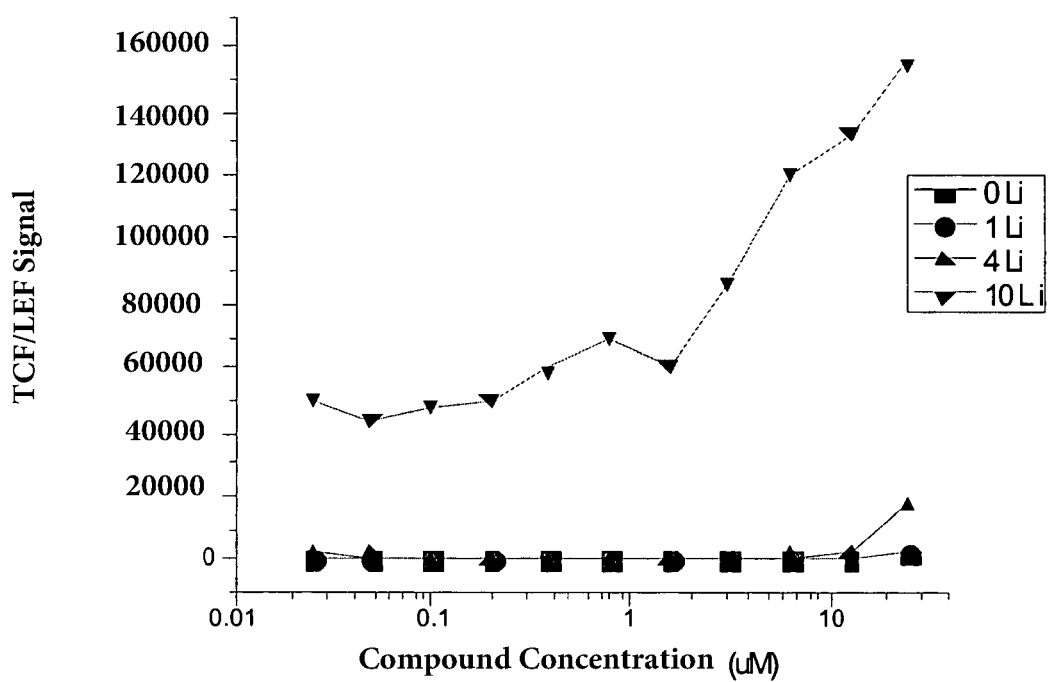
Figure 13:
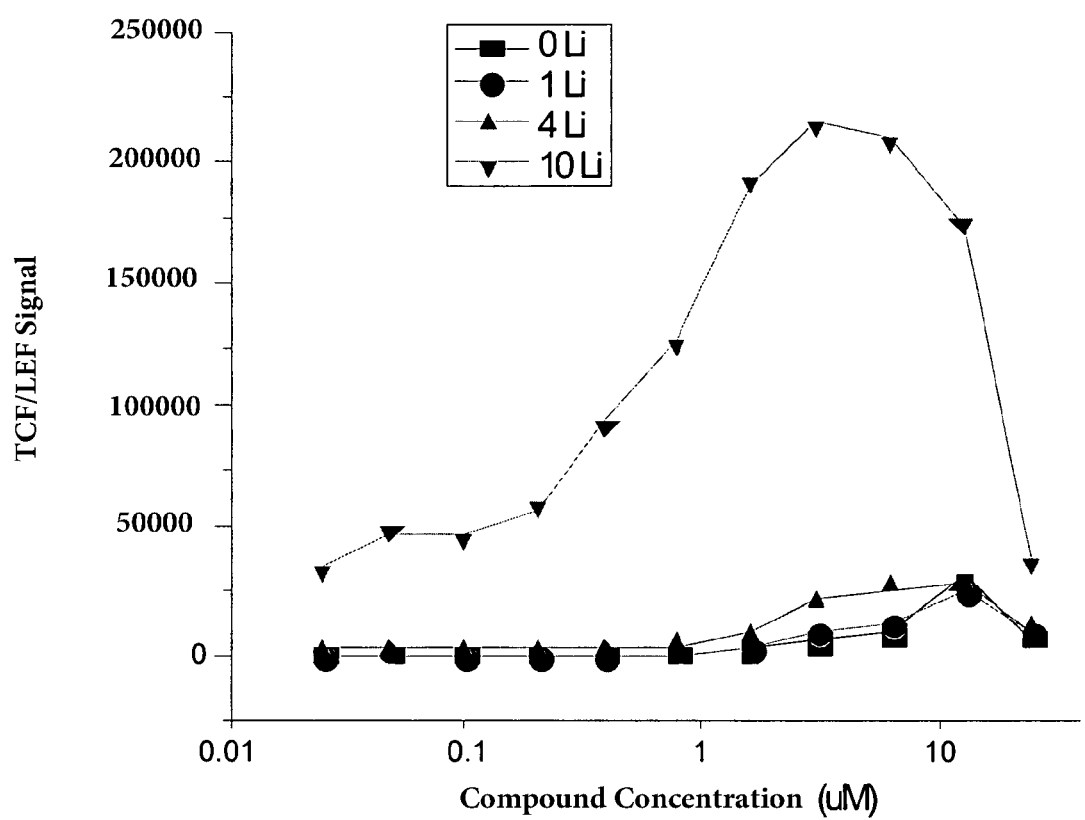

TCF/LEF reporter signal was measured in cells exposed to various concentrations of Chir99021 (0 μM, 1.5 μM, 3 μM, 6 μM, and 12 μM) in the presence of different concentrations of lithium (FIG. 12). In the presence of a high concentration of Chir99021 a synergistic effect is observed with the addition of lithium whereas only an additive effect was observed at lower concentrations TCF/LEF reporter signal was also measured in cells exposed to various concentrations of lithium (0, 1, 4, and 10 mM) in the presence of different concentrations of structurally distinct GSK3 inhibitors (FIG. 13). The concentration of the GSK3 inhibitory compound, SB21563, SB415286, and Bio, respectively, was plotted on the x-axis.

Example 4

In Vivo Effect of GSK-3 Inhibitors in AIH

The effect of GSK3 inhibitors in AIH was examined in an established mouse model predictive for the effectiveness of a mood stabilizer (see O'Donnell and Gould, *The behavioral actions of lithium in rodent models: leads to develop novel therapeutics*. Neurosci Biobehav Rev. 31(6):932-62; 2007; Gould T D, O'Donnell K C, Picchini A M, Manji H K. *Strain differences in lithium attenuation of d-amphetamine-induced hyperlocomotion: a mouse model for the genetics of clinical response to lithium*. Neuropsychopharmacology. 2007 June; 32(6):1321-33. Epub 2006 Dec. 6. incorporated herein in its entirety by reference). A drug's ability to attenuate AIH in this assay constitutes strong evidence that it will be clinically effective for treatment and/or prophylaxis of a neurological disease or psychological disorder, for example, bipolar disorder, mania, or psychosis. On the other hand, a drug's inability to attenuate AIH in this model does not rule out therapeutic applicability.

Mice were pre-treated with a candidate drug, for example, lithium or a GSK-3 inhibitor as provided by some aspects of this invention, and subsequently challenged with amphetamine. Activity was recorded for 80 minutes following the amphetamine challenge.

Figure 14:
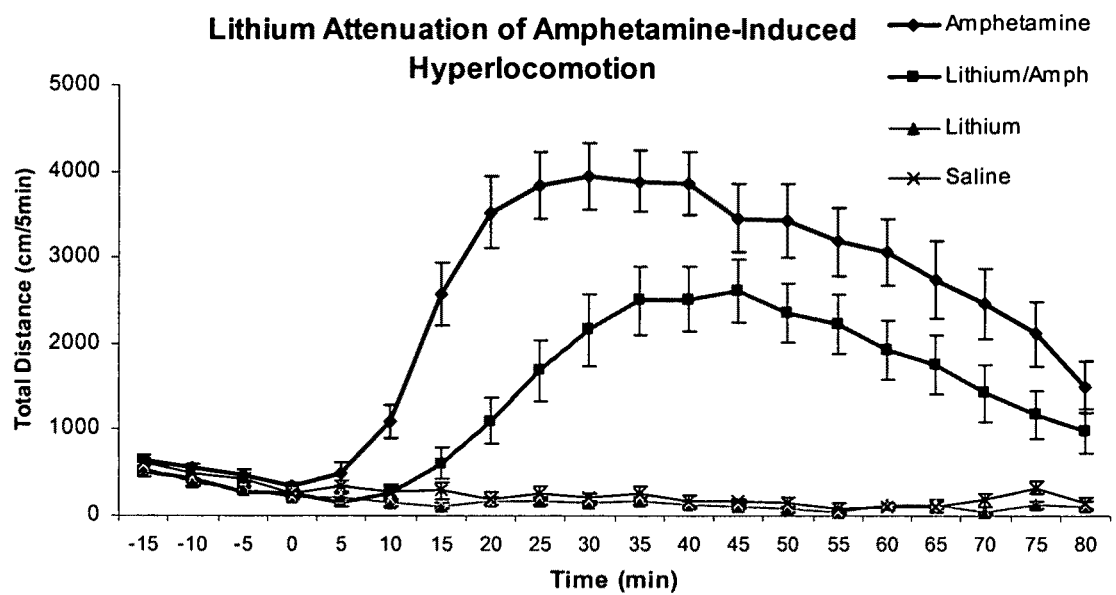
FIG. 14 shows systemic lithium effects in amphetamine-induced hyperactivity (AIH)

FIG. 14 shows activity measurements of C57BL/6J mice pre-treated with saline and mock-challenged with saline (saline/saline), pre-treated with saline and challenged with amphetamine (3.5 mg/kg i.p.) (saline/amph), and pre-treated with a systemic administration of lithium (85 mg/kg, administered i.p) and challenged with amphetamine (lithium/amph) (N=6-15/group). Dosage information is generally given as mg drug/kg body weight of the subject. The number of animals per experiment is given as n or N in the figure legends. The results show that lithium pre-treatment alleviates amphetamine-induced hyperactivity observed in the mice pre-treated with saline alone and validate the predictive value of this model for the efficacy of mood stabilizers, consistent with the published literature.

Figure 15:
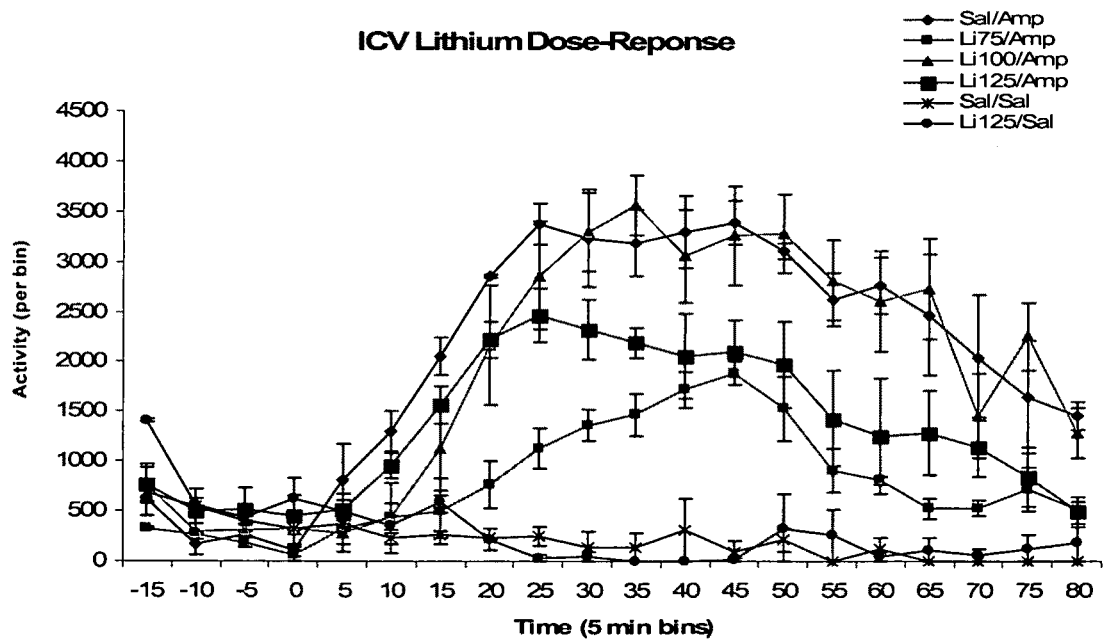
FIG. 15 illustrates ICV lithium dose response in AIH.

FIG. 15 shows activity measurements of C57BL/6J mice pre-treated with saline and mock-challenged with saline (saline/saline), pre-treated with saline and challenged with amphetamine (3.5 mg/kg i.p.) (saline/amph), and pre-treated with different doses of lithium (75 μg/μl, 100 μg/μl, 125 μg/μl; 1 μl administered), administered intracerebral-ventricularly (ICV) and challenged with amphetamine (lithium/amph) (N=2-3/group). These data suggest that the alleviating effect of systemic lithium pre-treatment, as shown in FIG. 14, are mediated, at least in part, by effects within the central nervous system. There were no differences in baseline motor activity, suggesting that the observed attenuation of amphetamine-induced hyperactivity is not due to non-specific motor effects of drug administration but a true effect on the amphetamine behavior.

Figure 16:
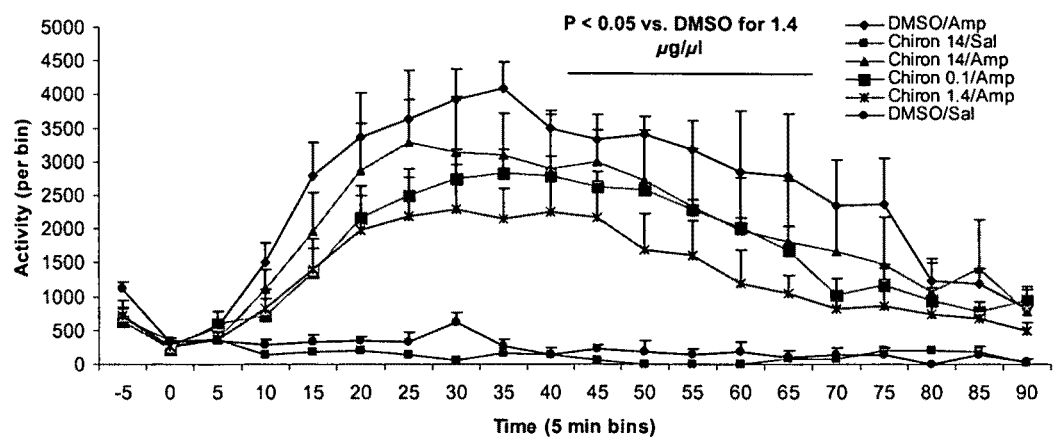
FIG. 16 illustrates ICV Chir99021 dose response in AIH.

FIG. 16 shows activity measurements of C57BL/6J mice pre-treated with DMSO and mock-challenged with saline (DMSO/saline), pre-treated with DMSO and challenged with amphetamine (3.5 mg/kg i.p.) (DMSO/amph), and pre-treated with 1 μl of a solution of different concentrations of Chir99021 (0.1 μg/μl, 1.4 μg/μl, and 14 μg/μl) administered intracerebral-ventricularly (ICV) and challenged with amphetamine (Chir/amph)(N=6/group). Additionally, measurements from mice pre-treated with 14 μg/μl Chir99021 and mock-challenged with saline are shown (Chir/saline). The data suggest that specific GSK-3 inhibitors are effective in attenuating AIH to levels comparable to those observed after lithium administration. No differences in baseline activity for Chir99021-treatment as compared to saline treatment were observed, suggesting that the attenuation is not a result of non-specific motor effects. While at the lower concentrations, the Chir99021 solutions were not of notable viscosity, the solution of 14 μg/μl was observed to be of notable viscosity. Care was taken to administer an accurate volume of the 14 μg/μl solution.

Figure 17:
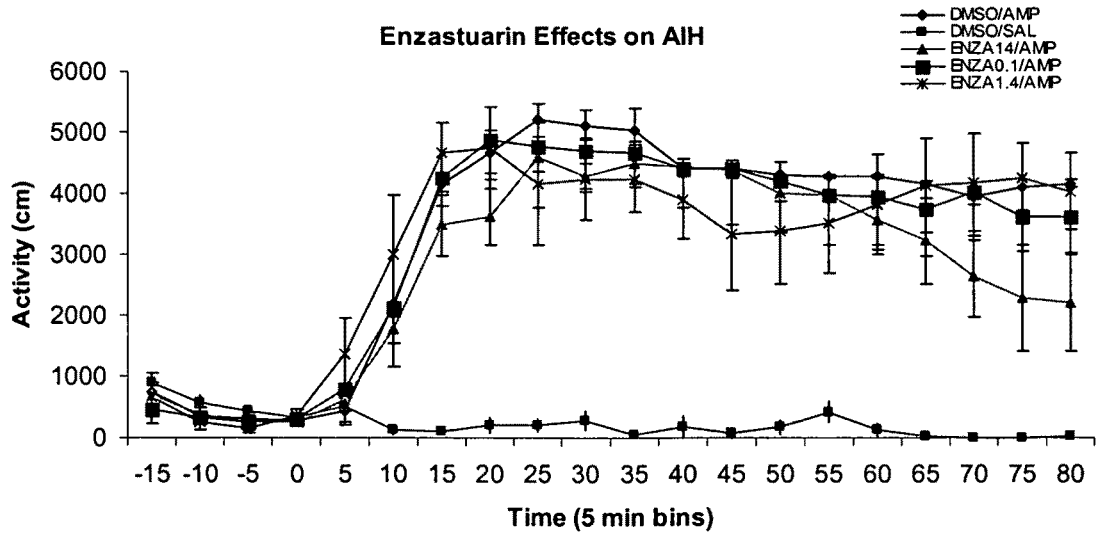
FIG. 17 illustrates ICV Enzastaurin dose response in AIH.
Figure 18:
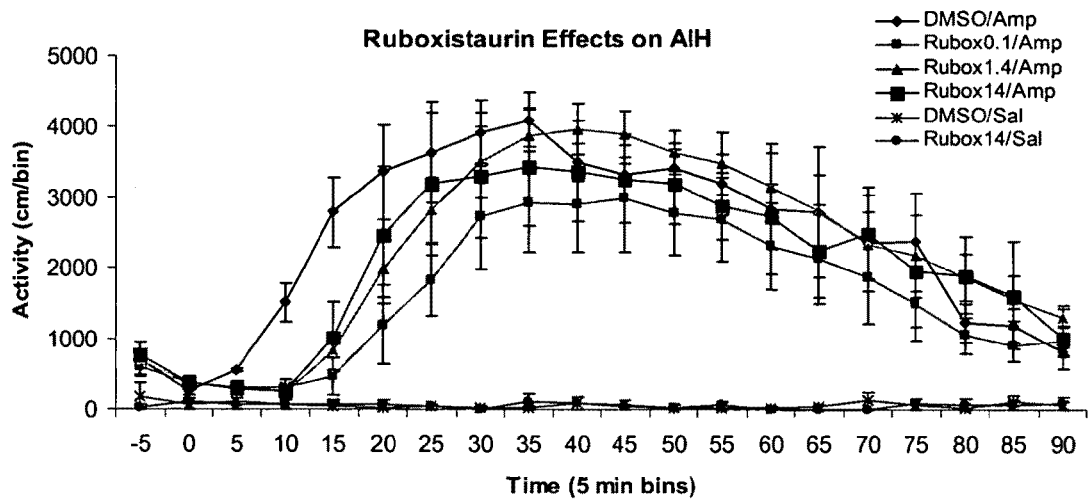
FIG. 18 illustrates ICV Ruboxistaurin dose response in AIH.

FIGS. 17 and 18 show activity measurements of C57BL/6J mice pre-treated with DMSO and mock-challenged with saline (DMSO/saline), pre-treated with DMSO and challenged with amphetamine (3.5 mg/kg i.p.) (DMSO/amph), and pre-treated with 1 μl of different concentrations of enzastaurin (N=3-4/group) or ruboxisturin (N=4-8/group) (0.1 μg/μl, 1.4 μg/μl, and 14 μg/μl) administered intracerebral-ventricularly (ICV) and challenged with amphetamine (enza/amph or ruboxi/amph, respectively). While enzastaurin showed no effect in AIH when administered ICV at doses comparable to Chir99021 (FIG. 17), ruboxistaurine showed a moderate attenuating effect at similar doses (FIG. 18). These data suggest that increased GSK-3 specificity may result in better anti-manic properties. While the effect of ruboxistaurin was not statistically significant, it appears that ruboxistaurin is slightly more effective in attenuating AIH than enzastaurin. Neither drug appears to be as effective as lithium or Chir99021 when administered ICV. It is noteworthy that enzastaurin has a similar affinity for GSK-3 (6.1 nM) as Chir99021 (4.1 nM).

Figure 19:
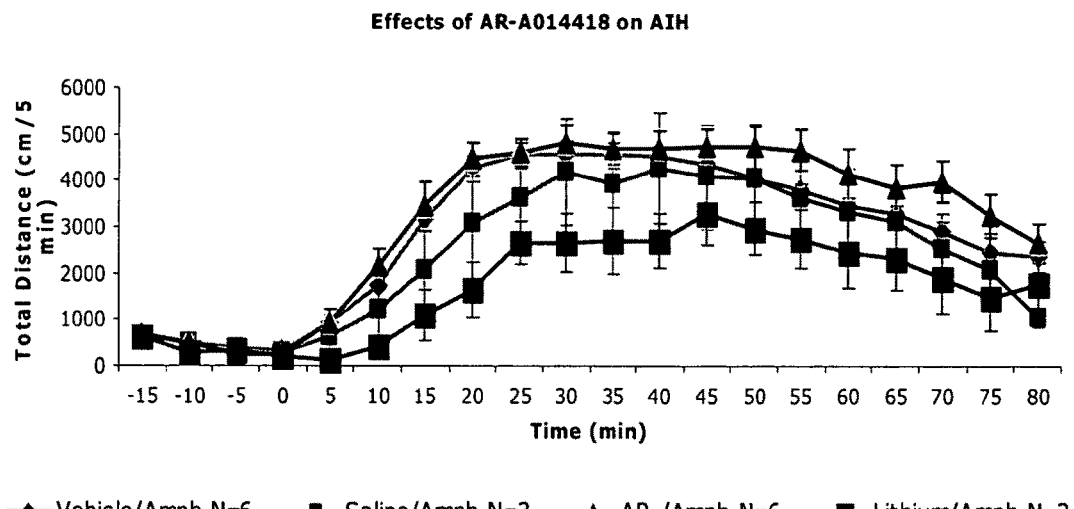
FIG. 19 illustrates systemic AR-A014418 effect in AIH.
Figure 20:
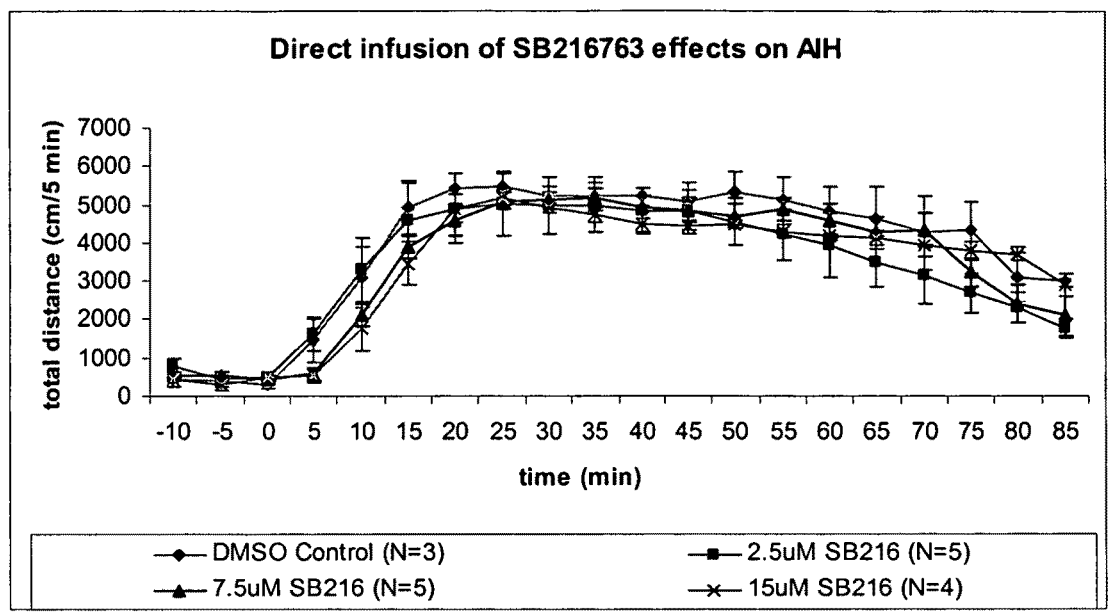
FIG. 20 illustrates systemic SB216763 effect in AIH.
Figure 21:
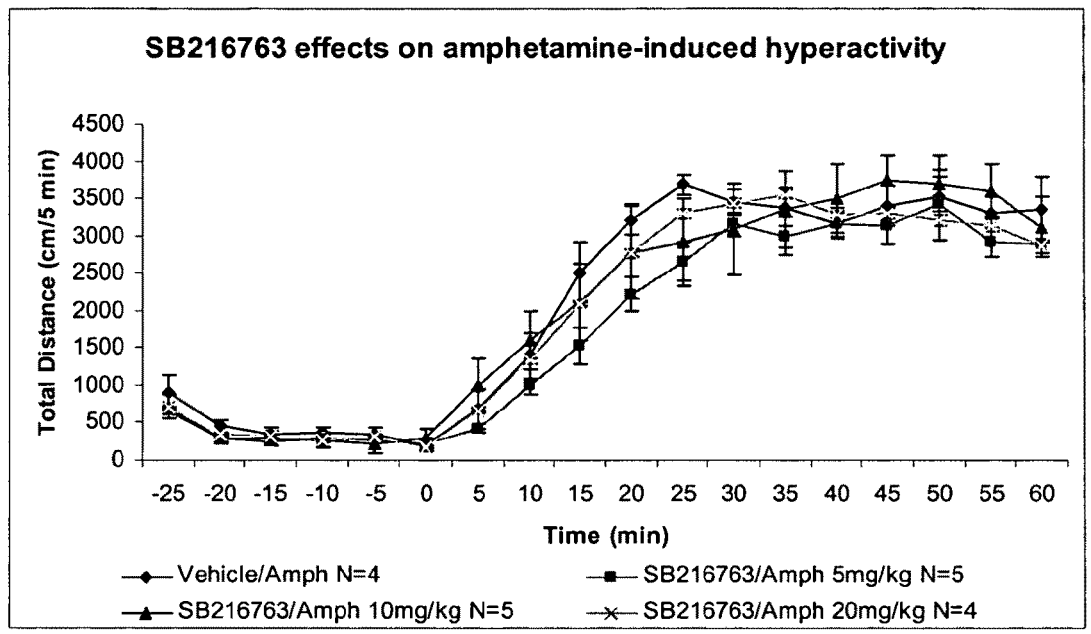
FIG. 21 illustrates ICV SB216763 effect in AIH.

Similarly, FIGS. 19, 20 and 21 show activity measurements of C57BL/6J mice pre-treated with vehicle and challenged with amphetamine (3.5 mg/kg i.p.) (saline vehicle), and pre-treated with AR-A014418 administered i.p. (9 mg/kg at 5 ml/kg volume, in vehicle consisting of 0.3% DMSO in saline) (FIG. 19), or SB216763 administered ICV (in DMSO vehicle) (FIG. 20) or administered i.p. (5 mg/kg, 10 mg/kg, 20 mg/kg in vehicle consisting of 0.1% Tween in water—administered at 5 ml/kg (FIG. 21) and challenged with amphetamine. FIG. 19 further depicts activity measurements of mice treated with lithium and challenged with amphetamine. None of these GSK-3 inhibitors showed a significant effect on hyperactivity when given in the described dosages.

These data suggests that high affinity GSK-3 inhibition levels, as measured in vitro, by themselves are not predictive of the level of drug efficacy in vivo, for example, in an in vivo behavioral model of AIH. This may be due to several factors including but not limited to kinase selectivity, protein binding, active transport mechanisms (e.g., p-glycoprotein efflux), etc. Thus, based on the cellular and biochemical assays described herein, the high level of performance of Chir99021 in the in vivo behavioral AIH model was unexpected.

Figure 22:
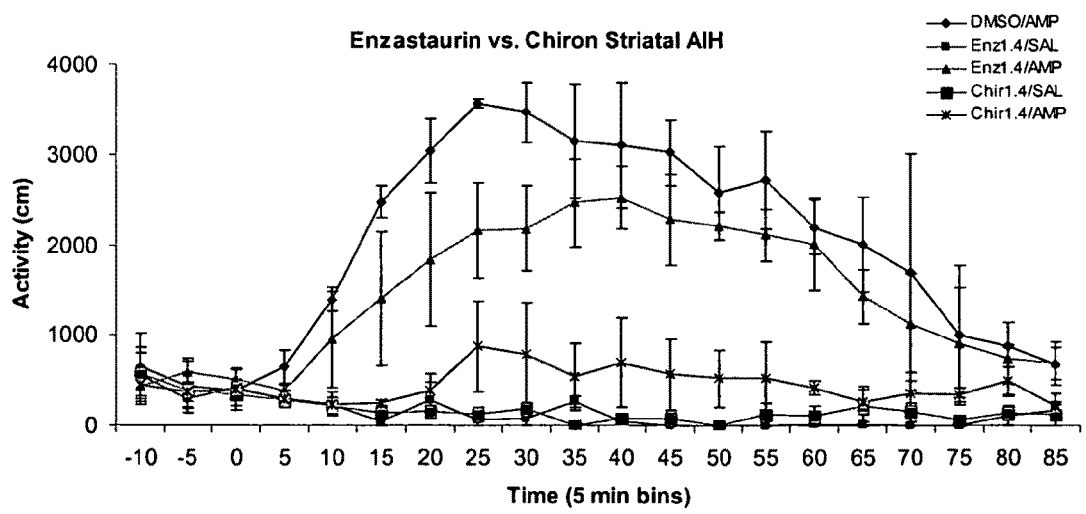
FIG. 22 illustrates striatal infusion of Enzastaurin and Chir99021 effects in AIH.

FIG. 22 shows a comparison of the effect of two GSK-3 inhibitors in AIH after intra-striatal infusion. The amphetamine induced hyperactivity task has been demonstrated to be striatum-dependent. Thus, intra-striatal administration of a compound mediating AIH attenuation can be used to test whether the observed effect is the result of a specific effect of the compound in the striatum. The figure shows activity measurements of C57BL/6J mice pre-treated with DMSO and challenged with amphetamine (3.5 mg/kg i.p.) (DMSO/amph), and pre-treated with 1 μl of 1.4 μg/μl Chir99021 or 1.4 μg/μl of enzastaurin, administered intracerebral-ventricularly (ICV) and challenged with amphetamine (Chir/amph and enza/amph, respectively) (N=3/group). Additionally, measurements from mice pre-treated with 1.4 μg/μl Chir99021 or 1.4 μg/μl enzastaurin and mock-challenged with saline are shown (Chir/saline and enza/saline, respectively). Chir99021 exhibited a greater attenuation when administered directly into the striatum as compared to Chir99021 administered ICV. At this dosage, Chir99021 effected almost complete ablation of the amphetamine-induced hyperactivity, suggesting that the striatum may be a critical site for the observed Chir99021 effect in AIH. This result demonstrates for the first time that single-agent, specific GSK-3 inhibition can alleviate or ablate amphetamine-induced hyperactivity in this model. Further, enzastaurin appeared to be modestly effective (although statistically not significant with a repeated measures ANOVA) when administered directly into the striatum, suggesting that there may be modest effects with enzastaurin if enough compound can get to the striatum.

Example 5

Synergy of GSK-3 Inhibitors and Lithium In Vivo

In order to elucidate synergistic effects of the identified GSK-3 inhibitors effective as mood stabilizers in AIH, various combinations of the respective compounds with different doses of lithium were administered either directly to the central nervous system or systemically before amphetamine challenge.

Figure 23:
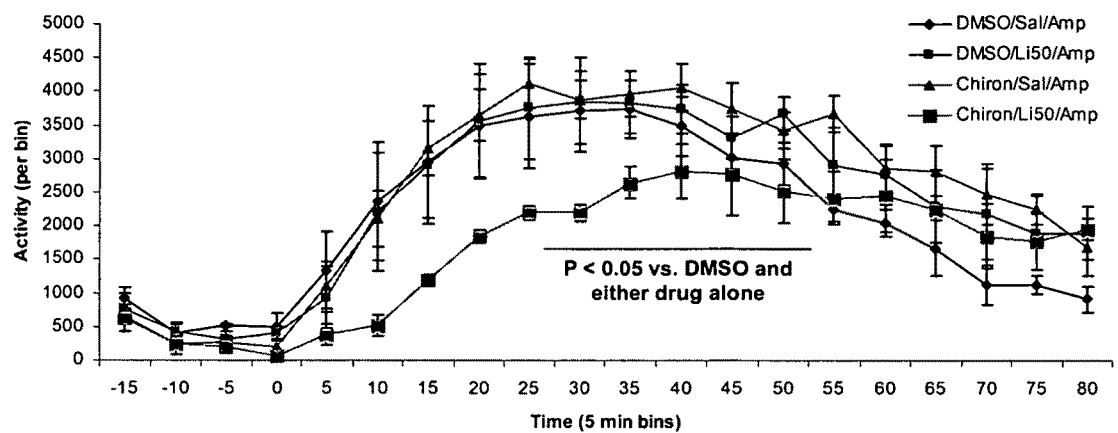
FIG. 23 illustrates the synergy of low dose ICV Chir99021 and systemic lithium.

FIG. 23 shows synergistic effects of Chir99021 and lithium administered at doses that, if administered alone, did not show a significant effect. The figure shows activity measurements of C57BL/6J mice pre-treated with vehicle (DMSO and saline) alone and challenged with amphetamine (3.5 mg/kg i.p.) (DMSO/sal/amph), and pre-treated with 0.1 μg/μl Chir99021 alone, 50 mg/kg lithium alone, or a combination of 0.1 μg/μl Chir99021 and 50 mg/kg lithium, and challenged with amphetamine (Chir/sal/amph, DMSO/Li50/amph and Chir/Li50/amph, respectively)(N=6/group). Chir99021 and DMSO were administered intracerebral-ventricularly (ICV), while lithium was administered systemically (i.p.). Neither Chir 99021 nor lithium attenuated amphetamine-induced hyperactivity when administered alone. However, when administered together, a statistically significant, synergistic attenuation effect was observed.

Example 6

In Vivo Effect of Systemically Administered GSK-3 Inhibitors in AIH

One obstacle in clinical application of GSK-3 inhibitors for the treatment of mood disorders, such as bipolar disorder, is the inability of some small molecule compounds to permeate the blood brain barrier (BBB). Therefore, the feasibility of systemic administration of GSK-3 inhibitory compounds was investigated.

Figure 24:
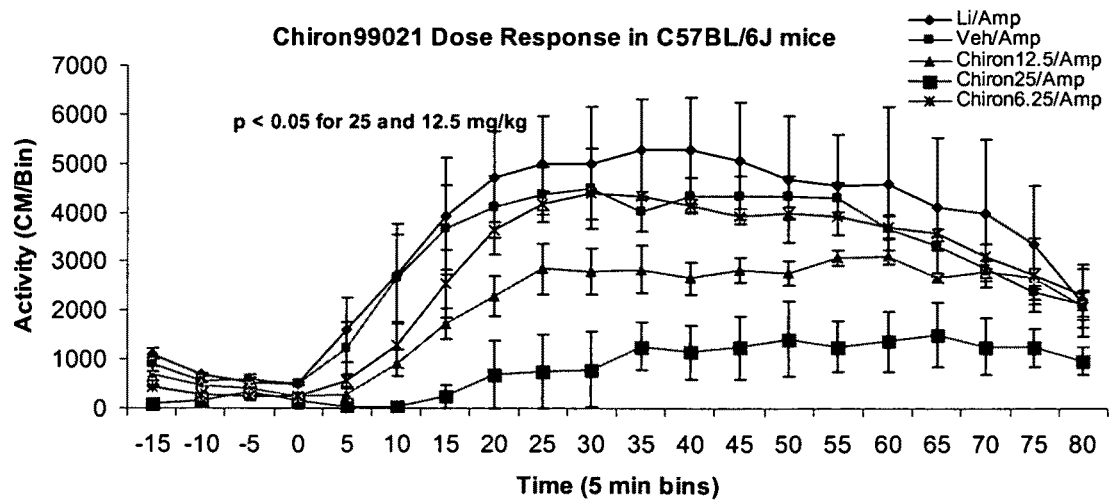
FIG. 24 illustrates a systemic Chir99021 dose response in AIH.

FIG. 24 shows Chir99021 dose response after systemic administration (6.25 mg/kg, 12.5 mg/kg, and 25 mg/kg, single dose i.p. injection)(N=4-8/group). The Figure shows activity measurements of C57BL/6J mice pre-treated with vehicle (DMSO) and challenged with amphetamine (Veh/Amp), pre-treated with Chir99021 at different doses (6.25 mg/kg, 12.5 mg/kg, and 25 mg/kg, single dose i.p. injection) and challenged with amphetamine (3.5 mg/kg i.p.) (Chir 6.25/amph, Chir 12.5/amph, and Chir 25/amph, respectively), and pre-treated with 50 mg/kg lithium (i.p.) and challenged with amphetamine (Li50/amph). The data demonstrate that systemically administered Chir99021 significantly attenuates AIH in a dose-dependent manner when administered 1 hour prior to amphetamine challenge. Both the 12.5 mg/kg and 25 mg/kg dosages of Chir99021 significantly decreased amphetamine-induced hyperactivity compared to vehicle/amph control group, while 6.25 mg/kg represents a non-effective dose. The data suggest that a systemically administered GSK-3 inhibitor can cross the BBB and exhibit CNS-directed effects in vivo.

Example 7

In Vivo Synergy of Systemically Administered GSK-3 Inhibitors and Lithium

Figure 25:
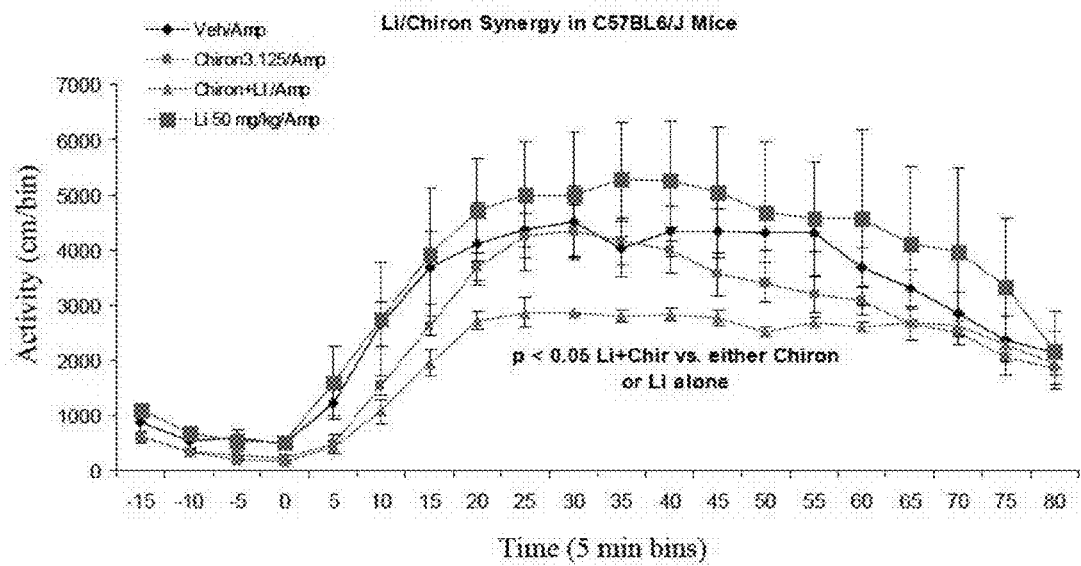
FIG. 25 illustrates the synergy of systemic Chir99021 and systemic lithium.

FIG. 25 shows a synergistic effect of systemically administered Chir99021 and systemically administered lithium. The Figure shows activity measurements of C57BL/6J mice pre-treated with vehicle (DMSO) and challenged with amphetamine (Veh/Amp), pre-treated with 3.12 mg/kg Chir99021, administered i.p., and challenged with amphetamine (Chir 3.12/amph), pre-treated with 50 mg/kg lithium (i.p.) and challenged with amphetamine (Li50/amph), and pre-treated with both 3.12 mg/kg Chir99021 and 50 mg/kg lithium, both administered i.p., and challenged with amphetamine (Li50+Chir/amph) (N=5-8/group). Neither Chir99021 (3.12 mg/kg systemic i.p.) nor lithium (50 mg/kg systemic i.p.) attenuated AIH when administered alone, consistent with the effect observed after ICV administration of Chir99021. However, co-administration of the two sub-effective doses resulted in a significant attenuation of AIH, suggesting that Chir99021 could be used in combination with low dose lithium to minimize potential side-effects of high doses of either drug alone when both are administered systemically. The synergistic effect is equal to the most effective lithium-only dose after systemic administration (FIG. 14). Thus, the level of AIH attenuation achieved by administering a synergistic combination is equal to the level of attenuation achievable with current state of the art treatments.

Example 8

In Vivo Effect of GSK-3 Inhibitors in Lithium-Nonresponsive AIH

While lithium can be used effectively in the treatment of many patients diagnosed with a mood disorder, for example, bipolar disorder, a significant fraction of patients diagnosed with such disorders do not respond to lithium treatment (non-responsive subjects). We investigated the effect of a GSK-3 inhibitor, as provided by some aspects of this invention, in a model of AIH using a strain of mice that does not respond to lithium treatment with AIH attenuation (lithium-non-responsive AIH model).

Figure 26:
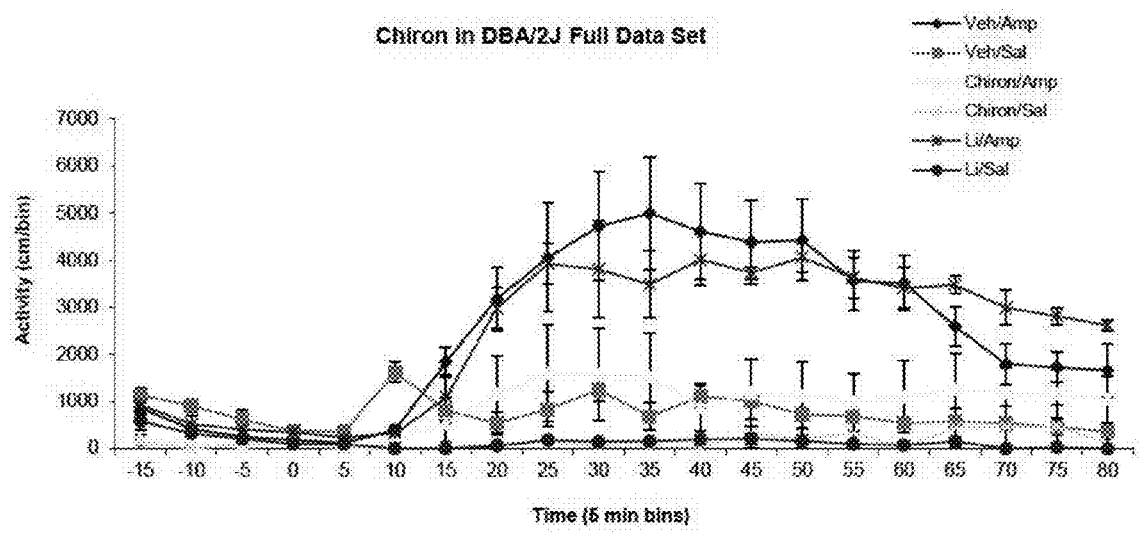
FIG. 26 illustrates a systemic Chir99021 dose response in lithium-nonresponsive AIH.

FIG. 26 shows activity measurements of DBA/2J mice, a strain known to display lithium-non-responsive AIH (see Gould T D, O'Donnell K C, Picchini A M, Manji H K, *Strain differences in lithium attenuation of d-amphetamine-induced hyperlocomotion: a mouse model for the genetics of clinical response to lithium*. Neuropsychopharmacology. 2007 June; 32(6):1321-33), either pre-treated with vehicle (DMSO) and challenged with amphetamine (Veh/Amp), pre-treated with vehicle (DMSO) and mock-challenged with saline (Veh/Sal), pre-treated with 50 mg/kg Chir99021, administered i.p., and challenged with amphetamine (Chir/amph), pre-treated with 12.5 mg/kg Chir99021, administered i.p., and mock-challenged with saline (Chir/sal), pre-treated with 85 mg/kg lithium (i.p.) and challenged with amphetamine (Li/amph), or pre-treated with 85 mg/kg lithium (i.p.) and mock-challenged with saline (Li/sal)(N=4-8/group). While lithium did not significantly attenuate AIH in this strain at a dose effective in lithium-responsive subjects, Chir99021 effected a significant attenuation of AIH, suggesting that the mechanism of action of lithium and Chir99021 may be distinct. These data demonstrate that GSK-3 inhibitors, as provided by aspects of this invention, are able to affect phenotypes correlated to mood disorders, such as the AIH model used in some experiments described herein, in subjects that are not responsive to lithium treatment.

Figure 27:
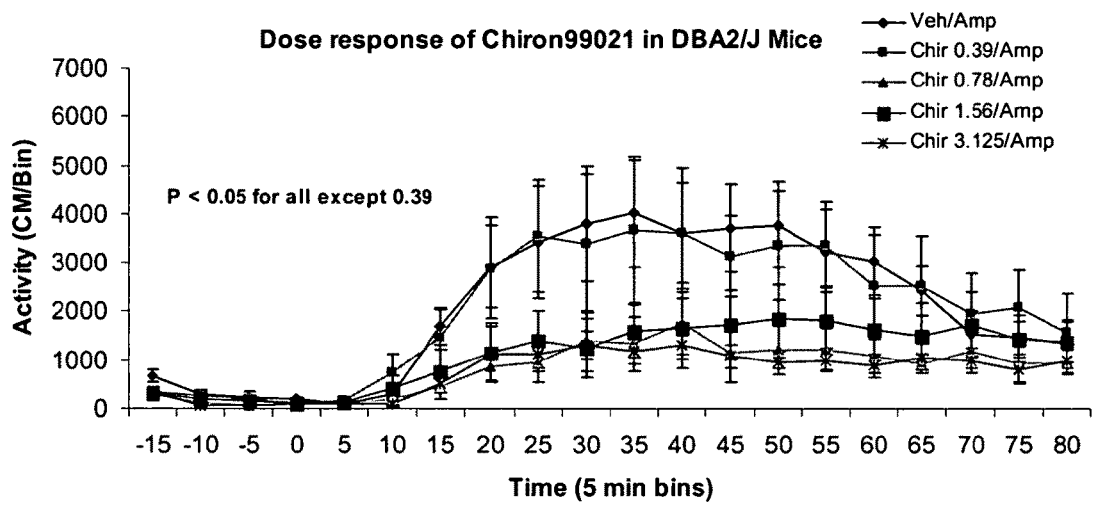
FIG. 27 illustrates a systemic Chir99021 dose response in lithium-nonresponsive AIH.

FIG. 27 shows a dose response to systemic (i.p.) administration of Chir99021 in AIH subjects not responsive to lithium treatment (N=4-5/group). The data show that Chir99021 is more effective in DBA/2J mice than was observed for C57BL/6J mice. Chiron99021 attenuated AIH down to 0.78 mg/kg in DBA/2J mice, compared with 12.5 mg/kg in C57BL/6J mice. These data suggest that DBA/2J mice are responsive to Chiron99021 while being nonresponsive to lithium.

Figure 28:
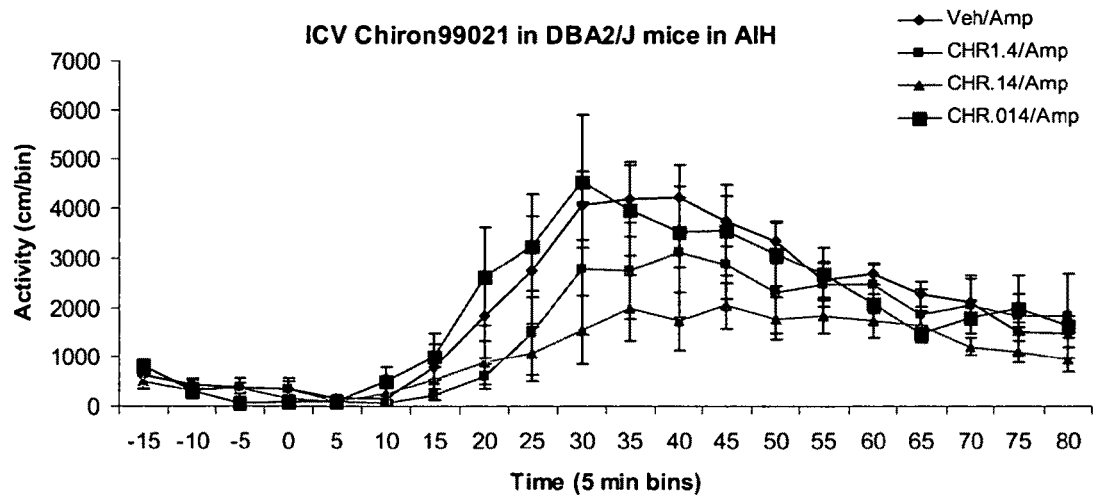
FIG. 28 illustrates an ICV Chir99021 dose response in lithium-nonresponsive AIH.

FIG. 28 shows a dose response of lithium-nonresponsive AIH after ICV administration of Chir99021. The compound, administered at 1.4 µg and 0.14 µg doses (1 µl infusion; N=4-5/group)) significantly attenuated AIH in DBA/2J mice. These data demonstrate that the effects observed with systemic administration of Chir99021 are likely mediated in the CNS.

Example 9

Figure 29:
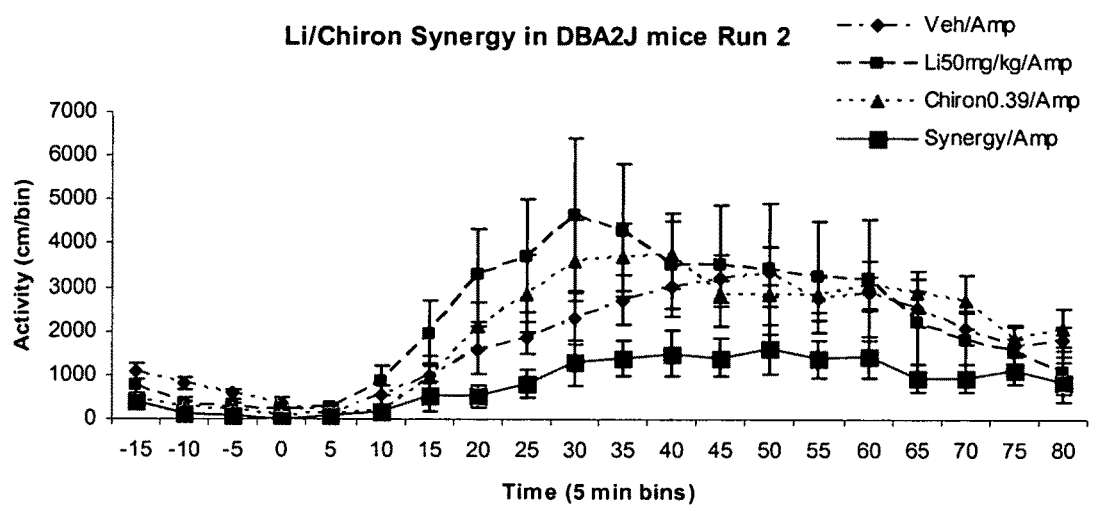
FIG. 29 illustrates the synergy of systemic Chir99021 and lithium in lithium-nonresponsive AIH.

In Vivo Synergy of Systemically Administered GSK-3 Inhibitors and Lithium in Lithium-Nonresponsive AIH FIG. 29 shows that neither Chir99021 at 0.39 mg/kg i.p. nor lithium at 50 mg/kg i.p. attenuated AIH when administered alone to lithium nonresponsive DBA/2J mice. However, co-administration of Chir99021 and lithium ("synergy" group in FIG. 29) at these sub-effective doses, surprisingly, resulted in a significant attenuation of AIH, suggesting that a synergistic combination of Chir99021 and low dose lithium could be used in subjects, for example, human patients having a neurological disease or psychological disorder, that fail to respond fully (e.g., remit) with lithium.

Accordingly, based on the experiments described above, GSK-3 inhibitors described herein are useful in the treatment of some aspects of neurological diseases or psychological disorders. Further, the experiments show that a combination of a GSK-3 inhibitor and an additional compound, e.g., lithium, exhibit a synergistic effect in the treatment of some aspects of neurological diseases or psychological disorders. The data further demonstrate that this synergistic effect can be achieved by administering low doses, for example, sub-effective doses, of the GSK-3 inhibitor and the additional compound. Additionally, the experiments in DBA2/J mice demonstrate that the GSK-3 inhibitors described herein can be used, for example, in combination with an additional compound (e.g., lithium) in the treatment of a subject non-responsive to lithium.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an", as used herein in the specification and in the claims, unless clearly indicated to the contrary, should be understood to mean "at least one."

The phrase "and/or," as used herein in the specification and in the claims, should be understood to mean "either or both" of the elements so conjoined, i.e. elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein, the term "any" is meant to be non-limiting. For example "any of these compounds" referring to a list of compounds, can mean any single one of the compounds listed by itself, any combination of two or more compounds on the list, any combination of at least one compound on the list with a non-listed compound, or a combination of all of the compounds on the list with or without additional compounds.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

REFERENCES

Gould T D, Picchini A M, Einat H, Manji H K. Targeting glycogen synthase kinase-3 in the CNS: implications for the development of new treatments for mood disorders. Curr Drug Targets. 2006 November; 7(11):1399-409.

Gould T D, Einat H, O'Donnell K C, Picchini A M, Schloesser R J, Manji Beta-catenin overexpression in the mouse brain phenocopies lithium-sensitive behaviors. Neuropsychopharmacology. 2007 October; 32(10):2173-83.

Zarate C A Jr, Manji H K. Bipolar Disorder: candidate drug targets. Mt Sinai J. Med. 2008 May-June; 75(3):226-47.

Catapano L A, Manji H K. Kinases as drug targets in the treatment of Bipolar Disorder. Drug Discov Today. 2008 April; 13(7-8):295-302.

Mathew S J, Manji H K, Charney D S. Novel drugs and therapeutic targets for severe mood disorders. Neuropsychopharmacology. 2008 August; 33(9):2080-92.

Zarate C A Jr, Singh J B, Carlson P J, Quiroz J, Jolkovsky L, Luckenbaugh D A, Manji H K. Efficacy of a protein kinase C inhibitor (tamoxifen) in the treatment of acute mania: a pilot study. Bipolar Disord. 2007 September; 9(6):561-70.

Einat H, Yuan P, Szabo S T, Dogra S, Manji H K. Protein kinase C inhibition by tamoxifen antagonizes manic-like behavior in rats: implications for the development of novel therapeutics for Bipolar Disorder. Neuropsychobiology. 2007; 55(3-4):123-31.

Manji H K, Quiroz J A, Payne J L, Singh J, Lopes B P, Viegas J S, Zarate C A. The underlying neurobiology of Bipolar Disorder. World Psychiatry. 2003 October; 2(3):136-46.

Gould T D, Manji H K. Glycogen synthase kinase—a putative molecular target for lithium mimetic drugs. Neuropsychopharmacology. 2005 July; 30(7):1223-37.

Quiroz J A, Gould T D, Manji H K. Molecular effects of lithium. Mol Interv. 2004 October; 4(5):259-72.

Gould T D, Quiroz J A, Singh J, Zarate C A, Manji H K. Emerging experimental therapeutics for Bipolar Disorder: insights from the molecular and cellular actions of current mood stabilizers. Mol Psychiatry. 2004 August; 9(8):734-55.

Gould T D, Zarate C A, Manji H K. Glycogen synthase kinase—a target for novel Bipolar Disorder treatments. J Clin Psychiatry. 2004 January; 65(1):10-21.

Gould T D, Chen G, Manji H K. In vivo evidence in the brain for lithium inhibition of glycogen synthase kinase-3. Neuropsychopharmacology. 2004 January; 29(1):32-8.

Gould T D, Gray N A, Manji H K. Effects of a glycogen synthase kinase-3 inhibitor, lithium, in adenomatous polyposis coli mutant mice. Pharmacol Res. 2003 July; 48(1):49-53.

Gould T D, Manji H K. The Wnt signaling pathway in Bipolar Disorder. Neuroscientist. 2002 October; 8(5):497-511.

Gould T D, Manji H K. Signaling networks in the pathophysiology and treatment of mood disorders. J Psychosom Res. 2002 August; 53(2):687-97.

Manji H K, Chen G. P K C, MAP kinases and the bcl-2 family of proteins as long-term targets for mood stabilizers. Mol Psychiatry. 2002; 7 Suppl S46-56.

Manji H K, Moore G J, Chen G. Bipolar Disorder: leads from the molecular and cellular mechanisms of action of mood stabilisers. Br J Psychiatry. 2001 June; 178(Suppl 41): S107-19.

Ikonomov O C, Manji H K. Molecular mechanisms underlying mood stabilization in manic-depressive illness: the phenotype challenge. Am J Psychiatry. 1999 October; 156 (10):1506-14.

Chen G, Huang L D, Jiang Y M, Manji H K. The mood-stabilizing compound valproate inhibits the activity of glycogen synthase kinase-3. J Neurochem. 1999 March; 72(3):1327-30.

Manji H K, Potter W Z, Lenox R H. Signal transduction pathways. Molecular targets for lithium's actions. Arch Gen Psychiatry. 1995 July; 52(7):531-43.

O'Donnell and Gould, The behavioral actions of lithium in rodent models: leads to develop novel therapeutics. Neurosci Biobehav Rev. 31(6):932-62; 2007

Gould T D, O'Donnell K C, Picchini A M, Manji H K. Strain differences in lithium attenuation of d-amphetamine-induced hyperlocomotion: a mouse model for the genetics of clinical response to lithium. Neuropsychopharmacology. 2007 June; 32(6):1321-33. Epub 2006 Dec. 6.

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

It is claimed:

1. A method for treating bipolar disorder in a subject, comprising administering ruboxistaurin, or a pharmaceutically acceptable salt thereof, to the subject in an effective amount to treat the bipolar disorder based on said subject being indicated or diagnosed to have bipolar disorder, wherein the subject is non-responsive to lithium.

2. The method of claim 1, further comprising diagnosing bipolar disorder in the subject and administering ruboxistaurin, or a pharmaceutically acceptable salt thereof, to the subject based on this diagnosis.

3. The method of claim 1, wherein the method does not comprise administering lithium to the subject.

4. The method of claim 1, further comprising administering an additional compound to said subject, wherein said additional compound is indicated in the treatment of a neurological disease and/or psychiatric disorder.

5. The method of claim 4, wherein said additional compound is lithium, divalproex sodium, or lamotrigene.

6. The method of claim 5, wherein lithium is administered at a sub-effective dose.

7. The method of claim 5, wherein ruboxistaurin is administered at a sub-effective dose.

8. The method of claim 5, wherein ruboxistaurin is administered at a sub-effective dose, and wherein lithium is administered at a sub-effective dose.

9. A method for treating bipolar disorder in a subject, comprising administering a GSK-3 inhibitor having an $IC_{50}$ of less than 1 mM to a subject in an effective amount to treat the bipolar disorder based on said subject being indicated or diagnosed to have bipolar disorder, wherein the subject is non-responsive to lithium.

10. The method of claim 9, further comprising diagnosing bipolar disorder in the subject and administering the GSK-3 inhibitor to the subject based on this diagnosis.

11. The method of claim 9, wherein the method does not comprise administering lithium to the subject.

12. The method of claim 9, further comprising administering an additional compound to said subject, wherein said additional compound is indicated in the treatment of a neurological disease and/or psychiatric disorder.

13. The method of claim 12, wherein said additional compound is divalproex sodium.

14. The method of claim 12, wherein said additional compound is lamotrigene.

15. The method of claim 12, wherein said additional compound is lithium.

16. The method of claim 15, wherein lithium is administered at a sub-effective dose.

17. The method of claim 15, wherein the GSK-3 inhibitor is administered at a sub-effective dose.

18. The method of claim 15, wherein the GSK-3 inhibitor is administered at a sub-effective dose, and wherein lithium is administered at a sub-effective dose.

* * * * *

SEQUENCE LISTING

<160> NUMBER OF SEQ ID NOS: 4

<210> SEQ ID NO 1
<211> LENGTH: 2200
<212> TYPE: DNA
<213> ORGANISM: Homo sapiens

<400> SEQUENCE: 1

| | | | | | | |
|---|---|---|---|---|---|---|
| cccaagccag | agcggcgcgg | cctggaagag | gccagggccc | ggggaggcg | gcggcagcgg | 60 |
| cggcggctgg | ggcagcccgg | gcagcccgag | ccccgcagcc | tgggcctgtg | ctcggcgcca | 120 |
| tgagcggcgg | cgggccttcg | ggaggcggcc | ctggggctc | gggcagggcg | cggactagct | 180 |
| cgttcgcgga | gcccggcggc | ggaggcggag | gaggcggcgg | cggccccgga | ggctcggcct | 240 |
| ccggcccagg | cggcaccggc | ggcggaaagg | catctgtcgg | ggccatgggt | ggggcgtcg | 300 |
| gggcctcgag | ctccgggggt | ggacccggcg | gcagcggcgg | aggaggcagc | ggaggccccg | 360 |
| gcgcaggcac | tagcttcccg | ccgcccgggg | tgaagctggg | ccgtgacagc | gggaaggtga | 420 |
| ccacagtcgt | agccactcta | ggccaaggcc | cagagcgctc | caagaagtg | gcttacacgg | 480 |
| acatcaaagt | gattggcaat | ggctcatttg | gggtcgtgta | ccaggcacgg | ctggcagaga | 540 |
| ccagggaact | agtcgccatc | aagaaggttc | tccaggacaa | gaggttcaag | aaccgagagc | 600 |
| tgcagatcat | gcgtaagctg | gaccactgca | atattgtgag | gctgagatac | tttttctact | 660 |
| ccagtggcga | gaagaaagac | gagctttacc | taaatctggt | gctggaatat | gtgcccgaga | 720 |
| cagtgtaccg | ggtggcccgc | cacttcacca | aggccaagtt | gaccatccct | atcctctatg | 780 |
| tcaaggtgta | catgtaccag | ctcttccgca | gcttggccta | catccactcc | cagggcgtgt | 840 |
| gtcaccgcga | catcaagccc | cagaacctgc | tggtggaccc | tgacactgct | gtcctcaagc | 900 |
| tctgcgattt | tggcagtgca | aagcagttgg | tccgagggga | gcccaatgtc | tcctacatct | 960 |
| gttctcgcta | ctaccgggcc | ccagagctca | tctttggagc | cactgattac | acctcatcca | 1020 |
| tcgatgtttg | gtcagctggc | tgtgtactgg | cagagctcct | cttgggccag | cccatcttcc | 1080 |
| ctggggacag | tggggtggac | cagctggtgg | agatcatcaa | ggtgctggga | acaccaaccc | 1140 |
| gggaacaaat | ccgagagatg | aaccccaact | acacggagtt | caagttccct | cagattaaag | 1200 |
| ctcaccctg | gacaaaggtg | ttcaaatctc | gaacgccgcc | agaggccatc | gcgctctgct | 1260 |
| ctagcctgct | ggagtacacc | ccatcctcaa | ggctctcccc | actagaggcc | tgtgcgcaca | 1320 |
| gcttctttga | tgaactgcga | tgtctgggaa | cccagctgcc | taacaaccgc | ccacttcccc | 1380 |
| ctctcttcaa | cttcagtgct | ggtgaactct | ccatccaacc | gtctctcaac | gccattctca | 1440 |
| tccctcctca | cttgaggtcc | ccagcgggca | ctaccaccct | caccccgtcc | tcacaagctt | 1500 |
| taactgagac | tccgaccagc | tcagactggc | agtcgaccga | tgccacacct | accctcacta | 1560 |
| actcctcctg | agggccccac | caagcaccct | tccacttcca | tctggagcc | ccaagagggg | 1620 |
| ctgggaaggg | gggccatagc | ccatcaagct | cctgccctgg | ctgggcccct | agactagagg | 1680 |
| gcagaggtaa | atgagtccct | gtccccacct | ccagtccctc | cctcaccagc | ctcacccctg | 1740 |
| tggtgggctt | tttaagagga | ttttaactgg | ttgtggggag | ggaagagaag | gacagggtgt | 1800 |
| tgggggatg | aggacctcct | accccttgg | cccctcccc | tccccagac | ctccacctcc | 1860 |
| tccagacccc | ctccctcct | gtgtcccttg | taaatagaac | cagcccagcc | cgtctcctct | 1920 |
| tcccttccct | ggccccggg | tgtaaataga | ttgttataat | ttttttctta | aagaaaacgt | 1980 |
| cgattcgcac | cgtccaacct | ggccccgccc | tcctacagc | tgtaactccc | ctcctgtcct | 2040 |
| ctgcccccaa | ggtctactcc | ctcctcaccc | caccctggag | ggccagggga | gtggagagag | 2100 |

```
ctcctgatgt cttagtttcc acagtaaggt ttgcctgtgt acagacctcc gttcaataaa      2160
ttattggcat gaaaacctga aaaaaaaaaa aaaaaaaaa                              2200
```

<210> SEQ ID NO 2
<211> LENGTH: 483
<212> TYPE: PRT
<213> ORGANISM: Homo sapiens

<400> SEQUENCE: 2

```
Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
        115                 120                 125

Ser Phe Gly Val Val Tyr Gln Ala Arg Leu Ala Glu Thr Arg Glu Leu
    130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
        195                 200                 205

Phe Thr Lys Ala Lys Leu Thr Ile Pro Ile Leu Tyr Val Lys Val Tyr
    210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
            260                 265                 270

Gly Glu Pro Asn Val Ser Tyr Ile Cys Ser Arg Tyr Tyr Arg Ala Pro
        275                 280                 285

Glu Leu Ile Phe Gly Ala Thr Asp Tyr Thr Ser Ser Ile Asp Val Trp
    290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
            340                 345                 350
```

```
Glu Phe Lys Phe Pro Gln Ile Lys Ala His Pro Trp Thr Lys Val Phe
            355                 360                 365
Lys Ser Arg Thr Pro Pro Glu Ala Ile Ala Leu Cys Ser Ser Leu Leu
        370                 375                 380
Glu Tyr Thr Pro Ser Ser Arg Leu Ser Pro Leu Glu Ala Cys Ala His
385                 390                 395                 400
Ser Phe Phe Asp Glu Leu Arg Cys Leu Gly Thr Gln Leu Pro Asn Asn
                405                 410                 415
Arg Pro Leu Pro Pro Leu Phe Asn Phe Ser Ala Gly Glu Leu Ser Ile
            420                 425                 430
Gln Pro Ser Leu Asn Ala Ile Leu Ile Pro Pro His Leu Arg Ser Pro
        435                 440                 445
Ala Gly Thr Thr Thr Leu Thr Pro Ser Ser Gln Ala Leu Thr Glu Thr
    450                 455                 460
Pro Thr Ser Ser Asp Trp Gln Ser Thr Asp Ala Thr Pro Thr Leu Thr
465                 470                 475                 480
Asn Ser Ser

<210> SEQ ID NO 3
<211> LENGTH: 1639
<212> TYPE: DNA
<213> ORGANISM: Homo sapiens

<400> SEQUENCE: 3
atcatctata tgttaaatat ccgtgccgat ctgtcttgaa ggagaaatat atcgcttgtt      60
ttgttttta tagtatacaa aaggagtgaa aagccaagag gacgaagtct ttttctttt      120
cttctgtggg agaacttaat gctgcattta tcgttaacct aacaccccaa cataaagaca     180
aaaggaagaa aaggaggaag gaaggaaaag gtgattcgcg aagagagtga tcatgtcagg     240
gcggcccaga accacctcct tgcggagag ctgcaagccg gtgcagcagc cttcagcttt      300
tggcagcatg aaagttagca gagacaagga cggcagcaag gtgacaacag tggtggcaac     360
tcctgggcag ggtccagaca ggccacaaga agtcagctat acagacacta agtgattgg      420
aaatggatca tttggtgtgg tatatcaagc caaactttgt gattcaggag aactggtcgc     480
catcaagaaa gtattgcagg acaagagatt taagaatcga gagctccaga tcatgagaaa     540
gctagatcac tgtaacatag tccgattgcg ttatttcttc tactccagtg gtgagaagaa     600
agatgaggtc tatcttaatc tggtgctgga ctatgttccg gaaacagtat acagagttgc     660
cagacactat agtcgagcca acagacgct ccctgtgatt tatgtcaagt tgtatatgta      720
tcagctgttc cgaagtttag cctatatcca ttcctttgga atctgccatc gggatattaa     780
accgcagaac ctcttgttgg atcctgatac tgctgtatta aaactctgtg actttggaag     840
tgcaaagcag ctggtccgag agaacccaa tgtttcgtat atctgttctc ggtactatag     900
ggcaccagag ttgatctttg gagccactga ttatacctct agtatagatg tatggtctgc     960
tggctgtgtg ttggctgagc tgttactagg acaaccaata tttccagggg atagtggtgt    1020
ggatcagttg gtagaaataa tcaaggtcct gggaactcca acaagggagc aaatcagaga    1080
aatgaaccca aactacacag aatttaaatt ccctcaaatt aaggcacatc cttggactaa    1140
ggattcgtca ggaacaggac atttcacctc aggagtgcgg tcttccgac cccgaactcc     1200
accggaggca attgcactgt gtagccgtct gctggagtat acaccaactg cccgactaac    1260
accactggaa gcttgtgcac attcattttt tgatgaatta cgggacccaa atgtcaaact    1320
accaaatggg cgagacacac ctgcactctt caacttcacc actcaagaac tgtcaagtaa    1380
```

```
tccacctctg gctaccatcc ttattcctcc tcatgctcgg attcaagcag ctgcttcaac   1440
ccccacaaat gccacagcag cgtcagatgc taatactgga gaccgtggac agaccaataa   1500
tgctgcttct gcatcagctt ccaactccac ctgaacagtc ccgagcagcc agctgcacag   1560
gaaaaaccac cagttacttg agtgtcactc agcaacactg gtcacgtttg gaaagaatat   1620
taaaaaaaaa aaaaaaaa                                                 1639
```

<210> SEQ ID NO 4
<211> LENGTH: 433
<212> TYPE: PRT
<213> ORGANISM: Homo sapiens

<400> SEQUENCE: 4

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320
```

-continued

```
Arg Thr Pro Pro Glu Ala Ile Ala Leu Cys Ser Arg Leu Leu Glu Tyr
            325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
            405                 410                 415

Asp Arg Gly Gln Thr Asn Asn Ala Ala Ser Ala Ser Ala Ser Asn Ser
            420                 425                 430

Thr
```